US009403899B2

(12) United States Patent
Teschner et al.

(10) Patent No.: US 9,403,899 B2
(45) Date of Patent: Aug. 2, 2016

(54) METHOD FOR REDUCING THE THROMBOEMBOLIC POTENTIAL OF A PLASMA-DERIVED IMMUNOGLOBULIN COMPOSITION

(75) Inventors: Wolfgang Teschner, Vienna (AT); Harald Arno Butterweck, Vienna (AT); Bernhard Kölbl, Achau (AT); Lucia Hofbauer, Eggenburg (AT); Hans-Peter Schwarz, Vienna (AT)

(73) Assignees: Baxalta Incorporated, Bannockburn (IL); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 13/595,967

(22) Filed: Aug. 27, 2012

(65) Prior Publication Data

US 2013/0058961 A1   Mar. 7, 2013

Related U.S. Application Data

(60) Provisional application No. 61/527,974, filed on Aug. 26, 2011.

(51) Int. Cl.
*C07K 16/00* (2006.01)
*C07K 16/06* (2006.01)

(52) U.S. Cl.
CPC ................... *C07K 16/065* (2013.01)

(58) Field of Classification Search
None
See application file for complete search history.

(56) References Cited

U.S. PATENT DOCUMENTS

| | | | |
|---|---|---|---|
| 4,639,513 A | 1/1987 | Hou et al. | |
| 4,877,866 A | 10/1989 | Rudnick et al. | |
| 4,880,913 A | 11/1989 | Doleschel et al. | |
| 5,122,373 A | 6/1992 | Eibl et al. | |
| 5,177,194 A | 1/1993 | Sarno et al. | |
| 5,593,675 A | 1/1997 | Hodler et al. | |
| 6,162,904 A | 12/2000 | Mamidi et al. | |
| 6,835,379 B2 * | 12/2004 | Andersson et al. | 424/130.1 |
| 2001/0051708 A1 * | 12/2001 | Laursen et al. | 530/387.1 |
| 2010/0330071 A1 * | 12/2010 | Teschner et al. | 424/130.1 |

FOREIGN PATENT DOCUMENTS

| | | | |
|---|---|---|---|
| DE | 3641115 A1 | 6/1988 | |
| EP | 0 122 558 A2 | 10/1984 | |
| EP | 0 168 506 A1 | 1/1986 | |
| EP | 0 440 483 A2 | 8/1991 | |
| EP | 0 659 767 A1 | 6/1995 | |
| GB | 1 344 340 A | 1/1974 | |
| GB | 2 039 490 A | 8/1980 | |
| SE | 348942 B | 9/1972 | |
| WO | WO 94/29334 A1 | 12/1994 | |
| WO | WO 97/45140 A1 | 12/1997 | |
| WO | WO 2012/156963 A2 | 11/2012 | |

OTHER PUBLICATIONS

Bellei et al., Amino Acids. Jan. 2011;40(1):145-56. doi: 10.1007/s00726-010-0628-x. Epub May 22, 2010.*
Andersson, T. et al., "An improved chromatography method for production of IgG from Human Plasma," Abstract No. 0520, 1 page.
Barandun, S. et al., "Clinical Tolerance and Catabolism of Plasmin-Treated γ-Globulin for Intravenous Application," *Vox Sang.*, 1975, vol. 28, pp. 157-175.
Barandun, S. et al., "Intravenous Administration of Human γ-Globulin," *Vox Sang.*, 1962, vol. 7, pp. 157-174.
Björkander, C. et al., "1040 Prophylactic Infusions with an Unmodified Intravenous Immunoglobulin Product Causing Few Side-effects in Patients with Antibody Deficiency Syndromes," *Infection 13*, 1985, Nr. 3, pp. 102-110.
Buchacher, A. et al., "Anticomplementary activity of IVIG concentrates—important assay parameters and impact of IgG polymers," *Vox Sanguinis*, 2010, vol. 98, pp. e-209-e218.
Burnouf-Radosevich, M. et al., "A Therapeutic, Highly Purified Factor XI Concentrate From Human Plasma," *Transfusion*, Jan. 1, 1992, vol. 32, No. 9, pp. 861-867.
Cohn, E.J. et al., "A System for the Separation of the Components of Human Blood: Quantitative Procedures for the Separation of the Protein Components of Human Plasma," *J. Am. Chem. Soc.*, Jan. 1950, vol. 72, pp. 465-474.
Cohn, E.J. et al., "Preparation and Properties of Serum and Plasma Proteins. IV. A System for the Separation into Fractions of the Protein and Lipoprotein Components of Biological Tissues and Fluids," *J. Am. Chem. Soc.*, Mar. 1946, vol. 68, pp. 459-475.
Cunningham-Rundles, C. et al., "Long-Term Use of IgA-Depleted Intravenous Immunoglobulin in Immunodeficient Subjects with Anti-IgA Antibodies," *Journal of Clinical Immunology*, 1993, vol. 14, No. 4, pp. 272-278.
Dephillips, P. et al., "Determinants of protein retention characteristics on cation-exchange adsorbents," *Journal of Chromatography*, Nov. 9, 2001, vol. 933, No. 1-2, pp. 57-72.
Deutsch, H.F. et al., "Biophysical Studied of Blood Plasma Proteins: III. Recovery of γ-Globulin From Human Blood Protein Mixtures," *J. Biol. Chem.*, 1946, vol. 164, pp. 109-118.
Etscheid, M. et al., "Identification of kallikrein and FXIa as impurities in therapeutic immunoglobulins: implications for the safety and control of intravenous blood products," *Vox Sanguinis*, 2012, vol. 102, pp. 40-46.

(Continued)

*Primary Examiner* — Michael Szperka
(74) *Attorney, Agent, or Firm* — Morgan, Lewis & Bockius LLP

(57) ABSTRACT

The present invention provides methods for reducing the amidolytic and anti-complement activity (ACA) content of an immunoglobulin composition through the use of cation exchange chromatography. In a specific embodiment, the invention provides methods for reducing the Factor XI and/or Factor XIa and/or ACA content of an immunoglobulin composition by collecting the leading portion of a cation exchange eluate. The present invention also provides immunoglobulin composition having reduced levels of amidolytic activity, Factor XI, and/or Factor XIa, and/or ACA content.

28 Claims, 5 Drawing Sheets

(56) References Cited

OTHER PUBLICATIONS

Hamamoto, Y. et al., "A Novel Method for Removal of Human Immunodeficiency Virus: Filtration with Porous Polymeric Membranes," *Vox Sang*, 1989, vol. 56, pp. 230-236.
Hamilton, R.G., "Human IgG Subclasses," Calbiochem-Novabiochem Corporation, © 1998, 64 pages.
Hedderich, U. et al., "Immunoglobulin substitution therapy in a patient with primary hypogammaglobylinaemia and anti-IgA antibodies," *Clinical Allergy*, 1986, vol. 16, pp. 339-344.
Horowitz, B. et al., "Viral safety of solvent/detergent-treated blood products," *Blood Coagulation and Fibrinolysis*, 1994, vol. 5, Suppl 3, pp. S21-S28.
International Search Report mailed Dec. 5, 2012, for International Patent Application No. PCT/US2012/052567, 4 pages.
Kempf, C. et al., "Virus inactivation during production of intravenous immunoglobulin," *Transfusion*, 1991, vol. 31, No. 5, pp. 423-427.
Kistler, P. et al., "Large Scale Production of Human Plasma Fractions," *Vox Sang.*, 1962, vol. 7, pp. 414-424.
Koblet, H. et al., "Turnover of Standard-Gammaglobulin, pH-4-Gammaglobulin and Pepsin Desaggregated Gammaglobulin and Clinical Implications," *Vox Sang*, 1967, vol. 13, pp. 93-102.
Kreil, T.R. et al., "West Nile virus and the safety of plasma derivatives: verification of high safety margins, and the validity of predictions based on model virus data," *Transfusion*, Aug. 2003, vol. 43, pp. 1023-1028.
Lebing, W. et al., "Properties of a new intravenous immunoglobulin (IGIV-C, 10%) produced by virus inactivation with caprylate and column chromatography," *Vox Sanguinis*, 2003, vol. 84, pp. 193-201.
Louie, R.E. et al., "Inactivation of Hepatitis C Virus in Low pH Intravenous Immunoglobulin," *Biologicals*, 1994, vol. 22, pp. 13-19.
Lucena, A.E.S. et al., "A new methodology for polyvalent intravenous immunoglobulin solution production with a two-stage process of viral inactivation," *Brazilian Journal of Pharmaceutical Sciences 2010 Faculdade de Ciencias Farmaceuticas (Biblioteca) Bra*, Oct. 2010, vol. 45, No. 4, pp. 778-779.
Oncley, J.L. et al., "The Separation of the Antibodies, Isoagglutinins, Prothrombin, Plasminogen and $\beta_1$-Lipoprotein into Subfractions of Human Plasma," *J. Am. Chem. Soc.*, Feb. 1949, vol. 71, pp. 541-550.
Pelletier, J.P.R. et al., "Pathogen inactivation techniques," *Best Practice & Research Clinical Haematology*, 2006, vol. 19, No. 1, pp. 205-242.
Piszkiewicz, D. et al., "Heat Inactivation of Human Immunodeficiency Virus in Lyophilized Factor VIII and Factor IX Concentrates," *Thrombosis Research*, 1987, vol. 47, pp. 235-241.
Staby, A. et al., "Comparison of chromatographic ion-exchange resins," *Journal of Chromatography*, Mar. 25, 2005, vol. 1069, No. 1, pp. 65-77.
Stucki, M. et al., "Characterisation of a chromatographically produced anti-D immunoglobulin product," *Journal of Chromatography B*, 1997, vol. 700, pp. 241-248.
Suomela, H. et al., "Intravenous immunoglobulin of high purity when production includes solvent/detergent treatment," *Biotechnology of Blood Proteins*, 1993, vol. 227, pp. 261-265.
Tanaka, K. et al., "High quality human immunoglobulin G purified from Cohn fractions by liquid chromatography," *Brazilian Journal of Medicine and Biological Research*, 2000, vol. 33, pp. 27-30.
Teschner, W. et al., "A new liquid, intravenous immunoglobulin product (IGIV 10%) highly purified by a state-of-the-art process," *Vox Sanguinis*, 2007, vol. 92, pp. 42-55.
Von Nitschmann, HS. et al., "Vereinfachtes Verfahen zur Gewinnung von humanem Albumin and γ-Globulin aus Blutplasma mittels Alkoholfällung," *Helevetica Chimica Acta*, 1954, vol. 37, pp. 866-873.
Yuasa, T. et al., "The particle size of hepatitis C virus estimated by filtration through microporus regenerated cellulose fibre," *Journal of General Virology*, 1991, vol. 72, pp. 2021-2024.
Zhou et al., "pH-conductivity hybrid gradient cation-exchange chromatography for process-scale monoclonal antibody purification," *Journal of Chromatography*, Oct. 17, 2007, vol. 1175, No. 1, pp. 69-80.
Komenda, M. et al., "Assessment of the ability of the Privigen(R) purification process to deplete thrombogenic factor Xia from plasma," Vox Sanguinis, Jul. 2014, vol. 107, No. 1, pp. 26-36.

\* cited by examiner

METHOD FOR REDUCING THE THROMBOEMBOLIC POTENTIAL OF A PLASMA-DERIVED IMMUNOGLOBULIN COMPOSITION

CROSS-REFERENCE TO RELATED APPLICATION

The present application claims the benefit of U.S. Provisional Application No. 61/527,974, filed Aug. 26, 2011, the content of which is hereby expressly incorporated herein by reference in its entirety for all purposes.

BACKGROUND OF THE INVENTION

Plasma-derived blood products are used to treat not only a variety of blood disorders, but diseases of other origin. For example, immune globulin (IgG) products from human plasma were first used in 1952 to treat immune deficiency. Since then, IgG preparations have found widespread use in at least three main categories of medical conditions: (1) immune deficiencies such as X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

Various safety precautions must be taken into consideration when manufacturing and formulating plasma-derived biologic therapies. These precautions include methods for removing and/or inactivating blood borne pathogens (e.g., viral and bacterial pathogens), anti-complement activity, and other unwanted contaminants arising from the use of donated plasma. Studies have suggested that administration of high levels of amidolytic activity may result in unwanted thromboembolic events (Wolberg A S et al., Coagulation factor XI is a contaminant in intravenous immunoglobulin preparations. Am J Hematol 2000; 65:30-34; and Alving B M et al., Contact-activated factors: contaminants of immunoglobulin preparations with coagulant and vasoactive properties. J Lab Clin Med 1980; 96:334-346; the disclosures of which are hereby incorporated by reference in their entireties for all purposes).

Highlighting this concern was the voluntary withdrawal of Octagam® (Octapharma) in the US and suspension of marketing authorization for Octagam® and Octagam 10% by the European Commission following increased reports of thromboembolic events. It has been suggested that the increased thrombolic events were caused by high levels of amidolytic activity in the biologic, caused by serine protease and serine protease zymogen impurities, such as Factor XI, Factor XIa, Factor XII and Factor XIIa (FDA Notice: Voluntary Market Withdrawal—Sep. 23, 2010 Octagam [Immune Globulin Intravenous (Human)] 5% Liquid Preparation; Octagam 50 mg/ml, solution pour perfusion—Octapharma France—Mise en quarantaine de tous les lots, published online Sep. 9, 2010 by the AFSSAPS; and Questions and answers on the suspension of the marketing authorizations for Octagam (human normal immunoglobulin 5% and 10%), published online Sep. 23, 2010 by the European Medicines Agency).

The EDQM (European Directorate on the Quality of Medicines & Health Care) published a revision of the monograph for human normal immunoglobulin for intravenous administration (0918) for rapid implementation on Jan. 1, 2012 to address the potential pro-coagulant activity in immune globulin products. The revision states that "[t]he method of preparation also includes a step or steps that have been shown to remove thrombosis-generating agents. Emphasis is given to the identification of activated coagulation factors and their zymogens and process steps that may cause their activation. Consideration is also to be given to other procoagulant agents that could be introduced by the manufacturing process."

On Mar. 18, 2011, Swissmedic reported that thromboembolic adverse events have been seen in association with numerous Vivaglobin product lots by FDA. Vivaglobin (160 mg/mL human normal immunoglobulin solution for subcutaneous injection), manufactured by CSL was licensed as replacement therapy for adults and children with primary immunodeficiency syndromes, myeloma, or chronic lymphatic leukemia. The risk of thromboembolic adverse events was not known until this time for this route of administration. Investigations revealed pro-coagulant activity at least in some batches. As a consequence, Vivaglobin was withdrawn from the market and replaced by the new product Hizentra (20% human normal immunoglobulin solution for subcutaneous injection). Due to the adverse events reported for Vivaglobin, it now a requirement that immunoglobulin products for subcutaneous administration have low levels of procoagulant activity, similar to the requirements for intravenous immunoglobulin products.

Dedicated serine proteases, generically known as coagulation factors, are integral components of both the contact activation and tissue factor pathways of the coagulation cascade. Upon a stimulus of the coagulation pathways, serine protease zymogens, which are inactive enzyme precursors, become activated proteases that catalyze the activation of the next protease zymogen, resulting in an activation cascade. This coagulation cascade culminates in the activation of Thrombin (Factor IIa) and Factor XIIIa, which function to convert Fibrinogen (Factor I) into Fibrin (Factor Ia) and cross-link fibrin to form a fibrin clot, respectively.

The contact activation pathway, also known as the intrinsic coagulation pathway, begins with the activation of Kallikrein and Factor XIIa (FXIIa) from Prekallikrein and Factor XII, respectively. The activated serine protease FXIIa cleaves Factor XI (FXI), converting the zymogen into Factor XIa (FXIa), an active serine protease which participates in the subsequent activation of Factor Xa (FXa).

Due to rising concerns over the presence of serine protease and serine protease zymogens in plasma-derived protein compositions, there remains a need in the art for methods for reducing the levels of these contaminants, and particularly FXI and FXIa, in immunoglobulin preparations.

BRIEF SUMMARY OF INVENTION

The present invention provides, among other aspects, methods for reducing the amidolytic content (e.g., FXI and/or FXIa) of IgG immunoglobulin compositions and IgG immunoglobulin compositions having lower levels of amidolytic activity (e.g., FXI and/or FXIa) than comparable compositions available in the marketplace.

In a first aspect, the present invention provides a method for reducing Factor XI (FXI) and/or Factor XIa (FXIa) content in a plasma-derived immunoglobulin composition, the method comprising the steps of: (a) providing a plasma-derived immunoglobulin composition comprising IgG immunoglobulins and FXI and/or FXIa; (b) contacting the plasma-derived immunoglobulin composition with a cation exchange resin disposed in a chromatography column under a first solution condition comprising a pH of no more than 6.0 and a conductivity of no more than 11 mS/cm to bind the IgG immunoglobulins and at least a fraction of the FXI and/or FXIa to the cation exchange resin; (c) eluting the IgG immunoglobulins from the cation exchange resin by contacting the cation exchange resin with an elution buffer comprising a pH of at least 7.5 and a conductivity of at least 15 mS/cm to form an eluate comprising a leading portion and lagging portion; and (d) collecting the leading portion of the eluate separately from the lagging portion of the eluate, wherein the leading portion of the eluate comprises no more than 80% of the eluate.

In one embodiment of the methods provided above, the elution buffer comprises a conductivity of at least 20 mS/cm. In another embodiment of the methods provided above, the elution buffer comprises a conductivity of at least 22 mS/cm. In another embodiment of the methods provided above, the elution buffer comprises a conductivity of at least 25 mS/cm.

In one embodiment of the methods provided above, the method further comprises a step of washing the cation exchange resin having the immunoglobulins and FXI and/or FXIa bound thereto with a wash buffer comprising a pH of no more than 6.0 and a conductivity of less than 11 mS/cm prior to eluting the immunoglobulins from the cation exchange resin in step (c).

In one embodiment of the methods provided above, the cation exchange resin is a weak cation exchange resin. In a specific embodiment of the methods provided above, the weak cation exchange resin is carboxymethyl cation exchange resin.

In one embodiment of the methods provided above, the elution buffer comprises a pH of between 7.5 and 8.5. In another embodiment of the methods provided above, the elution buffer comprises a pH of 8.0±0.2.

In one embodiment of the methods provided above, the elution buffer comprises between 200 and 300 mM sodium chloride. In another embodiment of the methods provided above, the elution buffer comprises between 240 and 260 mM sodium chloride.

In one embodiment of the methods provided above, the elution buffer comprises between 100 mM and 300 mM glycine. In another embodiment of the methods provided above, the elution buffer comprises between 175 mM and 225 mM glycine.

In one embodiment of the methods provided above, the leading portion of the eluate consists of no more than 70% of the eluate.

In one embodiment of the methods provided above, the step of collecting the leading portion of the eluate separately from the lagging portion of the eluate comprises collecting eluate having a pH of no more than 7.0 separately from eluate having a pH of more than 7.0.

In one embodiment of the methods provided above, the step of collecting the leading portion of the eluate separately from the lagging portion of the eluate comprises collecting eluate having a pH of no more than 6.5 separately from eluate having a pH of more than 6.5.

In one embodiment of the methods provided above, the step of collecting the leading portion of the eluate separately from the lagging portion of the eluate comprises collecting eluate having a pH of no more than 6.0 separately from eluate having a pH of more than 6.0.

In one embodiment of the methods provided above, the step of collecting the leading portion of the eluate separately from the lagging portion of the eluate comprises collecting eluate having a pH of no more than 5.5 separately from eluate having a pH of more than 5.5.

In one embodiment of the methods provided above, the step of collecting the leading portion of the eluate separately from the lagging portion of the eluate comprises collecting eluate having a pH of no more than 5.0 separately from eluate having a pH of more than 5.0.

In one embodiment of the methods provided above, the step of collecting the leading portion of the eluate separately from the lagging portion of the eluate comprises monitoring the pH of the eluate.

In one embodiment of the methods provided above, the step of collecting the leading portion of the eluate comprises the sub-steps of: (i) monitoring the optical density of the eluate at 280 nm ($OD_{280}$); (ii) beginning collection when the OD280 of the eluate rises above a first threshold $OD_{280}$ of at least 50 mAU; and (iii) ending collection when the OD280 of the eluate falls below a second threshold $OD_{280}$ of no less than 500 mAU. In a specific embodiment, the second threshold $OD_{280}$ is no less than 1 AU. In another specific embodiment, the second threshold $OD_{280}$ is no less than 2 AU.

In one embodiment of the methods provided above, the wash buffer comprises a pH of between 5.0 and 6.0. In another embodiment of the methods provided above, the wash buffer comprises a pH of 5.5±0.2.

In one embodiment of the methods provided above, less than 50% of the FXI and/or FXIa bound to the cation exchange resin in step (b) is present in the leading portion of the eluate collected in step (d).

In one embodiment of the methods provided above, less than 25% of the FXI and/or FXIa bound to the cation exchange resin in step (b) is present in the leading portion of the eluate collected in step (d).

In one embodiment of the methods provided above, less than 10% of the FXI and/or FXIa bound to the cation exchange resin in step (b) is present in the leading portion of the eluate collected in step (d).

In one embodiment of the methods provided above, the amount of FXI and/or FXIa is determined by performing an amidolytic activity assay using a FXIa-specific substrate.

In one embodiment of the methods provided above, the plasma-derived immunoglobulin composition provided in step (a) is a suspended plasma fraction precipitate selected from the group consisting of a Fraction I precipitate, a Fraction I+II+III precipitate, a Fraction II+III precipitate, Fraction IV-1, a Kistler-Nitschmann Precipitate A, a Kistler-Nitschmann Precipitate B, and a modified precipitate thereof.

In one embodiment of the methods provided above, the plasma-derived immunoglobulin composition provided in step (a) is a suspended Fraction II precipitate.

In one aspect, the present disclosure provides a method for reducing anti-complement activity (ACA) in a plasma-derived immunoglobulin composition, the method comprising the steps of: (a) providing a plasma-derived immunoglobulin composition comprising IgG immunoglobulins and a first amount of ACA; (b) contacting the plasma-derived immunoglobulin composition with a cation exchange resin disposed in a chromatography column under a first solution condition comprising a pH of no more than 6.0 and a conductivity of no more than 11 mS/cm to bind the IgG immunoglobulins and at least a fraction of the first amount of ACA to the cation exchange resin; (c) eluting the IgG immunoglobulins from the cation exchange resin by contacting the cation exchange resin with an elution buffer comprising a pH of at least 7.5 and a conductivity of at least 15 mS/cm to form an eluate comprising a leading portion and lagging portion; and (d) collecting the leading portion of the eluate separately from the lagging portion of the eluate, wherein the leading portion of the eluate comprises no more than 80% of the eluate.

In one embodiment of the methods described above, the elution buffer comprises a conductivity of at least 20 mS/cm.

In another embodiment of the methods described above, the elution buffer comprises a conductivity of at least 22 mS/cm. In another embodiment of the methods described above, the elution buffer comprises a conductivity of at least 25 mS/cm.

In one embodiment of the methods described above, the method further comprises a step of washing the cation exchange resin having the immunoglobulins and ACA bound thereto with a wash buffer comprising a pH of no more than 6.0 and a conductivity of less than 11 mS/cm prior to eluting the immunoglobulins from the cation exchange resin in step (c).

In one embodiment of the methods described above, the cation exchange resin is a weak cation exchange resin. In a specific embodiment of the methods described above, the weak cation exchange resin is carboxymethyl cation exchange resin.

In one embodiment of the methods described above, the elution buffer comprises a pH of between 7.5 and 8.5. In another embodiment of the methods described above, the elution buffer comprises a pH of 8.0±0.2.

In one embodiment of the methods described above, the elution buffer comprises between 200 and 300 mM sodium chloride. In another embodiment of the methods described above, the elution buffer comprises between 240 and 260 mM sodium chloride.

In one embodiment of the methods described above, the elution buffer comprises between 100 mM and 300 mM glycine. In another embodiment of the methods described above, the elution buffer comprises between 175 mM and 225 mM glycine.

In one embodiment of the methods described above, the leading portion of the eluate consists of no more than 70% of the eluate.

In one embodiment of the methods described above, the step of collecting the leading portion of the eluate separately from the lagging portion of the eluate comprises collecting eluate having a pH of no more than 7.0 separately from eluate having a pH of more than 7.0.

In one embodiment of the methods described above, the step of collecting the leading portion of the eluate separately from the lagging portion of the eluate comprises collecting eluate having a pH of no more than 6.5 separately from eluate having a pH of more than 6.5.

In one embodiment of the methods described above, the step of collecting the leading portion of the eluate separately from the lagging portion of the eluate comprises collecting eluate having a pH of no more than 6.0 separately from eluate having a pH of more than 6.0.

In one embodiment of the methods described above, the step of collecting the leading portion of the eluate separately from the lagging portion of the eluate comprises collecting eluate having a pH of no more than 5.5 separately from eluate having a pH of more than 5.5.

In one embodiment of the methods described above, the step of collecting the leading portion of the eluate separately from the lagging portion of the eluate comprises collecting eluate having a pH of no more than 5.0 separately from eluate having a pH of more than 5.0.

In one embodiment of the methods described above, the step of collecting the leading portion of the eluate separately from the lagging portion of the eluate comprises monitoring the pH of the eluate.

In one embodiment of the methods described above, the step of collecting the leading portion of the eluate comprises the sub-steps of: (i) monitoring the optical density of the eluate at 280 nm (OD280); (ii) beginning collection when the OD280 of the eluate rises above a first threshold OD280 of at least 50 mAU; and (iii) ending collection when the OD280 of the eluate falls below a second threshold OD280 of no less than 500 mAU.

In one embodiment of the methods described above, the second threshold OD280 is no less than 1 AU. In another embodiment of the methods described above, the second threshold OD280 is no less than 2 AU.

In one embodiment of the methods described above, the wash buffer comprises a pH of between 5.0 and 6.0. In another embodiment of the methods described above, the wash buffer comprises a pH of 5.5±0.2.

In one embodiment of the methods described above, the concentration of ACA, relative to the concentration of IgG immunoglobulin, present in the leading portion of the eluate collected in step (d) is lower than the concentration of ACA, relative to the concentration of IgG immunoglobulin, in the plasma-derived immunoglobulin composition provided in step (a).

In one embodiment of the methods described above, the concentration of ACA, relative to the concentration of IgG immunoglobulin, present in the leading portion of the eluate collected in step (d) is at least 25% lower than the concentration of ACA, relative to the concentration of IgG immunoglobulin, in the plasma-derived immunoglobulin composition provided in step (a).

In one embodiment of the methods described above, the concentration of ACA, relative to the concentration of IgG immunoglobulin, present in the leading portion of the eluate collected in step (d) is at least 50% lower than the concentration of ACA, relative to the concentration of IgG immunoglobulin, in the plasma-derived immunoglobulin composition provided in step (a).

In one embodiment of the methods described above, the concentration of ACA, relative to the concentration of IgG immunoglobulin, present in the leading portion of the eluate collected in step (d) is lower than the concentration of ACA, relative to the concentration of IgG immunoglobulin, in the lagging portion of the eluate collected in step (d).

In one embodiment of the methods described above, the concentration of ACA, relative to the concentration of IgG immunoglobulin, present in the leading portion of the eluate collected in step (d) is less than 50% of the concentration of ACA, relative to the concentration of IgG immunoglobulin, in the lagging portion of the eluate collected in step (d).

In one embodiment of the methods described above, the concentration of ACA, relative to the concentration of IgG immunoglobulin, present in the leading portion of the eluate collected in step (d) is less than 25% of the concentration of ACA, relative to the concentration of IgG immunoglobulin, in the lagging portion of the eluate collected in step (d).

In one embodiment of the methods described above, the plasma-derived immunoglobulin composition provided in step (a) is a suspended plasma fraction precipitate selected from the group consisting of a Fraction I precipitate, a Fraction I+II+III precipitate, a Fraction II+III precipitate, Fraction IV-1, a Kistler-Nitschmann Precipitate A, a Kistler-Nitschmann Precipitate B, and a modified precipitate thereof.

In one embodiment of the methods described above, the plasma-derived immunoglobulin composition provided in step (a) is a suspended Fraction II precipitate.

DETAILED DESCRIPTION OF INVENTION

I. Introduction

Figure 1:
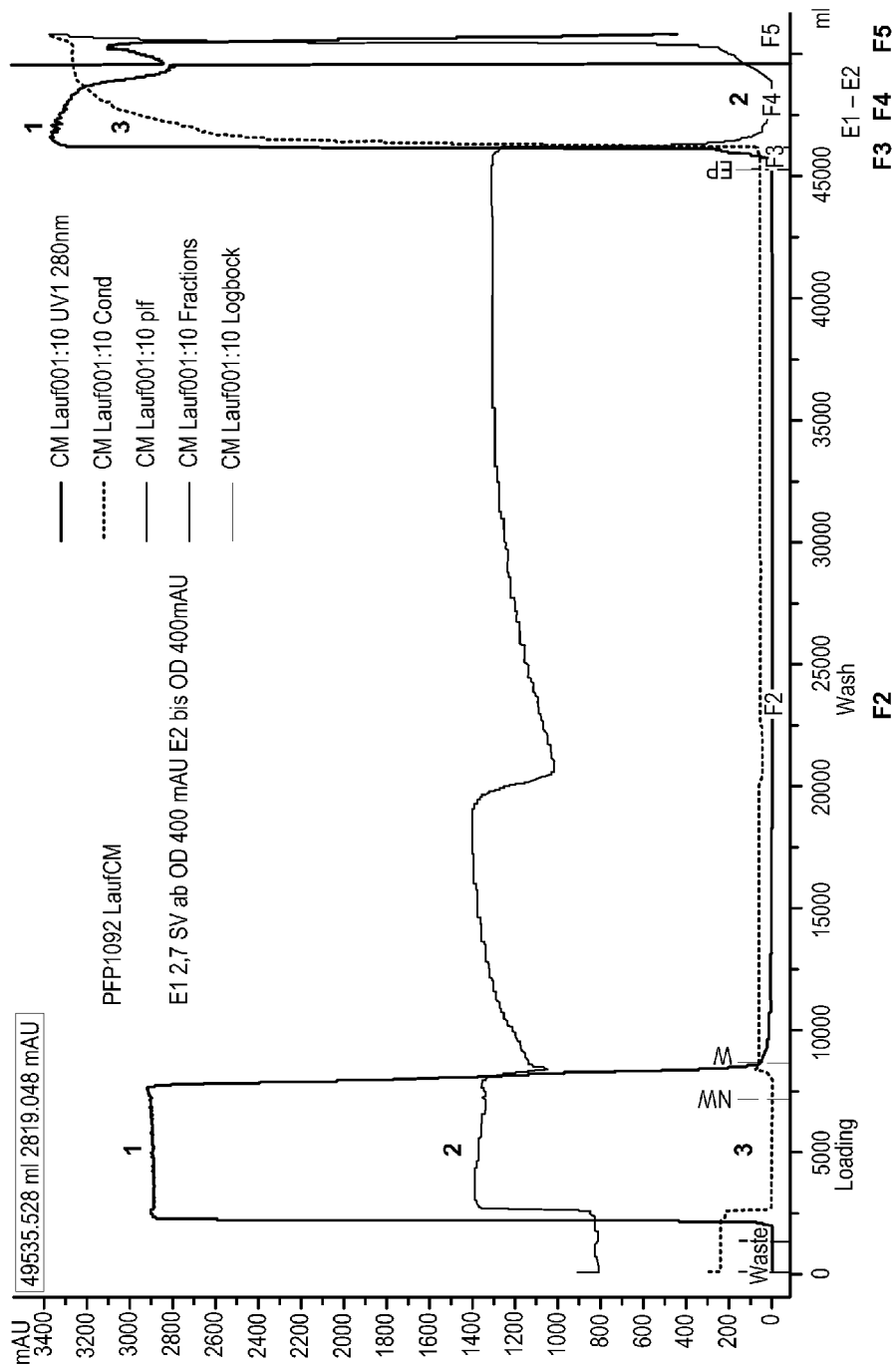
FIG. 1. shows a chromatogram of the CM Sepharose Fast Flow (ff) chromatography step described in Example 1. Line number 1 shows the UV absorbance, line number 2 shows the pH, and line number 3 shows the conductivity of the effluent at the column outlet. The optical density at 280 nanometers indicates a partial separation of two fractions during the elution of the protein from the CM Sepharose ff column. The pH at the column outlet starts to rise just before the beginning of the re-rise of the UV absorbance during elution. At this point the two eluate fractions were separated as shown in the chromatogram as F4 and F5 (fraction 4 and fraction 5), named in the following as E1 and E2.

Given the broad use of therapeutic plasma-derived intravenous immunoglobulin compositions, ensuring the safety of these compositions is of paramount importance. Concerns over the amidolytic content of immunoglobulin compositions paired with the occurrence of thromboembolic events in patients being administered plasma-derived immunoglobulins have highlighted a need for methods of effectively reducing serine proteases (e.g., FXIa and FXIIa) and serine protease zymogens (e.g., FXI and FXII) during the manufacturing of immunoglobulins.

The present invention is based at least in part on the surprising finding that significant amounts of amidolytic activity (e.g., FXI and/or FXIa) and/or anti-complement activity (ACA) can be removed from an immunoglobulin composition by collecting only the leading portion of a cation exchange eluate. As such, methods are provided herein for reducing the concentration of serine proteases and serine protease zymogens during the manufacture of plasma-derived protein compositions.

In one aspect, the invention is based on the discovery that during a single-step elution from a cation exchange resin, IgG immunoglobulins are released from the resin prior to the elution of a significant fraction of amidolytic activity (e.g., contributed by at least FXI and/or FXIa) and/or ACA. Specifically, it was found that upon contacting a cation exchange resin having IgG immunoglobulins and proteins contributing amidolytic activity bound thereto with an elution buffer having a pH of greater than at least 7.0, the initial eluate recovered from the column has a low pH (e.g., a pH below 5.0). After a period of time, the pH of the eluate recovered from the column shifts to above 7.0. Surprisingly, it was found that the initial eluate having a low pH contains low levels of amidolytic activity, FXI and/or FXIa content, and/or ACA content, while the eluate recovered after the shift in pH contains a significantly higher level of amidolytic activity, FXI and/or FXIa content, and/or ACA content.

Accordingly, in one aspect, the present invention is based on a method for separating a significant fraction of amidolytic activity (e.g., Factor XI and/or Factor XIa) and/or ACA from an IgG immunoglobulin composition by binding the IgG immunoglobulins, amidolytic activity, and/or ACA to a cation exchange resin, eluting the IgG immunoglobulins, amidolytic activity, and/or ACA in a single-step elution, and collecting the leading portion of the eluate, characterized by high IgG yield, low amidolytic activity, and/or low ACA content, separately from the lagging portion of the eluate, characterized by low IgG yield, high amidolytic activity, and/or high ACA content.

Among other advantages, the methods of the invention provide (1) simple methods for removing amidolytic activity from IgG immunoglobulin compositions by cation exchange chromatography with a single-step elution; (2) simple methods for rapidly identifying fractions of an IgG immunoglobulin cation exchange eluate having high amidolytic activities (i.e., high FXI and/or FXIa content), based on monitoring the pH of the eluate; (3) methods for removing amidolytic activity from an IgG immunoglobulin composition that are not affected by the concentration of protein loaded onto a cation exchange resin, allowing for simple scale-up for large-scale manufacturing processes; (4) methods that allow for the rapid determination of which IgG immunoglobulin cation exchange elute fractions to use for further processing, based on pH monitoring; (5) methods that allow for a significant reduction in amidolytic activity (e.g., FXI and/or FXIa content) with minimal loss of IgG immunoglobulin yield; (6) methods for manufacturing IgG immunoglobulin compositions having lower IgG aggregate concentration, lower PKA activity, lower amidolytic activity as measured with chromogenic substrates (including, but not limited to substrate PL-1), a higher IgG monomer concentration, and a more desirable IgG subclass distribution; (7) methods that allow for the rapid determination of which cation exchange IgG immunoglobulin elution fractions to use for further processing, based on the elution volume of the chromatographic step; (8) methods that allow for the rapid determination of which IgG immunoglobulin cation exchange elution fractions to use for further processing, based on the protein absorbance of the particular fraction; (9) the ability to utilize the advantageous features of the invention in large-scale manufacturing processes; (10) enrichment of amidolytic activity for identification and quantification; (11) simple methods for removing anti-complement activity (ACA) from IgG immunoglobulin compositions by cation exchange chromatography with a single-step elution; (12) simple methods for rapidly identifying fractions of an IgG immunoglobulin cation exchange eluate having high anti-complement activity (ACA), based on monitoring the pH of the eluate; (13) methods for removing anti-complement activity (ACA) from an IgG immunoglobulin composition that are not affected by the concentration of protein loaded onto a cation exchange resin, allowing for simple scale-up for large-scale manufacturing processes; (14) methods that allow for a significant reduction in anti-complement activity (ACA) with minimal loss of IgG immunoglobulin yield; (15) methods for manufacturing IgG immunoglobulin compositions having lower IgG aggregate concentration, lower anti-complement activity (ACA), a higher IgG monomer concentration, and a more desirable IgG subclass distribution; and (16) enrichment of anti-complement activity (ACA) for identification and quantification.

II. Definitions

As used herein, the term "Intravenous IgG" or "IVIG" treatment refers generally to a therapeutic method of intravenously, subcutaneously, or intramuscularly administering a composition of IgG immunoglobulins to a patient for treating a number of conditions such as immune deficiencies, inflammatory diseases, and autoimmune diseases. The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titers for specific antigens (e.g., Rho D factor, pertussis toxin, tetanus toxin, botulism toxin, rabies, etc.). For ease of discussion, such subcutaneously or intramuscularly formulated IgG compositions are also included in the term "IVIG" in this application.

As used herein, the term "amidolytic activity" refers to the ability of a polypeptide to catalyze the hydrolysis of at least one peptide bond in another polypeptide. The amidolytic activity profile for an IgG immunoglobulin composition may be determined by assaying with various chromogenic substrates, with different specificities for proteases found in human plasma, including without limitation: PL-1 (broad spectrum), S-2288 (broad spectrum), S-2266 (FXIa, glandular kallikreins), S-2222 (FXa, trypsin), S-2251 (Plasmin), and S-2302 (Kallikrein, FXIa, and FXIIa). Methods for determining the amidolytic activity of a composition are well known in the art, for example, as described in M. Etscheid et al. (Identification of kallikrein and FXIa as impurities in therapeutic immunoglobulins: implications for the safety and control of intravenous blood products, Vox Sang 2011; the disclosure of which is hereby expressly incorporated by reference in its entirety for all purposes.)

As used herein, the term "anti-complement activity," "anti-complementary activity," and "ACA" are used interchangeably and refer to the ability of a protein composition, e.g., an immunoglobulin IgG composition, to consume complement potential in a complement assay, for example, a method substantially based on the method described in "Public Health Monograph" No. 74; Standardized Diagnostic Complement Fixation Method and Adaptation to Microtest, Washington, 1965, and E. A. Kabat and M. Mayer, Experimental Immunochemistry; 2nd Ed. Thomas Springfield 1961, the content of which is hereby expressly incorporated by reference in its entirety for all purposes. The typical unit of complement activity is the amount of complement that will produce the lysis of $2.5 \times 10^8$, out of a total of $5 \times 10^8$, optimally sensitized red blood cells in a complement activity described herein.

In one embodiment, ACA is measured using a standardized suspension of antibody-sensitized ovine erythrocytes, which is incubated with different dilutions of guinea pig serum serving as the source of complement. The degree of hemolysis is measured spectrophotometrically. For example, to determine the anticomplementary activity of the immunoglobulin product, test solutions are prepared which contain various amounts of the immunoglobulin product and 2 $C'H_{50}$- units of guinea pig serum per ml. In a specific embodiment, anticomplementary activity is measured by incubating a defined amount of a test material (e.g., 10 mg of immunoglobulin IgG) with a defined amount of guinea-pig complement (e.g., 20 $C'H_{50}$) and the remaining complement is titrated. The anticomplementary activity is expressed as the percentage consumption of complement relative to the complement control, considered to be 100%. In one embodiment, ACA is measured according to the standards set forth in the European Pharmacopoeia: Human normal immunoglobulin for intravenous administration. European Pharmacopoeia 6.3, monograph 2.6.17, 4166-4168. Council of Europe, Strasbourg Cedex, France, the content of which is hereby expressly incorporated herein by reference in its entirety for all purposes.

Methods for decreasing anticomplementary activity of compositions intended for intravenous administration are described in the literature (Schultz, H. E. and Schwick, G., Dtsch. med. Wochenschrift 87 (1962), 1643; Barandun, S. et al., Vox Sang. 28 (1957), 157; Barandun, S. et al., Vox Sang. 7 (1962), 187; and Stephen, W., Z. Klin. Chem. Klin. Biochem. 7 (1969), 282, then contents of which are hereby expressly incorporated herein by reference in their entireties for all purposes).

As used herein, "cryo-poor plasma" refers to the supernatant formed after the cold precipitation (cryo-precipitation) of plasma or pooled plasma at temperatures nearing freezing, e.g., at temperatures below about 10° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation.

As used herein, a "Cohn pool" refers to the starting material used for the fractionation of a plasma sample or pool of plasma samples. Cohn pools include whole plasma, cryo-poor plasma samples, and pools of cryo-poor plasma samples that may or may not have been subjected to a pre-processing step. In certain embodiments, a Cohn pool is a cryo-poor plasma sample from which one or more blood factors have been removed in a pre-processing step, for example, adsorption onto a solid phase (e.g., aluminum hydroxide, finely divided silicon dioxide, etc.), or chromatographic step (e.g., ion exchange or heparin affinity chromatography). Various blood factors, including but not limited to Factor Eight Inhibitor Bypass Activity (FEIBA), Factor IX-complex, Factor VII-concentrate, or Antithrombin III-complex, may be isolated from the cryo-poor plasma sample to form a Cohn pool.

As used herein, the term "leading portion of the eluate" refers to a first fraction of an immunoglobulin composition eluted from a cation exchange resin, the fraction being characterized by high immunoglobulin yield and reduced amidolytic activity as compared to the total amidolytic activity bound to the resin prior to elution. The leading portion of the eluate is the first fraction of an eluate released from a cation exchange column, which occurs prior to the release (i.e., elution) of a second fraction of an immunoglobulin composition (referred to as the "lagging portion of the eluate"). The lagging portion of the eluate contains only a small amount of immunoglobulins (typically not more than 25%, preferably not more than 10%, of the immunoglobulin bound to the column) and is characterized by a higher concentration of amidolytic activity as compared to the leading portion of the eluate. In various embodiments, the leading and lagging portions of the eluate may be defined by various characteristics, including without limitation, the pH of the eluate, the protein yield (e.g., expressed as a percentage of the protein bound to the resin), the protein concentration (e.g., as determined by the optical density) of the eluate, the volume of eluate, and the like.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating proteins from small molecules like sugars and salts.

As used herein, the term "diafiltration" is performed with the same membranes as ultrafiltration and can be run as either tangential flow filtration or dead-end filtration mode. During diafiltration, buffer is introduced into the recycle tank while filtrate is removed from the unit operation. In processes where the product is in the retentate (for example, IgG immunoglobulins), diafiltration washes components out of the product pool into the filtrate, thereby exchanging buffers and reducing the concentration of undesirable species.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly (ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used in this application, the term "spraying" refers to a means of delivering a liquid substance into a system, e.g., during an alcohol precipitation step, such as a modified Cohn fractionation I or II+III precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

By "therapeutically effective amount or dose" or "sufficient/effective amount or dose," it is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

III. Reduction of Amidolytic Activity

In one aspect, the present disclosure provides chromatographic methods for reducing the amidolytic activity (e.g., by reducing the content of FXI/FXIa and/or FXII/FXIIa) of a plasma-derived immunoglobulin IgG composition Likewise, the disclosure also provides plasma-derived immunoglobulin IgG compositions containing low levels of amidolytic activity (e.g., low levels of FXI/FXIa and/or FXII/FXIIa) prepared according to the methods provided herein. Advantageously, the methods described herein provide plasma-derived immunoglobulin IgG compositions with improved safety profiles. Specifically, the compositions provided by these methods have reduced potential to cause unwanted thromboembolic events, as compared to currently manufactured immunoglobulin IgG compositions.

A. Fractionation Methods

The present invention is based in part on the discovery that a majority of the amidolytic activity present in a plasma-derived immunoglobulin composition elutes off of a cation exchange resin in the lagging portion of an eluate created by a step elution, while a majority of the immunoglobulin content of the fraction elutes in the leading portion of said eluate. Accordingly, by collecting the leading portion of the eluate separately from the lagging portion of the eluate, the amidolytic activity of the resulting immunoglobulin preparation is significantly reduced. Specifically, it is shown herein that the Factor XIa content, and thus the amidolytic activity associated with the Factor XIa content, is significantly reduced in immunoglobulin compositions prepared according to the methods provided herein.

Accordingly, in one embodiment, the present invention provides a method for reducing the amount of amidolytic activity in a plasma-derived immunoglobulin composition, the method comprising the steps of: (a) binding IgG immunoglobulins and amidolytic activity (i.e., protein contaminants having amidolytic activity) onto a cation exchange resin; (b) optionally washing the cation exchange resin having proteins bound thereto with a wash buffer to remove loosely associated contaminants; (c) performing a single step elution of the IgG immunoglobulins and amidolytic activity; and (d) collecting the leading portion of the eluate separately from the lagging portion of the eluate, wherein the leading portion of the eluate comprises an IgG immunoglobulin composition having a reduced amount of amidolytic activity as compared to the starting composition and the lagging portion of the eluate contains a high concentration of amidolytic activity. In a specific embodiment, the amidolytic activity is Factor XIa activity present in the composition. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of Factor XI (FXI) and/or Factor XIa (FXIa) in a plasma-derived immunoglobulin composition, the method comprising the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate comprises an IgG immunoglobulin composition having a reduced amount of amidolytic activity as compared to the starting composition and the lagging portion of the eluate contains a high concentration of amidolytic activity. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

In one specific embodiment, the method comprises the steps of: (a) contacting a plasma-derived immunoglobulin composition comprising IgG immunoglobulins and FXI and/or FXIa with a cation exchange resin disposed in a chromatography column under a first solution condition comprising a pH between 4.8 and 5.6 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate comprises an IgG immunoglobulin composition having a reduced amount of amidolytic activity as compared to the starting composition and the lagging portion of the eluate contains a high concentration of amidolytic activity. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

In one specific embodiment, the method comprises the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) washing the resin with the immunoglobulins and FXI and/or FXIa bound thereto with a buffer having a sufficiently low conductivity such that the immunoglobulins are not eluted from the resin and a pH between 5.1 and 5.9; (c) eluting the immunoglobulins from the cation exchange resin by contacting the cation exchange resin with an elution buffer comprising a pH of at least 7.5 and a conductivity of at least 15 mS/cm to form an eluate; and (d) collecting the leading portion of the eluate separately from the lagging portion of the eluate, wherein the leading portion of the eluate comprises an IgG immunoglobulin composition having a reduced amount of amidolytic activity as compared to the starting composition and the lagging portion of the eluate contains a high concentration of amidolytic activity. In a specific embodiment, the pH of the wash buffer is 5.5±0.3. In another specific embodiment, the pH of the wash buffer is 5.5±0.2. In another specific embodiment, the pH of the wash buffer is 5.5±0.1. In another specific embodiment, the pH of the wash buffer is 5.5. In yet other embodiments, the pH of the wash buffer is 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

In one specific embodiment, the method comprises the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of 7.8±0.4 and a conductivity of at least 20 mS/cm to form an eluate; and (c) collecting the leading portion of the eluate separately from the lagging portion of the eluate, wherein the leading portion of the eluate comprises an IgG immunoglobulin composition having a reduced amount of amidolytic activity as compared to the starting composition and the lagging portion of the eluate contains a high concentration of amidolytic activity. In a specific embodiment, the pH of the elution buffer is 7.8±0.3. In another specific embodiment, the pH of the elution buffer is 7.8±0.2. In another specific embodiment, the pH of the elution buffer is 7.8±0.1. In another specific embodiment, the pH of the elution buffer is 7.8. In yet other embodiments, the pH of the elution buffer is 7.0, 7.1, 7.2, 7.36, 7.4, 7.5, 7.6, 7.7, 7.8, 7.9, 8.0, 8.1, 8.2, 8.3, 8.4, or 8.5. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

Generally, the starting material used for the methods provided herein include any plasma fraction or composition comprising IgG immunoglobulin and amidolytic activity. As such, in one embodiment, plasma is partially or wholly fractionated according to any one of the purification schemes known in the art. In a specific embodiment, plasma is fractionated to produce a Fraction I precipitate, a Fraction II precipitate, a Fraction I+II+III precipitate, a Fraction II+III precipitate, Fraction IV-1, a Kistler-Nitschmann Precipitate A, a Kistler-Nitschmann Precipitate B, or a modified precipitation thereof, which may be used as a starting material for the methods provided herein.

In a preferred embodiment, the plasma is fractionated by one or more ethanol precipitation steps. Ethanol precipitations steps may be employed to either precipitate the desired immunoglobulins out of solution, while retaining at least one non-immunoglobulin protein in the supernatant, or precipitate at least one non-immunoglobulin protein out of solution, while retaining the desired immunoglobulin in the supernatant. Methods for fractionating immunoglobulins in this fashion are well known in the art. Exemplary ethanol precipitates include, without limitation, a Fraction I precipitate, a Fraction I+II+III precipitate, a Fraction II+III precipitate, Fraction IV-1, a Kistler-Nitschmann Precipitate A, a Kistler-Nitschmann Precipitate B, and modified precipitates thereof. In a particularly preferred embodiment, immunoglobulins present in cryo-poor plasma are enriched by a four-step ethanol process, comprising a Fraction I+II+III precipitation step, an A precipitation step, a B precipitation step, and a Fraction II precipitation step.

In one embodiment, the starting material for the methods for reducing amidolytic activity provided herein is prepared by ethanol fractionation of pooled human plasma (e.g., cryo-poor plasma). In one specific embodiment, the ethanol fractionation includes Fraction I+II+III precipitation of cryo-poor plasma, Fraction A precipitation of a suspended Fraction I+II+III precipitate, Fraction B precipitation of a suspended Fraction A precipitate, and Fraction II precipitation of a Fraction A supernatant, as described below. In another specific embodiment, the ethanol fractionation includes Fraction I precipitation of cryo-poor plasma, Fraction II+III precipitation of a Fraction I supernatant, and Fraction II precipitation of a suspended Fraction II+III precipitate.

As demonstrated herein, the advantageous features of the methods provided herein are retained when applied to large-scale manufacturing procedures. With respect to the preparation of IgG immunoglobulin compositions, large-scale manufacturing refers to processes that enrich immunoglobulins from at least 100 L of pooled plasma (e.g., cryo-poor plasma) starting material. Generally, large-scale immunoglobulin manufacturing processes will fractionate between 100 L and 20,000 L of pooled plasma per batch. In certain embodiments, a large-scale IgG immunoglobulin manufacturing process refers to the fractionation of at least 100 L of pooled plasma (e.g., cryo-poor plasma). In another embodiment, a large-scale IgG immunoglobulin manufacturing process refers to the fractionation of at least 500 L of pooled plasma (e.g., cryo-poor plasma). In another embodiment, a large-scale IgG immunoglobulin manufacturing process refers to the fractionation of at least 1,000 L of pooled plasma (e.g., cryo-poor plasma). In another embodiment, a large-scale IgG immunoglobulin manufacturing process refers to the fractionation of at least 5,000 L of pooled plasma (e.g., cryo-poor plasma). In yet another embodiment, a large-scale IgG immunoglobulin manufacturing process refers to the fractionation of at least 10,000 L of pooled plasma (e.g., cryo-poor plasma).

Generally, methods containing all combinations of the loading conditions, washing conditions, and elution conditions described above are contemplated. Furthermore, methods containing all combinations of the specific chromatographic conditions are contemplated with all possible schemes for defining and collecting the leading portion of the eluate, as described below.

1. Leading and Lagging Portions of the Cation Exchange Eluate

In one aspect, the present invention provides methods for reducing amidolytic activity, and specifically amidolytic activity contributed from FXIa impurities, present in immunoglobulin preparations by collecting the leading portion of a cation exchange eluate. Advantageously, it is shown herein that the leading portion of an eluate formed by a single step elution of a cation exchange chromatographic step contains the majority of the desired immunoglobulin content, while the lagging portion of the eluate contains the majority of the unwanted amidolytic activity. Because the elution of immunoglobulins and amidolytic activity cannot be completely separated, a division between the leading and lagging portions of the eluate must be determined. Two major considerations may be accounted for when making this determination, namely: (i) that dependent upon how the leading and lagging portions of the eluate are defined, more or less amidolytic activity will be recovered in the leading portion—i.e., a greater portion of amidolytic activity can be separated from the immunoglobulin content when the leading portion of the eluate is defined as a smaller portion of the total eluate, and vice versa; and (ii) that dependent upon how the leading and lagging portions of the eluate are defined, greater or lesser immunoglobulin recovery yields will be present in the leading portion—i.e., a lower immunoglobulin yield will be achieved when the leading portion of the eluate is defined as a smaller portion of the total eluate, and vice versa.

Accordingly, the skilled artisan will decide as to where to draw the boundary between the leading and lagging portions of the cation exchange eluate based on their individual needs. For example, when preparing a small-scale purification for research or a specialized therapeutic purpose, the skilled artisan could maximize the separation power of the method by collecting a smaller leading portion of the eluate, while sacrificing on the final immunoglobulin yield. In contrast, when performing large-scale manufacturing (e.g., processing more than 500 L of cryo-poor plasma), the opportunity cost may dictate that a larger leading portion of the eluate is collected to increase the immunoglobulin recovery yield at the expense of a more modest reduction in the amidolytic activity of the composition.

In various embodiments, the leading and lagging portions of the eluate may be defined by various characteristics, including without limitation, the pH of the eluate, the protein yield (e.g., expressed as a percentage of the protein bound to the resin), the protein concentration (e.g., as determined by the optical density) of the eluate, the volume of eluate, and the like.

a. pH of the Eluate

As demonstrated in the examples provided herein, the beginning of the cation exchange elution step is marked by drop in the pH of the solution coming off of the column, to a pH below 5.0, despite the elution buffer having a higher pH (generally >7.0) than that of the column load and wash steps (generally 5.0-6.0). This drop in pH corresponds with the elution of an immunoglobulin IgG composition having low amidolytic activity and Factor XIa content (for example, see, Table 4 and Table 11, respectively). At a later point in the elution, the pH of the solution coming off of the column rises sharply, to greater than 6.0-8.0. This shift in pH is concomitant with a significant increase in the amidolytic activity and Factor XIa content of the eluate (for example, see, Table 4 and Table 11, respectively). Thus, although a step elution is performed by the application of a single high pH elution buffer (generally greater than 7.0), the elution profile resembles a two-step elution in which IgG immunoglobulins are first eluted from the column, followed by accompanying amidolytic activity (e.g., Factor XI and/or Factor XIa). Thus, in certain embodiments, the leading and lagging portions of the eluate are defined based on the pH of the eluate at the column outlet.

Accordingly, in one aspect, the present invention provides a method for reducing the amount of amidolytic activity in a plasma-derived immunoglobulin composition, the method comprising the steps of: (a) binding IgG immunoglobulins and amidolytic activity (i.e., protein contaminants having amidolytic activity) onto a cation exchange resin; (b) optionally washing the cation exchange resin having proteins bound thereto with a wash buffer to remove loosely associated contaminants; (c) performing a single step elution of the IgG immunoglobulins and amidolytic activity; and (d) collecting the leading portion of the eluate separately from the lagging portion of the eluate, wherein the leading portion of the eluate consists of the portion of the eluate having a pH of no more than 7.0. In a specific embodiment, the leading portion of the eluate consists of the portion of the eluate having a pH of no more than 6.5. In another specific embodiment, the leading portion of the eluate consists of the portion of the eluate having a pH of no more than 6.0. In another specific embodiment, the leading portion of the eluate consists of the portion of the eluate having a pH of no more than 5.5. In another specific embodiment, the leading portion of the eluate consists of the portion of the eluate having a pH of no more than 5.0. In yet other embodiments, the leading portion of the eluate consists of the portion of the eluate having a pH of no more than 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or less. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of Factor XI (FXI) and/or Factor XIa (FXIa) in a plasma-derived immunoglobulin composition, the method comprising the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of the portion of the eluate having a pH of no more than 7.0. In a specific embodiment, the leading portion of the eluate consists of the portion of the eluate having a pH of no more than 6.5. In another specific embodiment, the leading portion of the eluate consists of the portion of the eluate having a pH of no more than 6.0. In another specific embodiment, the leading portion of the eluate consists of the portion of the eluate having a pH of no more than 5.5. In another specific embodiment, the leading portion of the eluate consists of the portion of the eluate having a pH of no more than 5.0. In yet other embodiments, In another specific embodiment, the leading portion of the eluate consists of the portion of the eluate having a pH of no more than 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or less. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

b. Absorbance of the Eluate

In yet another embodiment particularly well suited for large-scale manufacturing of immunoglobulin compositions, the leading and lagging portions of the eluate are defined by the immunoglobulin concentration eluting off of the cation exchange column. For example, during large-scale manufacturing, the immunoglobulin composition may be loaded onto the cation exchange resin at sufficiently high protein loads (e.g., >80 mg protein per mL resin) such that the peak eluate is highly concentrated. In these instances, the leading portion of the eluate can be defined as the fraction of the eluate eluting prior to the point at which the $OD_{280}$ falls below a threshold value. In this fashion, roughly the same yield of immunoglobulins can be reproducibly recovered from one preparation to the next, irrespective of minor variances between the manufacturing runs. As demonstrated in Example 9, application of this collection scheme for a large-scale manufacturing process results in a high yield recovery of an IgG immunoglobulin composition with a significantly reduced TGA and amidolytic activity content.

Accordingly, in one aspect, the present invention provides a method for reducing the amount of amidolytic activity in a plasma-derived immunoglobulin composition, the method comprising the steps of: (a) binding IgG immunoglobulins and amidolytic activity (i.e., protein contaminants having amidolytic activity) onto a cation exchange resin; (b) optionally washing the cation exchange resin having proteins bound thereto with a wash buffer to remove loosely associated contaminants; (c) performing a single step elution of the IgG immunoglobulins and amidolytic activity; and (d) collecting the leading portion of the eluate separately from the lagging portion of the eluate, wherein the leading portion of the eluate consists of the portion of the eluate having an $OD_{280}$ of at least 0.5 AU. In a specific embodiment, the leading portion of the eluate consists of the portion of the eluate having an $OD_{280}$ of at least 1.0 AU. In another specific embodiment, the leading portion of the eluate consists of the portion of the eluate having an $OD_{280}$ of at least 1.5 AU. In another specific embodiment, the leading portion of the eluate consists of the portion of the eluate having an $OD_{280}$ of at least 2.0 AU. In yet other specific embodiments, the leading portion of the eluate consists of the portion of the eluate having an $OD_{280}$ of at least 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of Factor XI (FXI) and/or Factor XIa (FXIa) in a plasma-derived immunoglobulin composition, the method comprising the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of the portion of the eluate having an $OD_{280}$ of at least 2.0 AU. In a specific embodiment, the leading portion of the eluate consists of the portion of the eluate having an $OD_{280}$ of at least 1.5 AU. In another specific embodiment, the leading portion of the eluate consists of the portion of the eluate having an $OD_{280}$ of at least 1.0 AU. In another specific embodiment, the leading portion of the eluate consists of the portion of the eluate having an $OD_{280}$ of at least 0.5 AU. In yet other specific embodiments, the leading portion of the eluate consists of the portion of the eluate having an $OD_{280}$ of at least 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

c. Percentage of the Total Eluate

In yet another embodiment particularly well suited for large-scale manufacturing of immunoglobulin compositions, the leading and lagging portions of the eluate are defined as a percentage of the total protein content of the eluate (e.g., by volume or total protein). By predetermining the percentage of the eluate to collect in the leading portion, the immunoglobulin recovery yield can be tightly controlled. This method for defining the leading and lagging portions of the eluate is particularly useful for manufacturing processes which require a minimum step yield and for processes in which a decision is made based on weighing the cost of reduced immunoglobulin yields with the benefit of producing a composition having a reduced amidolytic and Factor XI and/or Factor XIa content. In this fashion, roughly the same yield of immunoglobulins can be reproducibly recovered from one preparation to the next, irrespective of minor variances between the manufacturing runs. As demonstrated in Example 8, application of this collection scheme can result in a high yield recovery of an IgG immunoglobulin composition with a significantly reduced TGA and amidolytic activity content.

Accordingly, in one aspect, the present invention provides a method for reducing the amount of amidolytic activity in a plasma-derived immunoglobulin composition, the method comprising the steps of: (a) binding IgG immunoglobulins and amidolytic activity (i.e., protein contaminants having amidolytic activity) onto a cation exchange resin; (b) optionally washing the cation exchange resin having proteins bound thereto with a wash buffer to remove loosely associated contaminants; (c) performing a single step elution of the IgG immunoglobulins and amidolytic activity; and (d) collecting the leading portion of the eluate separately from the lagging portion of the eluate, wherein the leading portion of the eluate consists of no more than 80% of the total eluate. In a specific embodiment, the leading portion of the eluate is between 70% and 80% of the total eluate. In another specific embodiment, the leading portion of the eluate is between 60% and 80% of the total eluate. In another specific embodiment, the leading portion of the eluate is between 50% and 80% of the total eluate. In another specific embodiment, the leading portion of the eluate is between 70% and 75% of the total eluate. In yet another specific embodiment, the leading portion of the eluate is between 75% and 80% of the total eluate. In yet other embodiments, the leading portion of the eluate is 70%, 71%, 72%, 73%, 74%, 75%, 76%, 77%, 78%, 79%, or 80% of the total eluate. In another embodiment, the leading portion (i.e., the collected or pooled fraction of interest) of the eluate is no more than 70% of the total eluate. In a specific embodiment, the leading portion of the eluate is between 60% and 70% of the total eluate. In another specific embodiment, the leading portion of the eluate is between 50% and 70% of the total eluate. In another specific embodiment, the leading portion of the eluate is between 60% and 65% of the total eluate. In yet another specific embodiment, the leading portion of the eluate is between 65% and 70% of the total eluate. In yet other embodiments, the leading portion of the eluate is 60%, 61%, 62%, 63%, 64%, 65%, 66%, 67%, 68%, 69%, or 70% of the total eluate. In another embodiment, the leading portion (i.e., the collected or pooled fraction of interest) of the eluate is no more than 60% of the total eluate. In a specific embodiment, the leading portion of the eluate is between 50% and 60% of the total eluate. In another specific embodiment, the leading portion of the eluate is between 50% and 55% of the total eluate. In yet another specific embodiment, the leading portion of the eluate is between 55% and 60% of the total eluate. In yet other embodiments, the leading portion of the eluate is 50%, 51%, 52%, 53%, 54%, 55%, 56%, 57%, 58%, 59%, or 60% of the total eluate. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of Factor XI (FXI) and/or Factor XIa (FXIa) in a plasma-derived immunoglobulin composition, the method comprising the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of no more than 80% of the total eluate. In a specific embodiment, the leading portion of the eluate is between 70% and 80% of the total eluate. In another specific embodiment, the leading portion of the eluate is between 60% and 80% of the total eluate. In another specific embodiment, the leading portion of the eluate is between 50% and 80% of the total eluate. In another specific embodiment, the leading portion of the eluate is between 70% and 75% of the total eluate. In yet another specific embodiment, the leading portion of the eluate is between 75% and 80% of the total eluate. In yet other embodiments, the leading portion of the eluate is 70%, 71%, 72%, 73%, 74%, 75%, 76%, 77%, 78%, 79%, or 80% of the total eluate. In another embodiment, the leading portion (i.e., the collected or pooled fraction of interest) of the eluate is no more than 70% of the total eluate. In a specific embodiment, the leading portion of the eluate is between 60% and 70% of the total eluate. In another specific embodiment, the leading portion of the eluate is between 50% and 70% of the total eluate. In another specific embodiment, the leading portion of the eluate is between 60% and 65% of the total eluate. In yet another specific embodiment, the leading portion of the eluate is between 65% and 70% of the total eluate. In yet other embodiments, the leading portion of the eluate is 60%, 61%, 62%, 63%, 64%, 65%, 66%, 67%, 68%, 69%, or 70% of the total eluate. In another embodiment, the leading portion (i.e., the collected or pooled fraction of interest) of the eluate is no more than 60% of the total eluate. In a specific embodiment, the leading portion of the eluate is between 50% and 60% of the total eluate. In another specific embodiment, the leading portion of the eluate is between 50% and 55% of the total eluate. In yet another specific embodiment, the leading portion of the eluate is between 55% and 60% of the total eluate. In yet other embodiments, the leading portion of the eluate is 50%, 51%, 52%, 53%, 54%, 55%, 56%, 57%, 58%, 59%, or 60% of the total eluate. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

d. Volume of the Total Eluate

In another embodiment particularly well suited for large-scale manufacturing of immunoglobulin compositions, the leading and lagging portions of the eluate are defined as volumes of the eluate peak relative to the size of the cation exchange column (e.g., by a set number of column volumes). By predetermining a volume of eluate to collect in the leading portion, the immunoglobulin recovery yield can be tightly controlled and reproducible. This method for defining the leading and lagging portions of the eluate is particularly useful for manufacturing processes which require a minimum step yield and for processes in which a decision is made based on weighing the cost of reduced immunoglobulin yields with the benefit of producing a composition having a reduced amidolytic and Factor XI and/or Factor XIa content. In this fashion, roughly the same yield of immunoglobulins can be reproducibly recovered from one preparation to the next, irrespective of minor variances between the manufacturing runs. As demonstrated in Examples 11 to 13, application of this collection scheme can result in a high yield recovery of an IgG immunoglobulin composition with a significantly reduced TGA and amidolytic activity content.

In one embodiment, the beginning of the leading portion is defined by a baseline absorbance. In some embodiments, collection of the leading portion begins once the absorbance of the eluate peak crosses a first threshold. In one embodiment, collection of the leading portion begins when the $OD_{280}$ of the eluate reaches at least 2.0 AU. In a specific embodiment, collection of the leading portion begins when the $OD_{280}$ of the eluate reaches at least 1.5 AU. In another specific embodiment, collection of the leading portion begins when the $OD_{280}$ of the eluate reaches at least 1.0 AU. In another specific embodiment, collection of the leading portion begins when the $OD_{280}$ of the eluate reaches at least 0.5 AU. In yet other specific embodiments, collection of the leading portion begins when the $OD_{280}$ of the eluate reaches at least 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more.

In some embodiments, once collection of the leading portion is initiated, at pre-determined number of column volumes are collected prior to switching to collection (or disposal) of the lagging portion of the eluate. In one embodiment, no more than 5 column volumes (CV) of eluate are collected in the leading portion. In another embodiment, no more than 4 CV of eluate are collected in the leading portion. In another embodiment, no more than 3 CV of eluate are collected in the leading portion. In another embodiment, no more than 2.7 CV of eluate are collected in the leading portion. In another embodiment, no more than 2.5 CV of eluate are collected in the leading portion. In another embodiment, no more than 2 CV of eluate are collected in the leading portion. In another embodiment, no more than 1 CV of eluate are collected in the leading portion. In yet other embodiments, no more than 0.5 CV, 0.6 CV, 0.7 CV, 0.8 CV, 0.9 CV, 1.0 CV, 1.1 CV, 1.2 CV, 1.3 CV, 1.4 CV, 1.5 CV, 1.6 CV, 1.7 CV, 1.8 CV, 1.9 CV, 2.0 CV, 2.1 CV, 2.2 CV, 2.3 CV, 2.4 CV, 2.5 CV, 2.6 CV, 2.7 CV, 2.8 CV, 2.9 CV, 3.0 CV, 3.1 CV, 3.2 CV, 3.3 CV, 3.4 CV, 3.5 CV, 3.6 CV, 3.7 CV, 3.8 CV, 3.9 CV, 4.0 CV, 4.1 CV, 4.2 CV, 4.3 CV, 4.4 CV, 4.5 CV, 4.6 CV, 4.7 CV, 4.8 CV, 4.9 CV, 5.0 CV, 5.1 CV, 5.2 CV, 5.3 CV, 5.4 CV, 5.5 CV, 5.6 CV, 5.7 CV, 5.8 CV, 5.9 CV, 6.0 CV, or more column volumes of eluate are collected in the leading portion.

Accordingly, in one aspect, the present invention provides a method for reducing the amount of amidolytic activity in a plasma-derived immunoglobulin composition, the method comprising the steps of: (a) binding IgG immunoglobulins and amidolytic activity (i.e., protein contaminants having amidolytic activity) onto a cation exchange resin; (b) optionally washing the cation exchange resin having proteins bound thereto with a wash buffer to remove loosely associated contaminants; (c) performing a single step elution of the IgG immunoglobulins and amidolytic activity; and (d) collecting the leading portion of the eluate separately from the lagging portion of the eluate, wherein the leading portion of the eluate consists of no more than 4 column volumes (CV) of the total eluate. In a specific embodiment, the leading portion of the eluate is between 2.5 CV and 3.0 CV of the total eluate. In another specific embodiment, the leading portion of the eluate is between 2.0 CV and 3.0 CV of the total eluate. In another specific embodiment, the leading portion of the eluate is between 2.0 CV and 3.5 CV of the total eluate. In another specific embodiment, the leading portion of the eluate is between 2.0 and 4.0 CV of the total eluate. In yet another specific embodiment, the leading portion of the eluate is between 2.5 CV and 3.5 CV of the total eluate. In yet other embodiments, the leading portion of the eluate is 0.5 CV, 0.6 CV, 0.7 CV, 0.8 CV, 0.9 CV, 1.0 CV, 1.1 CV, 1.2 CV, 1.3 CV, 1.4 CV, 1.5 CV, 1.6 CV, 1.7 CV, 1.8 CV, 1.9 CV, 2.0 CV, 2.1 CV, 2.2 CV, 2.3 CV, 2.4 CV, 2.5 CV, 2.6 CV, 2.7 CV, 2.8 CV, 2.9 CV, 3.0 CV, 3.1 CV, 3.2 CV, 3.3 CV, 3.4 CV, 3.5 CV, 3.6 CV, 3.7 CV, 3.8 CV, 3.9 CV, 4.0 CV, 4.1 CV, 4.2 CV, 4.3 CV, 4.4 CV, 4.5 CV, 4.6 CV, 4.7 CV, 4.8 CV, 4.9 CV, 5.0 CV, 5.1 CV, 5.2 CV, 5.3 CV, 5.4 CV, 5.5 CV, 5.6 CV, 5.7 CV, 5.8 CV, 5.9 CV, or 6.0 CV of the total eluate. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of Factor XI (FXI) and/or Factor XIa (FXIa) in a plasma-derived immunoglobulin composition, the method comprising the steps of: (a) contacting a plasma-derived immunoglobulin composition comprising IgG immunoglobulins and FXI and/or FXIa with a cation exchange resin disposed in a chromatography column under a first solution condition comprising a pH of no more than 6.0 and a conductivity of no more than 11 mS/cm to bind the immunoglobulins and at least a fraction of the FXI and/or FXIa to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of no more than 4 column volumes (CV) of the total eluate. In a specific embodiment, the leading portion of the eluate is between 2.5 CV and 3.0 CV of the total eluate. In another specific embodiment, the leading portion of the eluate is between 2.0 CV and 3.0 CV of the total eluate. In another specific embodiment, the leading portion of the eluate is between 2.0 CV and 3.5 CV of the total eluate. In another specific embodiment, the leading portion of the eluate is between 2.0 and 4.0 CV of the total eluate. In yet another specific embodiment, the leading portion of the eluate is between 2.5 CV and 3.5 CV of the total eluate. In yet other embodiments, the leading portion of the eluate is 0.5 CV, 0.6 CV, 0.7 CV, 0.8 CV, 0.9 CV, 1.0 CV, 1.1 CV, 1.2 CV, 1.3 CV, 1.4 CV, 1.5 CV, 1.6 CV, 1.7 CV, 1.8 CV, 1.9 CV, 2.0 CV, 2.1 CV, 2.2 CV, 2.3 CV, 2.4 CV, 2.5 CV, 2.6 CV, 2.7 CV, 2.8 CV, 2.9 CV, 3.0 CV, 3.1 CV, 3.2 CV, 3.3 CV, 3.4 CV, 3.5 CV, 3.6 CV, 3.7 CV, 3.8 CV, 3.9 CV, 4.0 CV, 4.1 CV, 4.2 CV, 4.3 CV, 4.4 CV, 4.5 CV, 4.6 CV, 4.7 CV, 4.8 CV, 4.9 CV, 5.0 CV, 5.1 CV, 5.2 CV, 5.3 CV, 5.4 CV, 5.5 CV, 5.6 CV, 5.7 CV, 5.8 CV, 5.9 CV, or 6.0 CV of the total eluate. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

IV. Reduction of Anti-Complement Activity (ACA)

In one aspect, the present disclosure provides chromatographic methods for reducing the anti-complement activity (ACA) content of a plasma-derived immunoglobulin IgG composition Likewise, the disclosure also provides plasma-derived immunoglobulin IgG compositions containing low levels of anti-complement activity (ACA) prepared according to the methods provided herein. Advantageously, the methods described herein provide plasma-derived immunoglobulin IgG compositions with improved safety profiles. Specifically, the compositions provided by these methods have reduced potential to cause adverse reactions associated with anti-complementary activity, as compared to currently manufactured immunoglobulin IgG compositions (see, for example, Buchacher A. et al., Vox Sang. 2010 April; 98(3 Pt 1):e209-18, the content of which is hereby expressly incorporated by reference in its entirety for all purposes.

A. Fractionation Methods

The present invention is based in part on the discovery that a majority of the anti-complement activity (ACA) present in a plasma-derived immunoglobulin composition elutes off of a cation exchange resin in the lagging portion of an eluate created by a step elution, while a majority of the immunoglobulin content of the fraction elutes in the leading portion of said eluate. Accordingly, by collecting the leading portion of the eluate separately from the lagging portion of the eluate, the anti-complement activity of the resulting immunoglobulin preparation is significantly reduced. Specifically, it is shown herein that ACA content is significantly reduced in immunoglobulin compositions prepared according to the methods provided herein.

Accordingly, in one embodiment, the present invention provides a method for reducing the amount of anti-complement activity (ACA) in a plasma-derived immunoglobulin composition, the method comprising the steps of: (a) binding IgG immunoglobulins and anti-complement activity (i.e., contaminants having anti-complement activity) onto a cation exchange resin; (b) optionally washing the cation exchange resin having proteins bound thereto with a wash buffer to remove loosely associated contaminants; (c) performing a single step elution of the IgG immunoglobulins and ACA; and (d) collecting the leading portion of the eluate separately from the lagging portion of the eluate, wherein the leading portion of the eluate comprises an IgG immunoglobulin composition having a reduced amount of ACA as compared to the starting composition, and the lagging portion of the eluate contains a high concentration of ACA activity. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of anti-complement activity (ACA) in a plasma-derived immunoglobulin composition, the method comprising the steps of: (a) contacting a plasma-derived immunoglobulin composition comprising IgG immunoglobulins and a first amount of ACA with a cation exchange resin disposed in a chromatography column under a first solution condition comprising a pH of no more than 6.0 and a conductivity of no more than 11 mS/cm to bind the immunoglobulins and at least a fraction of the first amount of ACA to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate comprises an IgG immunoglobulin composition having a reduced concentration of ACA, relative to the concentration of immunoglobulin IgG, as compared to the starting composition and the lagging portion of the eluate contains a high concentration of ACA, relative to the concentration of immunoglobulin IgG. In a preferred embodiment, the cation exchange resin is a weak cation exchange resin. In a specific embodiment, the weak cation exchange resin is a carboxymethyl (CM) resin. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm.

In one specific embodiment, the method comprises the steps of: (a) contacting a plasma-derived immunoglobulin composition comprising IgG immunoglobulins and a first amount of ACA with a cation exchange resin disposed in a chromatography column under a first solution condition comprising a pH between 4.8 and 5.6 and a conductivity of no more than 11 mS/cm to bind the immunoglobulins and at least a fraction of the first amount of ACA to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate comprises an IgG immunoglobulin composition having a reduced amount of ACA, relative to the amount of immunoglobulin IgG, as compared to the starting composition, and the lagging portion of the eluate contains a high amount of ACA, relative to the amount of immunoglobulin IgG. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

In one specific embodiment, the method comprises the steps of: (a) contacting a plasma-derived immunoglobulin composition comprising IgG immunoglobulins and a first amount of ACA with a cation exchange resin disposed in a chromatography column under a first solution condition comprising a pH of no more than 6.0 and a conductivity of no more than 11 mS/cm to bind the immunoglobulins and at least a fraction of the first amount of ACA to the cation exchange resin; (b) washing the resin with the immunoglobulins and ACA bound thereto with a buffer having a sufficiently low conductivity such that the immunoglobulins are not eluted from the resin and a pH between 5.1 and 5.9; (c) eluting the immunoglobulins from the cation exchange resin by contacting the cation exchange resin with an elution buffer comprising a pH of at least 7.5 and a conductivity of at least 15 mS/cm to form an eluate; and (d) collecting the leading portion of the eluate separately from the lagging portion of the eluate, wherein the leading portion of the eluate comprises an IgG immunoglobulin composition having a reduced concentration of ACA, relative to the concentration of immunoglobulin IgG, as compared to the starting composition, and the lagging portion of the eluate contains a high concentration of ACA, relative to the concentration of immunoglobulin IgG. In a specific embodiment, the pH of the wash buffer is 5.5±0.3. In another specific embodiment, the pH of the wash buffer is 5.5±0.2. In another specific embodiment, the pH of the wash buffer is 5.5±0.1. In another specific embodiment, the pH of the wash buffer is 5.5. In yet other embodiments, the pH of the wash buffer is 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

In one specific embodiment, the method comprises the steps of: (a) contacting a plasma-derived immunoglobulin composition comprising IgG immunoglobulins and a first amount of ACA with a cation exchange resin disposed in a chromatography column under a first solution condition comprising a pH of no more than 6.0 and a conductivity of no more than 11 mS/cm to bind the immunoglobulins and at least a fraction of the first amount of ACA to the cation exchange resin; (b) eluting the immunoglobulins from the cation exchange resin by contacting the cation exchange resin with an elution buffer comprising a pH of 7.8±0.4 and a conductivity of at least 20 mS/cm to form an eluate; and (c) collecting the leading portion of the eluate separately from the lagging portion of the eluate, wherein the leading portion of the eluate comprises an IgG immunoglobulin composition having a reduced concentration of ACA, relative to the concentration of immunoglobulin IgG, as compared to the starting composition, and the lagging portion of the eluate contains a high concentration of ACA, relative to the concentration of immunoglobulin IgG. In a specific embodiment, the pH of the elution buffer is 7.8±0.3. In another specific embodiment, the pH of the elution buffer is 7.8±0.2. In another specific embodiment, the pH of the elution buffer is 7.8±0.1. In another specific embodiment, the pH of the elution buffer is 7.8. In yet other embodiments, the pH of the elution buffer is 7.0, 7.1, 7.2, 7.36, 7.4, 7.5, 7.6, 7.7, 7.8, 7.9, 8.0, 8.1, 8.2, 8.3, 8.4, or 8.5. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

Generally, the starting material used for the methods provided herein includes any plasma fraction or composition comprising IgG immunoglobulin and anticomplementary activity. As such, in one embodiment, plasma is partially or wholly fractionated according to any one of the purification schemes known in the art. In a specific embodiment, plasma is fractionated to produce a Fraction I precipitate, a Fraction II precipitate, a Fraction I+II+III precipitate, a Fraction II+III precipitate, Fraction IV-1, a Kistler-Nitschmann Precipitate A, a Kistler-Nitschmann Precipitate B, or a modified precipitation thereof, which may be used as a starting material for the methods provided herein.

In a preferred embodiment, the plasma is fractionated by one or more ethanol precipitation steps. Ethanol precipitations steps may be employed to either precipitate the desired immunoglobulins out of solution, while retaining at least one non-immunoglobulin protein in the supernatant, or precipitate at least one non-immunoglobulin protein out of solution, while retaining the desired immunoglobulin in the supernatant. Methods for fractionating immunoglobulins in this fashion are well known in the art. Exemplary ethanol precipitates include, without limitation, a Fraction I precipitate, a Fraction I+II+III precipitate, a Fraction II+III precipitate, Fraction IV-1, a Kistler-Nitschmann Precipitate A, a Kistler-Nitschmann Precipitate B, and modified precipitates thereof. In a particularly preferred embodiment, immunoglobulins present in cryo-poor plasma are enriched by a four-step ethanol process, comprising a Fraction I+II+III precipitation step, an A precipitation step, a B precipitation step, and a Fraction II precipitation step.

As demonstrated herein, the advantageous features of the methods provided herein are retained when applied to large-scale manufacturing procedures. With respect to the preparation of IgG immunoglobulin compositions, large-scale manufacturing refers to processes that enrich immunoglobulins from at least 100 L of pooled plasma (e.g., cryo-poor plasma) starting material. Generally, large-scale immunoglobulin manufacturing processes will fractionate between 100 L and 20,000 L of pooled plasma per batch. In certain embodiments, a large-scale IgG immunoglobulin manufacturing process refers to the fractionation of at least 100 L of pooled plasma (e.g., cryo-poor plasma). In another embodiment, a large-scale IgG immunoglobulin manufacturing process refers to the fractionation of at least 500 L of pooled plasma (e.g., cryo-poor plasma). In another embodiment, a large-scale IgG immunoglobulin manufacturing process refers to the fractionation of at least 1,000 L of pooled plasma (e.g., cryo-poor plasma). In another embodiment, a large-scale IgG immunoglobulin manufacturing process refers to the fractionation of at least 5,000 L of pooled plasma (e.g., cryo-poor plasma). In yet another embodiment, a large-scale IgG immunoglobulin manufacturing process refers to the fractionation of at least 10,000 L of pooled plasma (e.g., cryo-poor plasma).

In one embodiment, the starting material for the methods for reducing anti-complement activity (ACA) provided herein is prepared by ethanol fractionation of pooled human plasma (e.g., cryo-poor plasma). In one specific embodiment, the ethanol fractionation includes Fraction I+II+III precipitation of cryo-poor plasma, Fraction A precipitation of a suspended Fraction I+II+III precipitate, Fraction B precipitation of a suspended Fraction A precipitate, and Fraction II precipitation of a Fraction A supernatant, as described below. In another specific embodiment, the ethanol fractionation includes Fraction I precipitation of cryo-poor plasma, Fraction II+III precipitation of a Fraction I supernatant, and Fraction II precipitation of a suspended Fraction II+III precipitate.

Generally, methods containing all combinations of the loading conditions, washing conditions, and elution conditions described above are contemplated. Furthermore, methods containing all combinations of the specific chromatographic conditions are contemplated with all possible schemes for defining and collecting the leading portion of the eluate, as described below.

1. Leading and Lagging Portions of the Cation Exchange Eluate

In one aspect, the present invention provides methods for reducing anti-complement activity (ACA), present in immunoglobulin preparations by collecting the leading portion of a cation exchange eluate. Advantageously, it is shown herein that the leading portion of an eluate formed by a single step elution of a cation exchange chromatographic step contains the majority of the desired immunoglobulin content, while the lagging portion of the eluate contains the majority of the unwanted ACA. Because the elution of immunoglobulins and ACA cannot be completely separated, a division between the leading and lagging portions of the eluate must be determined. Two major considerations may be accounted for when making this determination, namely: (i) that dependent upon how the leading and lagging portions of the eluate are defined, more or less ACA will be recovered in the leading portion—i.e., a greater portion of ACA can be separated from the immunoglobulin content when the leading portion of the eluate is defined as a smaller portion of the total eluate, and vice versa; and (ii) that dependent upon how the leading and lagging portions of the eluate are defined, greater or lesser immunoglobulin recovery yields will be present in the leading portion—i.e., a lower immunoglobulin yield will be achieved when the leading portion of the eluate is defined as a smaller portion of the total eluate, and vice versa.

Accordingly, the skilled artisan will decide as to where to draw the boundary between the leading and lagging portions of the cation exchange eluate based on their individual needs. For example, when preparing a small-scale purification for research or a specialized therapeutic purpose, the skilled artisan could maximize the separation power of the method by collecting a smaller leading portion of the eluate, while sacrificing on the final immunoglobulin yield. In contrast, when performing large-scale manufacturing (e.g., processing more than 500 L of cryo-poor plasma), the opportunity cost may dictate that a larger leading portion of the eluate is collected to increase the immunoglobulin recovery yield at the expense of a more modest reduction in the ACA of the composition.

In various embodiments, the leading and lagging portions of the eluate may be defined by various characteristics, including without limitation, the pH of the eluate, the protein yield (e.g., expressed as a percentage of the protein bound to the resin), the protein concentration (e.g., as determined by the optical density) of the eluate, the volume of eluate, and the like.

a. pH of the Eluate

As demonstrated in the examples provided herein, the beginning of the cation exchange elution step is marked by drop in the pH of the solution coming off of the column, to a pH below 5.0, despite the elution buffer having a higher pH (generally >7.0) than that of the column load and wash steps (generally 5.0-6.0). This drop in pH corresponds with the elution of an immunoglobulin IgG composition having low ACA (for example, see, Table 3, Table 11, and Table 15). At a later point in the elution, the pH of the solution coming off of the column rises sharply, to greater than 6.0-8.0. This shift in pH is concomitant with a significant increase in the ACA content of the eluate (for example, see, Table 3, Table 11, and Table 15). Thus, although a step elution is performed by the application of a single high pH elution buffer (generally greater than 7.0), the elution profile resembles a two-step elution in which IgG immunoglobulins are first eluted from the column, followed by accompanying anti-complement activity. Thus, in certain embodiments, the leading and lagging portions of the eluate are defined based on the pH of the eluate at the column outlet.

Accordingly, in one aspect, the present invention provides a method for reducing the amount of anti-complement activity (ACA) in a plasma-derived immunoglobulin composition, the method comprising the steps of: (a) binding IgG immunoglobulins and anti-complement activity (i.e., contaminants having anti-complement activity) onto a cation exchange resin; (b) optionally washing the cation exchange resin having immunoglobulin IgG and ACA bound thereto with a wash buffer to remove loosely associated contaminants; (c) performing a single step elution of the IgG immunoglobulins and ACA; and (d) collecting the leading portion of the eluate separately from the lagging portion of the eluate, wherein the leading portion of the eluate consists of the portion of the eluate having a pH of no more than 7.0. In a specific embodiment, the leading portion of the eluate consists of the portion of the eluate having a pH of no more than 6.5. In another specific embodiment, the leading portion of the eluate consists of the portion of the eluate having a pH of no more than 6.0. In another specific embodiment, the leading portion of the eluate consists of the portion of the eluate having a pH of no more than 5.5. In another specific embodiment, the leading portion of the eluate consists of the portion of the eluate having a pH of no more than 5.0. In yet other embodiments, the leading portion of the eluate consists of the portion of the eluate having a pH of no more than 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or less. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of anti-complement activity (ACA) in a plasma-derived immunoglobulin composition, the method comprising the steps of: (a) contacting a plasma-derived immunoglobulin composition comprising IgG immunoglobulins and a first amount of ACA with a cation exchange resin disposed in a chromatography column under a first solution condition comprising a pH of no more than 6.0 and a conductivity of no more than 11 mS/cm to bind the immunoglobulins and at least a fraction of the ACA to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of the portion of the eluate having a pH of no more than 7.0. In a specific embodiment, the leading portion of the eluate consists of the portion of the eluate having a pH of no more than 6.5. In another specific embodiment, the leading portion of the eluate consists of the portion of the eluate having a pH of no more than 6.0. In another specific embodiment, the leading portion of the eluate consists of the portion of the eluate having a pH of no more than 5.5. In another specific embodiment, the leading portion of the eluate consists of the portion of the eluate having a pH of no more than 5.0. In yet other embodiments, the leading portion of the eluate consists of the portion of the eluate having a pH of no more than 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or less. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

b. Absorbance of the Eluate

In yet another embodiment particularly well suited for large-scale manufacturing of immunoglobulin compositions, the leading and lagging portions of the eluate are defined by the immunoglobulin concentration eluting off of the cation exchange column. For example, during large-scale manufacturing, the immunoglobulin composition may be loaded onto the cation exchange resin at sufficiently high protein loads (e.g., >80 mg protein per mL resin) such that the peak eluate is highly concentrated. In these instances, the leading portion of the eluate can be defined as the fraction of the eluate eluting prior to the point at which the $OD_{280}$ falls below a threshold value. In this fashion, roughly the same yield of immunoglobulins can be reproducibly recovered from one preparation to the next, irrespective of minor variances between the manufacturing runs. As demonstrated in Example 9, application of this collection scheme for a large-scale manufacturing process results in a high yield recovery of an IgG immunoglobulin composition with significantly reduced anti-complement activity (ACA) content.

Accordingly, in one aspect, the present invention provides a method for reducing the amount of anti-complement activity (ACA) in a plasma-derived immunoglobulin composition, the method comprising the steps of: (a) binding IgG immunoglobulins and anti-complement activity (i.e., contaminants having anti-complement activity) onto a cation exchange resin; (b) optionally washing the cation exchange resin having proteins bound thereto with a wash buffer to remove loosely associated contaminants; (c) performing a single step elution of the IgG immunoglobulins and ACA; and (d) collecting the leading portion of the eluate separately from the lagging portion of the eluate, wherein the leading portion of the eluate consists of the portion of the eluate having an $OD_{280}$ of at least 0.5 AU. In a specific embodiment, the leading portion of the eluate consists of the portion of the eluate having an $OD_{280}$ of at least 1.0 AU. In another specific embodiment, the leading portion of the eluate consists of the portion of the eluate having an $OD_{280}$ of at least 1.5 AU. In another specific embodiment, the leading portion of the eluate consists of the portion of the eluate having an $OD_{280}$ of at least 2.0 AU. In yet other specific embodiments, the leading portion of the eluate consists of the portion of the eluate having an $OD_{280}$ of at least 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of anti-complement activity (ACA) in a plasma-derived immunoglobulin composition, the method comprising the steps of: (a) contacting a plasma-derived immunoglobulin composition comprising IgG immunoglobulins and a first amount of ACA with a cation exchange resin disposed in a chromatography column under a first solution condition comprising a pH of no more than 6.0 and a conductivity of no more than 11 mS/cm to bind the immunoglobulins and at least a fraction of the first amount of ACA to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of the portion of the eluate having an $OD_{280}$ of at least 0.5 AU. In a specific embodiment, the leading portion of the eluate consists of the portion of the eluate having an $OD_{280}$ of at least 1.0 AU. In another specific embodiment, the leading portion of the eluate consists of the portion of the eluate having an $OD_{280}$ of at least 1.5 AU. In another specific embodiment, the leading portion of the eluate consists of the portion of the eluate having an $OD_{280}$ of at least 2.0 AU. In yet other specific embodiments, the leading portion of the eluate consists of the portion of the eluate having an $OD_{280}$ of at least 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

c. Percentage of the Total Eluate

In yet another embodiment particularly well suited for large-scale manufacturing of immunoglobulin compositions, the leading and lagging portions of the eluate are defined as a percentage of the total protein content of the eluate (e.g., by volume or total protein). By predetermining the percentage of the eluate to collect in the leading portion, the immunoglobulin recovery yield can be tightly controlled. This method for defining the leading and lagging portions of the eluate is particularly useful for manufacturing processes which require a minimum step yield and for processes in which a decision is made based on weighing the cost of reduced immunoglobulin yields with the benefit of producing a composition having a reduced anti-complement activity (ACA) content. In this fashion, roughly the same yield of immunoglobulins can be reproducibly recovered from one preparation to the next, irrespective of minor variances between the manufacturing runs. As demonstrated in Example 8, application of this collection scheme can result in a high yield recovery of an IgG immunoglobulin composition with a significantly reduced anti-complement activity content.

Accordingly, in one aspect, the present invention provides a method for reducing the amount of anti-complement activity (ACA) in a plasma-derived immunoglobulin composition, the method comprising the steps of: (a) binding IgG immunoglobulins and anti-complement activity (i.e., contaminants having anti-complement activity) onto a cation exchange resin; (b) optionally washing the cation exchange resin having proteins bound thereto with a wash buffer to remove loosely associated contaminants; (c) performing a single step elution of the IgG immunoglobulins and ACA; and (d) collecting the leading portion of the eluate separately from the lagging portion of the eluate, wherein the leading portion of the eluate consists of no more than 80% of the total eluate. In a specific embodiment, the leading portion of the eluate is between 70% and 80% of the total eluate. In another specific embodiment, the leading portion of the eluate is between 60% and 80% of the total eluate. In another specific embodiment, the leading portion of the eluate is between 50% and 80% of the total eluate. In another specific embodiment, the leading portion of the eluate is between 70% and 75% of the total eluate. In yet another specific embodiment, the leading portion of the eluate is between 75% and 80% of the total eluate. In yet other embodiments, the leading portion of the eluate is 70%, 71%, 72%, 73%, 74%, 75%, 76%, 77%, 78%, 79%, or 80% of the total eluate. In another embodiment, the leading portion (i.e., the collected or pooled fraction of interest) of the eluate is no more than 70% of the total eluate. In a specific embodiment, the leading portion of the eluate is between 60% and 70% of the total eluate. In another specific embodiment, the leading portion of the eluate is between 50% and 70% of the total eluate. In another specific embodiment, the leading portion of the eluate is between 60% and 65% of the total eluate. In yet another specific embodiment, the leading portion of the eluate is between 65% and 70% of the total eluate. In yet other embodiments, the leading portion of the eluate is 60%, 61%, 62%, 63%, 64%, 65%, 66%, 67%, 68%, 69%, or 70% of the total eluate. In another embodiment, the leading portion (i.e., the collected or pooled fraction of interest) of the eluate is no more than 60% of the total eluate. In a specific embodiment, the leading portion of the eluate is between 50% and 60% of the total eluate. In another specific embodiment, the leading portion of the eluate is between 50% and 55% of the total eluate. In yet another specific embodiment, the leading portion of the eluate is between 55% and 60% of the total eluate. In yet other embodiments, the leading portion of the eluate is 50%, 51%, 52%, 53%, 54%, 55%, 56%, 57%, 58%, 59%, or 60% of the total eluate. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of anti-complement activity (ACA) in a plasma-derived immunoglobulin composition, the method comprising the steps of: (a) contacting a plasma-derived immunoglobulin composition comprising IgG immunoglobulins and a first amount of anti-complement activity (ACA) with a cation exchange resin disposed in a chromatography column under a first solution condition comprising a pH of no more than 6.0 and a conductivity of no more than 11 mS/cm to bind the immunoglobulins and at least a fraction of the first amount of ACA to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of no more than 80% of the total eluate. In a specific embodiment, the leading portion of the eluate is between 70% and 80% of the total eluate. In another specific embodiment, the leading portion of the eluate is between 60% and 80% of the total eluate. In another specific embodiment, the leading portion of the eluate is between 50% and 80% of the total eluate. In another specific embodiment, the leading portion of the eluate is between 70% and 75% of the total eluate. In yet another specific embodiment, the leading portion of the eluate is between 75% and 80% of the total eluate. In yet other embodiments, the leading portion of the eluate is 70%, 71%, 72%, 73%, 74%, 75%, 76%, 77%, 78%, 79%, or 80% of the total eluate. In another embodiment, the leading portion (i.e., the collected or pooled fraction of interest) of the eluate is no more than 70% of the total eluate. In a specific embodiment, the leading portion of the eluate is between 60% and 70% of the total eluate. In another specific embodiment, the leading portion of the eluate is between 50% and 70% of the total eluate. In another specific embodiment, the leading portion of the eluate is between 60% and 65% of the total eluate. In yet another specific embodiment, the leading portion of the eluate is between 65% and 70% of the total eluate. In yet other embodiments, the leading portion of the eluate is 60%, 61%, 62%, 63%, 64%, 65%, 66%, 67%, 68%, 69%, or 70% of the total eluate. In another embodiment, the leading portion (i.e., the collected or pooled fraction of interest) of the eluate is no more than 60% of the total eluate. In a specific embodiment, the leading portion of the eluate is between 50% and 60% of the total eluate. In another specific embodiment, the leading portion of the eluate is between 50% and 55% of the total eluate. In yet another specific embodiment, the leading portion of the eluate is between 55% and 60% of the total eluate. In yet other embodiments, the leading portion of the eluate is 50%, 51%, 52%, 53%, 54%, 55%, 56%, 57%, 58%, 59%, or 60% of the total eluate. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

d. Volume of the Total Eluate

In another embodiment particularly well suited for large-scale manufacturing of immunoglobulin compositions, the leading and lagging portions of the eluate are defined as volumes of the eluate peak relative to the size of the cation exchange column (e.g., by a set number of column volumes). By predetermining a volume of eluate to collect in the leading portion, the immunoglobulin recovery yield can be tightly controlled and reproducible. This method for defining the leading and lagging portions of the eluate is particularly useful for manufacturing processes which require a minimum step yield and for processes in which a decision is made based on weighing the cost of reduced immunoglobulin yields with the benefit of producing a composition having a reduced anti-complement activity (ACA) content. In this fashion, roughly the same yield of immunoglobulins can be reproducibly recovered from one preparation to the next, irrespective of minor variances between the manufacturing runs. As demonstrated in Examples 11 to 13, application of this collection scheme can result in a high yield recovery of an IgG immunoglobulin composition with reduced anti-complement activity content.

In one embodiment, the beginning of the leading portion is defined by a baseline absorbance. In some embodiments, collection of the leading portion begins once the absorbance of the eluate peak crosses a first threshold. In one embodiment, collection of the leading portion begins when the $OD_{280}$ of the eluate reaches at least 0.5 AU. In a specific embodiment, collection of the leading portion begins when the $OD_{280}$ of the eluate reaches at least 1.0 AU. In another specific embodiment, collection of the leading portion begins when the $OD_{280}$ of the eluate reaches at least 1.5 AU. In another specific embodiment, collection of the leading portion begins when the $OD_{280}$ of the eluate reaches at least 2.0 AU. In yet other specific embodiments, collection of the leading portion begins when the $OD_{280}$ of the eluate reaches at least 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more.

In some embodiments, once collection of the leading portion is initiated, at pre-determined number of column volumes are collected prior to switching to collection (or disposal) of the lagging portion of the eluate. In one embodiment, no more than 5 column volumes (CV) of eluate are collected in the leading portion. In another embodiment, no more than 4 CV of eluate are collected in the leading portion. In another embodiment, no more than 3 CV of eluate are collected in the leading portion. In another embodiment, no more than 2.7 CV of eluate are collected in the leading portion. In another embodiment, no more than 2.5 CV of eluate are collected in the leading portion. In another embodiment, no more than 2 CV of eluate are collected in the leading portion. In another embodiment, no more than 1 CV of eluate are collected in the leading portion. In yet other embodiments, no more than 0.5 CV, 0.6 CV, 0.7 CV, 0.8 CV, 0.9 CV, 1.0 CV, 1.1 CV, 1.2 CV, 1.3 CV, 1.4 CV, 1.5 CV, 1.6 CV, 1.7 CV, 1.8 CV, 1.9 CV, 2.0 CV, 2.1 CV, 2.2 CV, 2.3 CV, 2.4 CV, 2.5 CV, 2.6 CV, 2.7 CV, 2.8 CV, 2.9 CV, 3.0 CV, 3.1 CV, 3.2 CV, 3.3 CV, 3.4 CV, 3.5 CV, 3.6 CV, 3.7 CV, 3.8 CV, 3.9 CV, 4.0 CV, 4.1 CV, 4.2 CV, 4.3 CV, 4.4 CV, 4.5 CV, 4.6 CV, 4.7 CV, 4.8 CV, 4.9 CV, 5.0 CV, 5.1 CV, 5.2 CV, 5.3 CV, 5.4 CV, 5.5 CV, 5.6 CV, 5.7 CV, 5.8 CV, 5.9 CV, 6.0 CV, or more column volumes of eluate are collected in the leading portion.

Accordingly, in one aspect, the present invention provides a method for reducing the amount of amidolytic activity in a plasma-derived immunoglobulin composition, the method comprising the steps of: (a) binding IgG immunoglobulins and anti-complement activity (i.e., contaminants having anti-complement activity) onto a cation exchange resin; (b) optionally washing the cation exchange resin having proteins bound thereto with a wash buffer to remove loosely associated contaminants; (c) performing a single step elution of the IgG immunoglobulins and ACA; and (d) collecting the leading portion of the eluate separately from the lagging portion of the eluate, wherein the leading portion of the eluate consists of no more than 4 column volumes (CV) of the total eluate. In a specific embodiment, the leading portion of the eluate is between 2.5 CV and 3.0 CV of the total eluate. In another specific embodiment, the leading portion of the eluate is between 2.0 CV and 3.0 CV of the total eluate. In another specific embodiment, the leading portion of the eluate is between 2.0 CV and 3.5 CV of the total eluate. In another specific embodiment, the leading portion of the eluate is between 2.0 and 4.0 CV of the total eluate. In yet another specific embodiment, the leading portion of the eluate is between 2.5 CV and 3.5 CV of the total eluate. In yet other embodiments, the leading portion of the eluate is 0.5 CV, 0.6 CV, 0.7 CV, 0.8 CV, 0.9 CV, 1.0 CV, 1.1 CV, 1.2 CV, 1.3 CV, 1.4 CV, 1.5 CV, 1.6 CV, 1.7 CV, 1.8 CV, 1.9 CV, 2.0 CV, 2.1 CV, 2.2 CV, 2.3 CV, 2.4 CV, 2.5 CV, 2.6 CV, 2.7 CV, 2.8 CV, 2.9 CV, 3.0 CV, 3.1 CV, 3.2 CV, 3.3 CV, 3.4 CV, 3.5 CV, 3.6 CV, 3.7 CV, 3.8 CV, 3.9 CV, 4.0 CV, 4.1 CV, 4.2 CV, 4.3 CV, 4.4 CV, 4.5 CV, 4.6 CV, 4.7 CV, 4.8 CV, 4.9 CV, 5.0 CV, 5.1 CV, 5.2 CV, 5.3 CV, 5.4 CV, 5.5 CV, 5.6 CV, 5.7 CV, 5.8 CV, 5.9 CV, or 6.0 CV of the total eluate. In a preferred embodiment, the cation exchange resin is a weak cation exchange resin. In a specific embodiment, the weak cation exchange resin is a carboxymethyl (CM) resin.

In a specific embodiment, the invention provides a method for reducing the amount of anti-complement activity (ACA) in a plasma-derived immunoglobulin composition, the method comprising the steps of: (a) contacting a plasma-derived immunoglobulin composition comprising IgG immunoglobulins and a first amount of ACA with a cation exchange resin disposed in a chromatography column under a first solution condition comprising a pH of no more than 6.0 and a conductivity of no more than 11 mS/cm to bind the immunoglobulins and at least a fraction of the first amount of ACA to the cation exchange resin; (b) eluting the immunoglobulins from the cation exchange resin by contacting the cation exchange resin with an elution buffer comprising a pH of at least 7.5 and a conductivity of at least 15 mS/cm to form an eluate; and (c) collecting the leading portion of the eluate separately from the lagging portion of the eluate, wherein the leading portion of the eluate consists of no more than 4 column volumes (CV) of the total eluate. In a specific embodiment, the leading portion of the eluate is between 2.5 CV and 3.0 CV of the total eluate. In another specific embodiment, the leading portion of the eluate is between 2.0 CV and 3.0 CV of the total eluate. In another specific embodiment, the leading portion of the eluate is between 2.0 CV and 3.5 CV of the total eluate. In another specific embodiment, the leading portion of the eluate is between 2.0 and 4.0 CV of the total eluate. In yet another specific embodiment, the leading portion of the eluate is between 2.5 CV and 3.5 CV of the total eluate. In yet other embodiments, the leading portion of the eluate is 0.5 CV, 0.6 CV, 0.7 CV, 0.8 CV, 0.9 CV, 1.0 CV, 1.1 CV, 1.2 CV, 1.3 CV, 1.4 CV, 1.5 CV, 1.6 CV, 1.7 CV, 1.8 CV, 1.9 CV, 2.0 CV, 2.1 CV, 2.2 CV, 2.3 CV, 2.4 CV, 2.5 CV, 2.6 CV, 2.7 CV, 2.8 CV, 2.9 CV, 3.0 CV, 3.1 CV, 3.2 CV, 3.3 CV, 3.4 CV, 3.5 CV, 3.6 CV, 3.7 CV, 3.8 CV, 3.9 CV, 4.0 CV, 4.1 CV, 4.2 CV, 4.3 CV, 4.4 CV, 4.5 CV, 4.6 CV, 4.7 CV, 4.8 CV, 4.9 CV, 5.0 CV, 5.1 CV, 5.2 CV, 5.3 CV, 5.4 CV, 5.5 CV, 5.6 CV, 5.7 CV, 5.8 CV, 5.9 CV, or 6.0 CV of the total eluate. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

V. Preparation of Cryo-Poor Plasma

The starting material used for the preparation of concentrated IgG compositions generally consists of either recovered plasma (i.e., plasma that has been separated from whole blood ex vivo) or source plasma (i.e., plasma collected via plasmapheresis). The purification process typically starts with thawing previously frozen pooled plasma, which has already been assayed for safety and quality considerations. Thawing is typically carried out at a temperature no higher than 6° C., preferably between −1° C. and 6° C. After complete thawing of the frozen plasma at low temperature, centrifugation is performed in the cold (e.g., ≤6° C., preferably 2.5±3.5° C.) to separate solid cryo-precipitates from the liquid supernatant. Alternatively, the separation step can be performed by filtration rather than centrifugation. The liquid supernatant (also referred to as "cryo-poor plasma," after cold-insoluble proteins removed by centrifugation from fresh thawed plasma) is then processed in the next step. Various additional steps can be taken at this juncture for the isolation of factor eight inhibitor bypass activity (FEIBA), Factor IX-complex, Factor VII-concentrate, or Antithrombin III-complex. For example, one or more blood factors may be adsorbed from the cryo-poor plasma prior to further enriching the immunoglobulin-containing solution.

VI. Fractionation of Cryo-Poor Plasma

In order to prepare an IgG immunoglobulin composition, cryo-poor plasma is commonly fractionated to separate the desired immunoglobulins from other proteins and impurities present. Many methods for the fractionation of plasma are known in the art, including alcohol (e.g., ethanol) fractionation, polymer (e.g., PEG) precipitation, fatty acid and ester (e.g., caprylate) precipitation, chromatography, and the like. Examples of these fractionation processes include, without limitation, Cohn fractionations (J. Am. Chem. Soc., 1946, 68(3): 459-475; J. Am. Chem. Soc. 72:465-474 (1950)), Oncley fractionations (J. Am. Chem. Soc., 1949, 71(2): 541-550), Deutsch purifications (J. Biol. Chem. 164:109-118), Hoppe purifications (Munch Med Wochenschr 1967 (34): 1749-1752), Falksveden purifications (Swedish Patent No. 348942), Falksveden and Lundblad purifications (Methods of Plasma Protein Fractionation 1980), Lebing purifications (Vox Sang 2003 (84):193-201), Tanaka purifications (Braz J Med Biol Res 2000 (33)37-30)), Teschner purifications (Vox Sang, 2007 (92):42-55), Nitschmann fractionations (Helv. Chim. Acta 37:866-873), Kistler/Nitschmann fractionations (Vox Sang. 7:414-424 (1962)), Barundern purifications (Vox Sang. 7:157-74 (1962)), Koblet purifications (Vox Sang. 13:93-102 (1967)) a purification procedure disclosed in U.S. Pat. No. 5,122,373 or 5,177,194, modified procedures thereof, and similar or equivalent purification procedures known in the art, the disclosures of which are hereby incorporated by reference in their entireties, for all purposes.

Generally, the methods provided herein are compatible with any of the purification schemes outlined above. As such, in one embodiment, cryo-poor plasma is partially or wholly fractionated according to any one of the purification schemes mentioned above. In a specific embodiment, cryo-poor plasma is fractionated according to one or more fractionation steps disclosed in the teachings described above, to produce a fractionation intermediate composition. In a more specific embodiment, cryo-poor plasma is fractionated to produce a Fraction I precipitate, a Fraction II precipitate, a Fraction I+II+III precipitate, a Fraction II+III precipitate, Fraction IV-1, a Kistler-Nitschmann Precipitate A, a Kistler-Nitschmann Precipitate B, or a modified precipitation thereof.

In a preferred embodiment, the cryo-poor plasma is fractionated by one or more ethanol precipitation steps. Ethanol precipitations steps may be employed to either precipitate the desired immunoglobulins out of solution, while retaining at least one non-immunoglobulin protein in the supernatant, or precipitate at least one non-immunoglobulin protein out of solution, while retaining the desired immunoglobulin in the supernatant. Methods for fractionating immunoglobulins in this fashion are well known in the art. Exemplary ethanol precipitates include, without limitation, a Fraction I precipitate, a Fraction I+II+III precipitate, a Fraction II+III precipitate, Fraction IV-1, a Kistler-Nitschmann Precipitate A, a Kistler-Nitschmann Precipitate B, and modified precipitates thereof. In a particularly preferred embodiment, immunoglobulins present in cryo-poor plasma are enriched by a four-step ethanol process, comprising a Fraction I+II+III precipitation step, an A precipitation step, a B precipitation step, and a Fraction II precipitation step, as described below.

VII. Exemplary Fractionation Schemes

Although the skilled artisan will appreciate that many different starting materials (e.g., different plasma fractions) may be used to perform the methods provided herein for reducing amidolytic activity (e.g., Factor XI and/or Factor XIa content) and/or anti-complement activity (ACA), an exemplary fractionation scheme is provided below. The exemplary fractionation scheme employs four ethanol precipitation reactions to prepare a Fraction II precipitation which may be re-suspended and subsequently used as starting material for the methods provided herein. The resulting enriched IgG immunoglobulin composition may be further enriched by downstream processing using techniques such as anion exchange chromatography, ultra-/diafiltration, viral inactivation and/or removal steps, and other enrichment steps well known in the art.

Accordingly, in one embodiment, the present invention provides a method for manufacturing an IgG immunoglobulin composition, the method comprising the steps of: (a) providing a cryo-poor plasma fraction; (b) precipitating immunoglobulins from the cryo-poor plasma fraction in a first precipitation reaction by admixing ethanol with the cryo-poor plasma fraction at a final concentration of between 17% and 23% (v/v) at a pH between 6.5 and 7.3 and temperature between −8° C. to −2° C., thereby forming a first precipitate and a first supernatant; (c) resuspending immunoglobulins present in the first precipitate, thereby forming a first suspension; (d) precipitating immunoglobulins from the first suspension in a second precipitation reaction by admixing ethanol with the cryo-poor plasma fraction at a final concentration of between 17% and 23% (v/v) at a pH between 6.8 and 7.6 and temperature between −8° C. to −2° C., thereby forming a second precipitate and a second supernatant; (e) resuspending immunoglobulins present in the second precipitate, thereby forming a second suspension; (f) precipitating immunoglobulins from the second suspension in a third precipitation reaction by admixing ethanol with the cryo-poor plasma fraction at a final concentration of between 14% and 20% (v/v) at a pH between 5.0 and 5.8 and temperature between −8° C. to −2° C., thereby forming a third precipitate and a third supernatant; (g) precipitating immunoglobulins from the third supernatant in a fourth precipitation reaction by admixing ethanol with the cryo-poor plasma fraction at a final concentration of between 22% and 28% (v/v) at a pH between 6.7 and 7.5 and temperature between −8° C. to −2° C., thereby forming a fourth precipitate and a fourth supernatant; (h) re-suspending the fourth precipitate to form a third suspension; (i) contacting the third suspension with a cation exchange resin disposed in a chromatography column under a first solution condition comprising a pH of no more than 6.0 and a conductivity of no more than 11 mS/cm to bind the IgG immunoglobulins and at least one of: (i) a fraction of the FXI and/or FXIa, and (ii) a first amount of anti-complement activity (ACA), to the cation exchange resin; (j) eluting the IgG immunoglobulins from the cation exchange resin by contacting the cation exchange resin with an elution buffer comprising a pH of at least 7.5 and a conductivity of at least 15 mS/cm to form an eluate comprising a leading portion and lagging portion; and (k) collecting the leading portion of the eluate separately from the lagging portion of the eluate. In a specific embodiment, the pH of the first solution condition is 5.2±0.3. In another specific embodiment, the pH of the first solution condition is 5.2±0.2. In another specific embodiment, the pH of the first solution condition is 5.2±0.1. In yet another specific embodiment, the pH of the first solution condition is 5.2. In yet other embodiments, the pH of the first solution condition is 4.8, 4.9, 5.0, 5.1, 5.2, 5.3, 5.4, 5.5, 5.6, 5.7, 5.8, 5.9, or 6.0. In another specific embodiment, the elution buffer comprises a conductivity of at least 20 mS/cm. In yet another specific embodiment, the elution buffer comprises a conductivity of at least 22 mS/cm. In yet another specific embodiment, the elution buffer comprises a conductivity of at least 25 mS/cm. In a preferred embodiment, the cation exchange resin is a weak cation exchange resin. In a specific embodiment, the weak cation exchange resin is a carboxymethyl (CM) resin.

A. Upstream Fractionation Scheme I

In a first exemplary upstream purification scheme, plasma containing immunoglobulin IgG is subjected to alcohol fractionation (e.g., ethanol fractionation) as described below. In one embodiment, this first upstream fractionation scheme includes a Fraction I+II+III precipitation step, a Fraction A precipitation step, and a Fraction B precipitation step prior to the Fraction II precipitation step which ultimately provides the starting material for cation exchange chromatographic methods provided herein for the reduction of amidolytic activity (e.g., Factor XI/XIa) and/or anti-complement activity (ACA).

Methods containing all combinations of precipitating conditions (e.g., ethanol concentration, pH, temperature, separation technique) for each of the Fraction I+II+III, Fraction A, Fraction B, and Fraction II precipitation steps described below are contemplated. Furthermore, methods containing all combinations of the specific precipitation conditions are contemplated with all possible schemes for defining and collecting the leading portion of the eluate, as described below.

1. Fraction I+II+III Precipitation

In one embodiment, a Fraction I+II+III precipitation is formed by adding ethanol to cryo-poor plasma at final concentration of between 17% and 23% (v/v) at a pH between 6.5 and 7.3. The mixture is then incubated while stirring at between −8° C. to −2° C. The resulting Fraction I+II+III precipitate can be separated from the Fraction I+II+III supernatant by centrifugation or filtration of the mixture, which is generally performed in the cold. The majority of the immunoglobulin content is present in the Fraction I+II+III precipitate, which can be re-suspended and further enriched.

In one specific embodiment, the final concentration of ethanol in the Fraction I+II+III precipitation step is 20±3% (v/v). In another embodiment, the final concentration of ethanol is 20±2% (v/v). In another embodiment, the final concentration of ethanol is 20±1% (v/v). In yet another embodiment, the final concentration of ethanol is 20% (v/v). In yet other embodiments, the final concentration of ethanol is 17%, 18%, 19%, 20%, 21%, 22%, or 23% (v/v).

In one specific embodiment, the pH of the Fraction I+II+III precipitation step is 6.9±0.4. In another embodiment, the pH of the Fraction I+II+III precipitation step is 6.9±0.3. In another embodiment, the pH of the Fraction I+II+III precipitation step is 6.9±0.2. In another embodiment, the pH of the Fraction I+II+III precipitation step is 6.9±0.1. In yet another embodiment, the pH of the Fraction I+II+III precipitation step is 6.9. In yet other embodiments, the pH of the Fraction I+II+III precipitation step is 6.5, 6.6, 6.7, 6.8, 6.9, 7.0, 7.1, 7.2, or 7.3.

In one specific embodiment, the temperature of the Fraction I+II+III precipitation step is −5±3° C. In another embodiment, the temperature of the Fraction I+II+III precipitation step is −5±2° C. In another embodiment, the temperature of the Fraction I+II+III precipitation step is −5±1° C. In yet another embodiment, the temperature of the Fraction I+II+III precipitation step is −5° C. In yet other embodiments, the temperature of the Fraction I+II+III precipitation step is −8° C., −7° C., −6° C., −5° C., −4° C., −3° C., or −2° C.

In a specific embodiment, the cryo-poor plasma is adjusted to a pH of 6.9±0.2 and an alcohol concentration calculated to be 20% (v/v) by the addition of a re-suspension buffer containing sodium acetate trihydrate, glacial acetic acid, and water for injection (pH 4.0) and denatured ethyl alcohol (formula SDA-3A). The buffer is added with the required amount of alcohol with thorough mixing. The alcohol is cooled to a temperature of −15° C. or colder before addition to cryo-poor plasma. The buffer and alcohol are added to the plasma while the suspension tank is cooled to a temperature of −5±2° C. After addition is completed, the pH of the solution is checked and adjusted to 6.9±0.2 if required with pH 4.0 buffer or sodium bicarbonate solution. The resulting Fraction I+II+III suspension is then centrifuged to separate the precipitate from the supernatant.

2. Fraction A Precipitation

To further enrich the IgG content and purity, in one embodiment, a Fraction I+II+III precipitate is re-suspended and a second precipitation step (Fraction A precipitation) is performed. Fraction A precipitation is performed by adding ethanol to the Fraction I+II+III suspension to a final concentration of between 17% and 23% (v/v) at a pH between 6.8 and 7.6. The mixture is then incubated while stirring at between −8° C. to −2° C. The resulting Fraction A precipitate can be separated from the Fraction A supernatant by centrifugation or filtration of the mixture, which is generally performed in the cold. The majority of the immunoglobulin content is present in the Fraction A precipitate, which can be re-suspended and further enriched.

In one specific embodiment, the final concentration of ethanol in the Fraction A precipitation step is 20±3% (v/v). In another embodiment, the final concentration of ethanol is 20±2% (v/v). In another embodiment, the final concentration of ethanol is 20±1% (v/v). In yet another embodiment, the final concentration of ethanol is 20% (v/v). In yet other embodiment, the final concentration of ethanol is 17%, 18%, 19%, 20%, 21%, 22%, or 23% (v/v).

In one specific embodiment, the pH of the Fraction A precipitation step is 7.2±0.4. In another embodiment, the pH of the Fraction A precipitation step is 7.2±0.3. In another embodiment, the pH of the Fraction A precipitation step is 7.2±0.2. In another embodiment, the pH of the Fraction A precipitation step is 7.2±0.1. In yet another embodiment, the pH of the Fraction A precipitation step is 7.2. In yet other embodiments, the pH of the Fraction A precipitation step is 6.8, 6.9, 7.0, 7.1, 7.2, 7.3, 7.4, 7.5, or 7.6.

In one specific embodiment, the temperature of the Fraction A precipitation step is −5±3° C. In another embodiment, the temperature of the Fraction A precipitation step is −5±2° C. In another embodiment, the temperature of the Fraction A precipitation step is −5±1° C. In yet another embodiment, the temperature of the Fraction A precipitation step is −5° C. In yet other embodiments, the temperature of the Fraction A precipitation step is −8° C., −7° C., −6° C., −5° C., −4° C., −3° C., or −2° C.

In one specific embodiment, Fraction I+II+III precipitate is suspended in cold re-suspension buffer containing sodium acetate trihydrate, glacial acetic acid, and water for injection (pH 4.0) and mixed. The suspension is diluted with WFI to achieve a calculated protein concentration of 1.0±0.3% (w/v). Stirring is continued until the suspension is homogeneous. The solution is adjusted to a pH of 7.2±0.2 with buffer (pH 4.0) or with 0.25 M disodium phosphate and brought to a calculated alcohol concentration of 20% (v/v). The alcohol is cooled to a temperature of −15° C. or colder before addition to the solution. The cold alcohol is added while the tank is cooled to −5±2° C. After addition is completed, the pH of the suspension is checked and adjusted to 7.2±0.2 if required. The precipitate formed (referred to as Fraction A precipitate) is then filtered to separate the precipitate from the supernatant.

3. Fraction B Precipitation

To further enrich the IgG content and purity, in one embodiment, a Fraction A precipitate is re-suspended and a third precipitation step (Fraction B precipitation) is performed. Fraction B precipitation is performed by adding ethanol to the Fraction A suspension to a final concentration of between 14% and 20% (v/v) at a pH between 5.0 and 5.8. The mixture is then incubated while stirring at between −8° C. to −2° C. The resulting Fraction B precipitate can be separated from the Fraction B supernatant by centrifugation or filtration of the mixture, which is generally performed in the cold. The majority of the immunoglobulin content is present in the Fraction B supernatant, which can be recovered and further enriched.

In one specific embodiment, the final concentration of ethanol in the Fraction B precipitation step is 17±3% (v/v). In another embodiment, the final concentration of ethanol is 17±2% (v/v). In another embodiment, the final concentration of ethanol is 17±1% (v/v). In yet another embodiment, the final concentration of ethanol is 17% (v/v). In yet other embodiment, the final concentration of ethanol is 14%, 15%, 16%, 17%, 18%, 19%, or 20% (v/v).

In one specific embodiment, the pH of the Fraction B precipitation step is 5.4±0.4. In another embodiment, the pH of the Fraction B precipitation step is 5.4±0.3. In another embodiment, the pH of the Fraction B precipitation step is 5.4±0.2. In another embodiment, the pH of the Fraction B precipitation step is 5.4±0.1. In yet another embodiment, the pH of the Fraction B precipitation step is 5.4. In yet other embodiments, the pH of the Fraction B precipitation step is 5.0, 5.1, 5.2, 5.3, 5.4, 5.5, 5.6, 5.7, or 5.8.

In one specific embodiment, the temperature of the Fraction A precipitation step is −5±3° C. In another embodiment, the temperature of the Fraction A precipitation step is −5±2° C. In another embodiment, the temperature of the Fraction A precipitation step is −5±1° C. In yet another embodiment, the temperature of the Fraction A precipitation step is −5° C. In yet other embodiments, the temperature of the Fraction A precipitation step is −8° C., −7° C., −6° C., −5° C., −4° C., −3° C., or −2° C.

In a specific embodiment, a Fraction A precipitate is suspended in cold water for injection (WFI) and stirred for at least one hour. When the precipitate is thoroughly suspended, a buffer containing sodium acetate is added. Stirring continues until the suspension is homogenous. The pH is adjusted to 5.4±0.2 with pH 4.0 buffer (109 g/L sodium acetate trihydrate, 240 g/L glacial acetic acid, and WFI) or 0.25 M disodium phosphate. The suspension is diluted with cold WFI calculated to achieve a protein concentration of 1.2±0.3% (w/v). Stirring continues until the suspension is homogeneous. The alcohol content is brought to a concentration calculated to be 17% (v/v) by adding alcohol pre-chilled to −15° C. or less. The cold alcohol is added while the tank is cooled to −5±2° C. If necessary, the pH is readjusted to 5.4±0.2 with 4.0 pH buffer or 0.25 M disodium phosphate. The precipitate formed, Fraction B precipitate, is separated by filtration using a depth filter. The Fraction B filtrate (i.e., supernatant) is recovered for further enrichment.

B. Upstream Fractionation Scheme II

In a second exemplary upstream purification scheme, plasma containing immunoglobulin IgG is subjected to alcohol fractionation (e.g., ethanol fractionation) as described below. In one embodiment, this first upstream fractionation scheme includes a Fraction I precipitation step and a Fraction II+III precipitation step prior to the Fraction II precipitation step which ultimately provides the starting material for cation exchange chromatographic methods provided herein for the reduction of amidolytic activity (e.g., Factor XI/XIa) and/or anti-complement activity (ACA).

Methods containing all combinations of precipitating conditions (e.g., ethanol concentration, pH, temperature, separation technique) for each of the Fraction I, Fraction II+III, and Fraction II precipitation steps described below are contemplated. Furthermore, methods containing all combinations of the specific precipitation conditions are contemplated with all possible schemes for defining and collecting the leading portion of the eluate, as described below.

1. Fraction I Precipitation

In one embodiment, a Fraction I precipitation is formed by adding ethanol to cryo-poor plasma at final concentration of from 6% to 10% (v/v) at a pH from 6.7 and 7.3. The mixture is then incubated while stirring at from −4° C. to 2° C. The resulting Fraction I precipitate can be separated from the Fraction I supernatant by centrifugation or filtration of the mixture, which is generally performed in the cold. The majority of the immunoglobulin content is present in the Fraction I supernatant, which can be recovered and further enriched.

In one specific embodiment, the final concentration of ethanol in the Fraction I precipitation step is 8±2% (v/v). In another embodiment, the final concentration of ethanol is 8±1% (v/v). In yet another embodiment, the final concentration of ethanol is 8% (v/v). In yet other embodiment, the final concentration of ethanol is 6%, 7%, 8%, 9%, or 10% (v/v).

In one specific embodiment, the pH of the Fraction I precipitation step is 7.0±0.4. In another embodiment, the pH of the Fraction I precipitation step is 7.0±0.3. In another embodiment, the pH of the Fraction I precipitation step is 7.0±0.2. In another embodiment, the pH of the Fraction I precipitation step is 7.0±0.1. In yet another embodiment, the pH of the Fraction I precipitation step is 7.0. In yet other embodiments, the pH of the Fraction I precipitation step is 6.7, 6.8, 6.9, 7.0, 7.1, 7.2, or 7.3.

In one specific embodiment, the temperature of the Fraction I precipitation step is −1±3° C. In another embodiment, the temperature of the Fraction I precipitation step is −1±2° C. In another embodiment, the temperature of the Fraction I precipitation step is −1±1° C. In yet another embodiment, the temperature of the Fraction I precipitation step is −1° C. In yet other embodiments, the temperature of the Fraction I precipitation step is −4° C., −3° C., −2° C., −1° C., 0° C., 1° C., or 2° C.

In a specific embodiment, the cryo-poor plasma is adjusted to a pH of 7.0±0.1 and an alcohol concentration calculated to be 8% (v/v). The solutions used to adjust the pH and alcohol concentrations are added with thorough mixing. The temperature of the precipitation reaction is lowered and held throughout at −1±1° C. The resulting Fraction I suspension is then centrifuged or filtered to separate the precipitate from the supernatant.

2. Fraction II+III Precipitation

To further enrich the IgG content and purity, in one embodiment, a Fraction I supernatant is used as the material for a second precipitation step (Fraction II+III precipitation). Fraction II+III precipitation is performed by adding ethanol to the Fraction I supernatant to a final concentration of from 22% to 28% (v/v) at a pH between 6.7 and 7.3. The mixture is then incubated while stirring at between −10° C. to −4° C. The resulting Fraction II+III precipitate can be separated from the Fraction II+III supernatant by centrifugation or filtration of the mixture, which is generally performed in the cold. The majority of the immunoglobulin content is present in the Fraction II+III precipitate, which can be re-suspended and further enriched.

In one specific embodiment, the final concentration of ethanol in the Fraction II+III precipitation step is 25±3% (v/v). In another embodiment, the final concentration of ethanol is 25±2% (v/v). In another embodiment, the final concentration of ethanol is 25±1% (v/v). In yet another embodiment, the final concentration of ethanol is 25% (v/v). In yet other embodiment, the final concentration of ethanol is 22%, 23%, 24%, 25%, 26%, 27%, or 28% (v/v).

In one specific embodiment, the pH of the Fraction II+III precipitation step is 7.0±0.4. In another embodiment, the pH of the Fraction II+III precipitation step is 7.0±0.3. In another embodiment, the pH of the Fraction II+III precipitation step is 7.0±0.2. In another embodiment, the pH of the Fraction II+III precipitation step is 7.0±0.1. In yet another embodiment, the pH of the Fraction II+III precipitation step is 7.0. In yet other embodiments, the pH of the Fraction II+III precipitation step is 6.6, 6.7, 6.8, 6.9, 7.0, 7.1, 7.2, 7.3, or 7.4.

In one specific embodiment, the temperature of the Fraction II+III precipitation step is −7±3° C. In another embodiment, the temperature of the Fraction II+III precipitation step is −7±2° C. In another embodiment, the temperature of the Fraction II+III precipitation step is −7±1° C. In yet another embodiment, the temperature of the Fraction II+III precipitation step is −7° C. In yet other embodiments, the temperature of the Fraction II+III precipitation step is −10° C., −9° C., −8° C., −7° C., −6° C., −5° C., or −4° C.

In a specific embodiment, the Fraction I supernatant is adjusted to a pH of 7.0±0.1 and an alcohol concentration calculated to be 25% (v/v). The solutions used to adjust the pH and alcohol concentrations are added with thorough mixing. The temperature of the precipitation reaction is lowered and held throughout at −6±2° C. The resulting Fraction II+III suspension is then centrifuged or filtered to separate the precipitate from the supernatant.

C. Fraction II Precipitation

To further enrich the IgG content and purity, in one embodiment, a fourth (following upstream fractionation scheme I) or third (following upstream fractionation scheme II) alcohol precipitation step (Fraction II precipitation) is performed. Fraction II precipitation is performed by adjusting the pH of a Fraction B filtrate or Fraction II+III precipitate suspension to between 6.7 and 7.5 and adding ethanol to a final concentration of between 22% and 28% (v/v). The mixture is then incubated while stirring at between −13° C. to −2° C. The resulting Fraction II precipitate can be separated from the Fraction B supernatant by centrifugation or filtration of the mixture, which is generally performed in the cold. The majority of the immunoglobulin content is present in the Fraction II precipitate, which can be re-suspended and further enriched.

In one specific embodiment, the final concentration of ethanol in the Fraction II precipitation step is 25±3% (v/v). In another embodiment, the final concentration of ethanol is 25±2% (v/v). In another embodiment, the final concentration of ethanol is 25±1% (v/v). In yet another embodiment, the final concentration of ethanol is 25% (v/v). In yet other embodiment, the final concentration of ethanol is 22%, 23%, 24%, 25%, 26%, 27%, or 28% (v/v).

In one specific embodiment, the pH of the Fraction II precipitation step is 7.1±0.4. In another embodiment, the pH of the Fraction II precipitation step is 7.1±0.3. In another embodiment, the pH of the Fraction II precipitation step is 7.1±0.2. In another embodiment, the pH of the Fraction II precipitation step is 7.1±0.1. In yet another embodiment, the pH of the Fraction II precipitation step is 7.1. In yet other embodiments, the pH of the Fraction II precipitation step is 6.7, 6.8, 6.9, 7.0, 7.1, 7.2, 7.3, 7.4, or 7.5.

In one specific embodiment, the temperature of the Fraction II precipitation step is −5±3° C. In another embodiment, the temperature of the Fraction II precipitation step is −5±2° C. In another embodiment, the temperature of the Fraction II precipitation step is −5±1° C. In yet another embodiment, the temperature of the Fraction II precipitation step is −5° C. In another specific embodiment, the temperature of the Fraction II precipitation step is −10±3° C. In another embodiment, the temperature of the Fraction II precipitation step is −10±2° C. In another embodiment, the temperature of the Fraction II precipitation step is −10±1° C. In yet another embodiment, the temperature of the Fraction II precipitation step is −10° C. In yet other embodiments, the temperature of the Fraction II precipitation step is −13, −12, −11, −10, −9, −8° C., −7° C., −6° C., −5° C., −4° C., −3° C., or −2° C.

In a specific embodiment, the pH of the Fraction B filtrate is adjusted to 7.1±0.2 using 1.0 M sodium bicarbonate solution. Additional alcohol is added with mixing to bring the calculated concentration to 25% (v/v). The pH is checked and readjusted, if necessary, to 7.3±0.2 using 1 M sodium bicarbonate or 4.0 pH buffer. The suspension is stirred for at least two hours at a temperature of −5±2° C. after completing the alcohol addition. After stirring is completed, the pH is readjusted to 7.3±0.2, if required. The suspension is centrifuged and the precipitate, Fraction II precipitate, is separated.

D. Cation Exchange Chromatography

To further enrich the immunoglobulin composition, in one embodiment, a Fraction II precipitate may be re-suspended in water or a low ionic strength buffer and subjected to cation exchange chromatography. In one embodiment, the Fraction II precipitate is re-suspended in water or low ionic strength buffer at a pH below 6.0. Typically, the pH of the re-suspended Fraction II precipitate is 5.2±0.2 and the conductivity of the suspension is low, typically no more than 1 mS/cm. The Fraction II suspension is then filtered to remove non-solubilized material prior to loading onto a cation exchange resin, equilibrated at a pH below 6.0. After loading the immunoglobulins onto the cation exchange resin (e.g., a cation exchange column), the resin may be washed with a wash buffer having a pH below 6.0. To elute the immunoglobulins, the cation exchange resin is then contacted with an elution buffer having a conductivity of at least 15 mS/cm (e.g., with a salt concentration of at least 150 mM NaCl or an equivalent salt thereof) and pH of greater than 7.0. In a specific embodiment, the suspended Fraction II precipitate is subjected to a solvent and detergent (S/D) treatment prior to performing cation exchange chromatography. Although a re-suspended Fraction II precipitate of the exemplary fractionation scheme presented herein is used as the starting material for the cation exchange methods provided herein, it will be appreciated that any plasma-derived immunoglobulin composition (i.e., fraction) containing IgG immunoglobulins and amidolytic activity (e.g., FXI and/or FXIa) and/or anti-complement activity (ACA) may be used in the methods provided herein.

It has been found that high levels of amidolytic activity (e.g., FXI and/or FXIa) and/or anti-complement activity (ACA) are co-eluted with IgG from the cation exchange resin. The inability to separate significant amounts of these impurities from the desired immunoglobulins results in a final IgG composition with high amidolytic activity and/or high anti-complement activity. Given the increased risk of thromboembolic events that has been attributed to high amidolytic activity in pharmaceutical immunoglobulin preparations, and adverse reactions that have been associated with anti-complement activity, there remains a need in the field for the removal of impurities that contribute to the amidolytic activity (e.g., FXI/FXIa) and/or anti-complement activity (ACA) present in many IgG products. Advantageously, it has been found that when a buffer having a pH above 7.0 is used to elute immunoglobulins from the cation exchange resin, that the amidolytic activity and anti-complement activity (ACA) elutes only in the lagging portion of the eluate. Notably, the elution of amidolytic activity and ACA in the lagging portion of the eluate corresponds with a shift in the pH of the eluate, from below 6.0 to above 7.0. As such, the leading portion of the eluate contains a high concentration of immunoglobulins and low concentration of amidolytic activity and ACA, while the lagging portion of the eluate has a lower immunoglobulin concentration and higher amidolytic activity and ACA. Accordingly, in preferred embodiments of the methods provided herein, the leading portion of the cation exchange eluate is collected separately from the lagging portion of the eluate.

In certain embodiments, the cation exchange resin is a weak cation exchange resin. Exemplary weak cation exchange resins include those with a carboxylic acid ligand, for example, carboxymethyl (CM) resins. In a preferred embodiment, the cation exchange resin used in the methods provided herein is a carboxymethyl resin, for example, CM-Sepharose.

In one embodiment, the Fraction II precipitate is re-suspended with cold water or a low ionic strength buffer at a pH between 4.8 and 5.6. In a specific embodiment, the pH of the water or buffer used for re-suspension is 5.2±0.3. In another specific embodiment, the pH of the water or buffer used for re-suspension is 5.2±0.2. In another specific embodiment, the pH of the water or buffer used for re-suspension is 5.2±0.1. In yet another specific embodiment, the pH of the water or buffer used for re-suspension is 5.2. In yet other embodiments, the pH of the water or buffer used for re-suspension is 4.8, 4.9, 5.0, 5.1, 5.2, 5.3, 5.4, 5.5, 5.6, 5.7, 5.8, 5.9, or 6.0.

In one embodiment, the cation exchange resin is pre-equilibrated to a pH between 4.6 and 5.6. In a specific embodiment, the resin is pre-equilibrated to a pH between 4.6 and 5.5. In another specific embodiment, the resin is pre-equilibrated to pH 5.0±0.4. In another specific embodiment, the resin is pre-equilibrated to pH 5.0±0.3. In another specific embodiment, the resin is pre-equilibrated to pH 5.0±0.2. In another specific embodiment, the resin is pre-equilibrated to pH 5.0±0.1. In another specific embodiment, the resin is pre-equilibrated to pH 5.0. In yet other embodiments, the resin is pre-equilibrated to pH 4.6, 4.7, 4.8, 4.9, 5.0, 5.1, 5.2, 5.3, 5.4, 5.5, 5.6, 5.7, 5.8, 5.9, or 6.0.

In one embodiment, after loading a clarified Fraction II suspension onto the cation exchange resin, the resin is washed with a buffer having a sufficiently low conductivity such that the immunoglobulins are not eluted from the resin and a pH between 5.1 and 5.9. In a specific embodiment, the pH of the wash buffer is 5.5±0.3. In another specific embodiment, the pH of the wash buffer is 5.5±0.2. In another specific embodiment, the pH of the wash buffer is 5.5±0.1. In another specific embodiment, the pH of the wash buffer is 5.5. In yet other embodiments, the pH of the wash buffer is 5.0, 5.1, 5.2, 5.3, 5.4, 5.5, 5.6, 5.7, 5.8, 5.9, or 6.0.

In one embodiment, the pH of the elution buffer is greater than 7.5. In another embodiment, the pH of the elution buffer is between 7.4 and 8.2. In a specific embodiment, the pH of the elution buffer is 7.8±0.3. In another specific embodiment, the pH of the elution buffer is 7.8±0.2. In another specific embodiment, the pH of the elution buffer is 7.8±0.1. In another specific embodiment, the pH of the elution buffer is 7.8. In yet other embodiments, the pH of the elution buffer is 7.0, 7.1, 7.2, 7.36, 7.4, 7.5, 7.6, 7.7, 7.8, 7.9, 8.0, 8.1, 8.2, 8.3, 8.4, or 8.5.

In one specific embodiment, the conductivity of the elution buffer is at least 10 mS/cm. In a preferred embodiment, the conductivity of the elution buffer is at least 15 mS/cm. In another preferred embodiment, the conductivity of the elution buffer is at least 20 mS/cm. In a specific embodiment, the conductivity of the elution buffer is between 10 mS/cm and 40 mS/cm. In another embodiment, the conductivity of the elution buffer is between 15 mS/cm and 30 mS/cm. In another embodiment, the conductivity of the elution buffer is between 20 mS/cm and mS/cm. In another embodiment, the conductivity of the elution buffer is between 25 mS/cm and 30 mS/cm. In yet other embodiments, the conductivity of the elution buffer is about 5 mS/cm, or about 6 mS/cm, 7 mS/cm, 8 mS/cm, 9 mS/cm, 10 mS/cm, 11 mS/cm, 12 mS/cm, 13 mS/cm, 14 mS/cm, 15 mS/cm, 16 mS/cm, 17 mS/cm, 18 mS/cm, 19 mS/cm, 20 mS/cm, 21 mS/cm, 22 mS/cm, 23 mS/cm, 24 mS/cm, 25 mS/cm, 26 mS/cm, 27 mS/cm, 28 mS/cm, 29 mS/cm, 30 mS/cm, 31 mS/cm, 32 mS/cm, 33 mS/cm, 34 mS/cm, 35 mS/cm, 36 mS/cm, 37 mS/cm, 38 mS/cm, 39 mS/cm, 40 mS/cm, or higher.

In one embodiment, the leading portion (i.e., the collected or pooled fraction of interest) of the eluate is no more than 80% of the total eluate. In a specific embodiment, the leading portion of the eluate is between 70% and 80% of the total eluate. In another specific embodiment, the leading portion of the eluate is between 60% and 80% of the total eluate. In another specific embodiment, the leading portion of the eluate is between 50% and 80% of the total eluate. In another specific embodiment, the leading portion of the eluate is between 70% and 75% of the total eluate. In yet another specific embodiment, the leading portion of the eluate is between 75% and 80% of the total eluate. In yet other embodiments, the leading portion of the eluate is 70%, 71%, 72%, 73%, 74%, 75%, 76%, 77%, 78%, 79%, or 80% of the total eluate.

In another embodiment, the leading portion (i.e., the collected or pooled fraction of interest) of the eluate is no more than 70% of the total eluate. In a specific embodiment, the leading portion of the eluate is between 60% and 70% of the total eluate. In another specific embodiment, the leading portion of the eluate is between 50% and 70% of the total eluate. In another specific embodiment, the leading portion of the eluate is between 60% and 65% of the total eluate. In yet another specific embodiment, the leading portion of the eluate is between 65% and 70% of the total eluate. In yet other embodiments, the leading portion of the eluate is 60%, 61%, 62%, 63%, 64%, 65%, 66%, 67%, 68%, 69%, or 70% of the total eluate.

In another embodiment, the leading portion (i.e., the collected or pooled fraction of interest) of the eluate is no more than 60% of the total eluate. In a specific embodiment, the leading portion of the eluate is between 50% and 60% of the total eluate. In another specific embodiment, the leading portion of the eluate is between 50% and 55% of the total eluate. In yet another specific embodiment, the leading portion of the eluate is between 55% and 60% of the total eluate. In yet other embodiments, the leading portion of the eluate is 50%, 51%, 52%, 53%, 54%, 55%, 56%, 57%, 58%, 59%, or 60% of the total eluate.

In another embodiment, the leading and lagging portions of the eluate are defined by the pH of the solution. In one embodiment, the leading portion is the eluate having a pH of no more than 7.0. In another embodiment, the leading portion is the eluate having a pH of no more than 6.5. In another embodiment, the leading portion is the eluate having a pH of no more than 6.0. In another embodiment, the leading portion is the eluate having a pH of no more than 5.5. In another embodiment, the leading portion is the eluate having a pH of no more than 5.0. In yet other embodiments, the leading portion is the eluate having a pH of no more than 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, or less.

In one embodiment, the leading portion of the eluate is defined as the fraction of the eluate eluting from the cation exchange resin prior to the point at which the $OD_{280}$ of the eluate drops below 2.0 AU. In another embodiment, the leading portion of the eluate is defined as the fraction of the eluate eluting from the cation exchange resin prior to the point at which the $OD_{280}$ of the eluate drops below 1.5 AU. In another embodiment, the leading portion of the eluate is defined as the fraction of the eluate eluting from the cation exchange resin prior to the point at which the $OD_{280}$ of the eluate drops below 1.0 AU. In another embodiment, the leading portion of the eluate is defined as the fraction of the eluate eluting from the cation exchange resin prior to the point at which the $OD_{280}$ of the eluate drops below 0.5 AU. In yet other embodiments, the leading portion of the eluate is defined as the fraction of the eluate eluting from the cation exchange resin prior to the point at which the $OD_{280}$ of the eluate drops below 2.0 AU, 1.9 AU, 1.8 AU, 1.7 AU, 1.6 AU, 1.5 AU, 1.4 AU, 1.3 AU, 1.2 AU, 1.1 AU, 1.0 AU, 0.9 AU, 0.8 AU, 0.7 AU, 0.6 AU, 0.5 AU, 0.4 AU, 0.3 AU, 0.2 AU, 0.1 AU, or less. In certain embodiments, the leading portion of the eluate is further defined as the portion of the eluate eluting from the cation exchange resin after the $OD_{280}$ of the eluate rises above a threshold, for example, 0.1 AU, 0.2 AU, 0.3 AU, 0.4 AU, 0.5 AU, 0.6 AU, 0.7 AU, 0.8 AU, 0.9 AU, 1.0 AU, 1.1 AU, 1.2 AU, 1.3 AU, 1.4 AU, 1.5 AU, 1.6 AU, 1.7 AU, 1.8 AU, 1.9 AU, 2.0 AU, or more.

E. Ultrafiltration/Diafiltration (UF/DF)

IgG compositions may be further concentrated by ultrafiltration/diafiltration. In one embodiment, the IgG composition may be concentrated by ultrafiltration to a protein concentration of between 2% and 10% (w/v). In certain embodiments, the ultrafiltration is carried out in a cassette with an open channel screen and the ultrafiltration membrane has a nominal molecular weight cut off (NMWCO) of no more than 100 kDa or no more than 90, 80, 70, 60, 50, 40, 30, or fewer kDa. In a preferred embodiment, the ultrafiltration membrane has a NMWCO of no more than 50 kDa.

As described in U.S. Patent Application Publication No. 2010/0330071, the content of which is hereby incorporated by reference in its entirety for all purposes, an open channel membrane may be used with a specifically designed post-wash and formulation near the end the production process to render the resulting IgG compositions about twice as high in protein concentration (200 mg/mL) compared to state of the art IVIGs (e.g., GAMMAGARD® LIQUID) without affecting yield and storage stability. With most of the commercial available ultrafiltration membranes a concentration of 200 mg/mL IgG cannot be reached without major protein losses. These membranes will be blocked early and therefore adequate post-wash is difficult to achieve. Therefore open channel membrane configurations have to be used. Even with open channel membranes, a specifically designed post-wash procedure has to be used to obtain the required concentration without significant protein loss (less than 2% loss). Even more surprising is the fact that the higher protein concentration of 200 mg/mL does not affect the virus inactivation capacity of the low pH storage step.

Upon completion of the ultrafiltration step, the concentrate may further be concentrated via diafiltration against a solution suitable for intravenous or intramuscular administration. In certain embodiments, the diafiltration solution may comprise a stabilizing and/or buffering agent. In a preferred embodiment, the stabilizing and buffering agent is glycine at an appropriate concentration, for example from 0.20 M to 0.30 M, or from 0.22 M to 0.28 M, or from 0.24 M to 0.26 mM, or at a concentration of 2.0, 2.1, 2.2, 2.3, 2.4, 2.5, 2.6, 2.7, 2.8, 2.9, or 3.0. In a preferred embodiment, the diafiltration buffer contains 0.25 M glycine.

Typically, the minimum exchange volume is at least about 3 times the original concentrate volume or at least 4, 5, 6, 7, 8, 9, or more times the original concentrate volume. The IgG solution may be concentrated to a final protein concentration of between 3% and 25% (w/v), or between 3% and 7%, or between 6% and 18% (w/v), or between 7% and 16% (w/v), or between 8% and 14% (w/v), or between 9% and 12%, or to a final concentration of 5%, or 6%, 7%, 8%, 9%, 10%, 11%, 12%, 13%, 14%, 15%, 16%, 17%, 18%, 19%, 20%, 21%, 22%, 23%, 24%, 25% or higher. In one embodiment, a final protein concentration of at least 23% is achieved without adding the post-wash fraction to the concentrated solution. In another embodiment, a final protein concentration of at least 24% is achieved without adding the post-wash fraction to the concentrated solution. In yet another embodiment, a final protein concentration of at least 25% is achieved without adding the post-wash fraction to the concentrated solution.

Typically, at the end of the concentration process, the pH of the solution will be from about 4.6 to 5.1.

In an exemplary embodiment, the pH of the IgG composition is adjusted to 5.2±0.2 using 1 M hydrochloric acid and concentrated to 5±1 g % protein by ultra-filtration (100 kDa or less nominal molecular weight cut-off limit). The concentrate is then dia-filtered with diafiltration solution (0.02 M NaCl, 0.05% (w/v) PEG). The dia-filtrate is cooled to 5±2° C. Tris buffer concentration of the solution is adjusted to 0.025 M using 2.0 M Tris and the pH is readjusted to 7.8±0.2.

F. Anion Exchange Chromatography

In one embodiment, the protein is then loaded onto an equilibrated ANX Sepharose® 4 Fast Flow Column to remove plasma-derived contaminants. After loading is completed, the column is washed with equilibration buffer (25 mM Tris, 20 mM NaCl, pH 7.8±0.2). The column fall through (IgG solution) from the loading and washing steps is pooled.

G. Virus Inactivation and/or Removal

In certain embodiments, the methods provided herein for the preparation of an enriched immunoglobulin composition will further include at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)):2021-2024, both of which are herein expressly incorporated by reference in their entirety for all purposes), and low pH incubation at high temperatures (Kempf et al., *Transfusion* 1991 (31)-423-427 and Louie et al., *Biologicals* 1994 (22):13-19).

Viral inactivation or removal steps may be performed on any intermediate immunoglobulin fractions generated during the manufacturing process. For example, in one embodiment, a viral inactivation or removal step may be performed on a Fraction I+II+III suspension, Fraction A suspension, Fraction B filtrate, Fraction II suspension, cation exchange eluate, anion exchange eluate, and the like.

In one embodiment, a viral inactivation or removal step is performed on a Fraction II suspension. In a preferred embodiment, the Fraction II suspension is subjected to solvent and detergent (S/D) treatment.

1. Solvent Detergent (S/D) Treatment

In order to inactivate various viral contaminants which may be present in plasma-derived products, one or more immunoglobulin manufacturing intermediates may be subjected to a solvent detergent (S/D) treatment. In a preferred embodiment, a Fraction II precipitate is re-suspended and S/D treated. Methods for the detergent treatment of plasma derived fractions are well known in the art (for review see, Pelletier J P et al., Best Pract Res Clin Haematol. 2006; 19(1):205-42). Generally, any standard S/D treatment may be used in conjunction with the methods provided herein. For example, an exemplary protocol for an S/D treatment is provided below.

Briefly, Triton X-100, Tween-20, and tri(n-butyl)phosphate (TNBP) are added to the clarified PptG filtrate at final concentrations of about 1.0%, 0.3%, and 0.3%, respectively. The mixture is then stirred at a temperature between about 18° C. and about 25° C. for at least about an hour.

In one embodiment, the S/D reagents (e.g., Triton X-100, Tween-20, and TNBP) are added by spraying rather than by fluent addition. In other embodiments, the detergent reagents may be added as solids to the immunoglobulin intermediate solution, which is being mixed to ensure rapid distribution of the S/D components. In certain embodiments, it is preferable to add solid reagents by sprinkling the solids over a delocalized surface area of the filtrate such that local overconcentration does not occur, such as in fluent addition. In another embodiment, a process improvement is realized by pumping an immunoglobulin containing solution into a tank where the SD-reagents are already present either in concentrated or diluted form.

2. Nanofiltration

In order to further reduce the viral load of the immunoglobulin composition provided herein, an immunoglobulin intermediate fraction may be nanofiltered using a suitable nanofiltration device. In certain embodiments, the nanofiltration device will have a mean pore size of at or about between 15 nm and 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of at or about between 15 nm and 72 nm, or at or about between 19 nm and 35 nm, or of at or about 15 nm, 19 nm, 35 nm, or 72 nm. In a preferred embodiment, the nanofilter will have a mean pore size of at or about 35 nm, such as an Asahi PLANOVA 35N filter or equivalent thereof.

Optionally, ultrafiltration/diafiltration may be performed to further concentrate the nanofiltrate. In one embodiment, an open channel membrane is used with a specifically designed post-wash and formulation near the end the production process resulting in an immunoglobulin composition of high concentration.

Subsequent to nanofiltration, the filtrate may be further concentrated by ultrafiltration and/or the buffer composition adjusted by diafiltration. In one embodiment, the nanofiltrate may be concentrated by ultrafiltration to a protein concentration of at or about between 0.5% and 10% (w/v). In certain embodiments, the ultrafiltration is carried out in a cassette with an open channel screen and the ultrafiltration membrane has a nominal molecular weight cut off (NMWCO) of less than at or about 150 kDa or less than at or about 140, 130, 120, 100, 90, 80, 70, 60, 50, 40, 30, or fewer kDa. In one embodiment, the ultrafiltration membrane has a NMWCO of no more than 50 kDa.

3. Incubation at Low pH

In certain embodiments, an immunoglobulin containing solution may be treated to reduce or inactivate the viral load of the composition. In one embodiment, this is achieved by adjusting the pH of the of the composition to low pH, for example, less than at or about 6.0, and incubating for at least about a week prior to releasing the composition. In a preferred embodiment, the pH of the bulk solution is adjusted to less than at or about 5.5 prior to incubation. In a more preferred embodiment, the pH of the solution is lowered to less than at or about 5.0 prior to incubation. In certain embodiments, the pH of the solution is lowered to less than at or about 6.0 or less than at or about 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, or lower prior to incubation.

In certain embodiments, the solution is then incubated for at least one week, or at least 2, 3, 4, or more weeks, or for at least 1, 2, 3, or more months. In preferred embodiments, the composition is incubated at a temperature above 20° C., or above 25° C., or above 30° C. In particular embodiments, the composition is incubated at a temperature of 20° C., or 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or higher.

4. Lyophilization and Heat Treatment

In yet other embodiments, the present invention provides lyophilized immunoglobulin compositions, lyophilized according to methods known in the art. The viral activity of these lyophilized compositions, which may have previously been subjected to other viral inactivation or removal steps such as S/D treatment or nanofiltration, may be further reduced by heat treatment of the lyophilized composition. Heat treatments for the inactivation of viral loads in blood factors are well known in the art (for example, see, Piszkiewicz et al., Thromb Res. 1987 Jul. 15; 47(2):235-41; Piszkiewicz et al., Curr Stud Hematol Blood Transfus. 1989; (56):44-54; Epstein and Fricke, Arch Pathol Lab Med. 1990 March; 114(3):335-40).

H. Formulation

Upon completion of the diafiltration step, the protein concentration of the solution is adjusted to with the diafiltration buffer to a final concentration of between about 3% and about 20% (w/v), or between 3% and 7%, or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, 20%, 21%, 22%, 23%, 24%, 25%, or higher. In a preferred embodiment, the final protein concentration of the solution is between about 9% and about 11%, more preferably about 10%.

The formulated bulk solution is further sterilized by filtering through a membrane filter with an absolute pore size of no more than about 0.22 micron, for example about 0.2 micron. Then the solution is aseptically dispensed into final containers for proper sealing, with samples taken for testing.

In one embodiment, the IgG composition is further adjusted to a concentration of about 10.2±0.2% (w/v) with diafiltration buffer. The pH is adjusted to about 4.4 to about 4.9 if necessary. Finally, the solution is sterile filtered and incubated for three weeks at or about 30° C.

In an exemplary embodiment, the resulting IgG solution is stabilized with NaCl (0.15 M maximum), glycine (0.3 M maximum), glucose (0.11 M maximum), and human albumin (3 mg/mL maximum). The pH is adjusted to 7.0±0.2 using 1 M hydrochloric acid. The solution is then concentrated by ultrafiltration to the desired concentration and the pH readjusted to 7.15±0.1 using 1 M hydrochloric acid or 1 M sodium hydroxide. The bulk solution is sterile filtered using 0.2 micron pore size filter or equivalent.

The sterile IgG solution may be aseptically dispensed into a container, stoppered for lyophilization, frozen, lyophilized, sealed under aseptic conditions and capped.

VIII. Examples

Among other advantages, Examples 1 to 7 demonstrate that: (1) step elution of immunoglobulins from a cation exchange resin (e.g., CM-Sepharose) results in a bimodal distribution of protein, where amidolytic activity (PL-1) is eluted later than IgG, making it possible to remove amidolytic activity with a minimal loss of IgG yield; (2) the elution of amidolytic activity (PL-1) from the cation exchange resin (e.g., CM-Sepharose) correlates with, and is likely caused by, a pH shift on the CM column during elution according to the methods provided herein; (3) The amount of protein loaded onto a cation exchange resin (e.g., CM-Sepharose) does not influence the removal of amidolytic activity (PL-1) over at least a range of 60 to 120 mg protein per mL resin; (4) monitoring the pH at the column outlet and stopping elution when the increase is manifest leads to a partial removal of amidolytic activity (PL-1) activity, likely because the pH equilibrium at the top of the column has already been disturbed; (5) amidolytic activity can be significantly reduced with a minimal loss in IgG yield (≤10%) by collecting an initial elution pool of less than 3 CV, as such, monitoring the volume of a CM-Sepharose elution step is a simple method for significantly reducing the amidolytic activity of an immunoglobulin composition prepared according to the methods provided herein; and (6) by collecting the "first peak" of a CM-Sepharose elution step, a composition having lower IgG aggregate concentration, lower PKA activity, lower PL-1 activity, a higher IgG monomer concentration, and a more desirable IgG subclass distribution can be achieved.

Furthermore, Examples 8 and 9 demonstrate at least that (1) FXIa and elevated TGA causing proteins can be separated at CM-chromatography by splitting off the last 25% part of the eluate; (2) the advantages described above can be replicated in large-scale manufacturing processes; and (3) cation exchange (i.e., CM-Sepharose) eluates produced in large-scale manufacturing processes can be pooled by monitoring the OD, for example the eluate may be collected in a first pool until the OD of the eluate falls below 2.0, providing significant separation of unwanted proteins causing elevated FXIa and TGA values.

Example 1

This example describes the distribution of unwanted proteins causing elevated TGA, FXIa, and shortened NAPTT values from a Fraction II immunoglobulin composition prepared according to a modified Kistler-Nitschmann alcohol fractionation. These impurities can be separated during elution of a cation exchange chromatography step (e.g., CM Sepharose fast flow chromatography).

This example demonstrates a significant reduction in the amidolytic content (e.g., FXI and/or FXIa) during elution of cation exchange chromatography. The method results in a final immunoglobulin product containing significantly less TGA and FXIa activity. This reduction is achieved by a specific fractionation of the CM eluate step, which effectively separates amidolytic activity (present in the lagging portion of the eluate) from the main IgG fraction (found in the leading portion of the eluate). This example shows that by dividing the cation exchange eluate into leading and lagging portions, undesirable trace proteins are separated from the bulk of the IgG content. Moreover, this examples demonstrated that this process is effective and economically feasible for large-scale manufacturing.

Briefly, the Fraction II precipitate was prepared as follows. After cryo-precipitation of pooled human plasma, a fraction I+II+III precipitate was formed by precipitation with 20% alcohol at pH 6.9. After the re-suspension of precipitate I+II+III, alcohol is added to a final concentration of 20% at pH of 7.2, to form precipitate A. Separation of precipitate A was performed by centrifugation. Fraction I+III (also referred to as suspension B precipitate) is formed by precipitation of a suspended precipitate A with 17% alcohol. The precipitate is recovered by filtration or centrifugation. Suspension B filtrate is then processed to form Fraction II, which contains the partially purified gamma globulin (e.g., IgG) plasma protein fraction.

A clarified suspension of Fraction II is then treated with a mixture of solvent detergent (SD) and loaded onto a CM Sepharose ff column. After washing out the residual SD reagents, the IgG fraction bound to the resin is eluted. Subsequently the immunoglobulin solution is ultra-/diafiltered and then loaded on an anion exchanger to remove trace impurities. After another concentration step the final formulation may be followed by lyophilization.

The Fraction II precipitate was then dissolved in cold water at 4° C. and pH 5.2±0.2. After clarification by CWSS filtration, the solution was adjusted for SD treatment. The protein concentration was adjusted to 2% and the temperature during the SD incubation was held in the range of 20° C. to 25° C. The protein solution was then loaded onto an equilibrated CM-Sepharose fast flow column (equilibration buffer: 0.025 M sodium acetate, pH 5.0±0.2). After loading, the column was washed with 30 column volumes of acetate buffer (0.01 M sodium acetate. pH 5.5±0.2), to wash out the SD reagents, before the adsorbed protein was eluted with elution buffer (0.25 M NaCl, 0.2 M Glycine, 0.1% PEG 3350, 25 mM Tris, pH 8.00). The collection of the first part of the eluate (E1) was started at OD 400 mAU and stopped after exactly 2.7 column volumes (FIG. 1). The second fraction (E2) of the elution peak was collected until the OD dropped to 400 mAU again. The eluted fractions were then processed separately for the remainder of the process.

The E1 and E2 compositions were then adjusted to pH to 5.2 and ultra-/diafiltered against diafiltration buffer (0.02 M NaCl, 0.05% PEG 3350) to concentrate to 5% protein (w/v). 0.025 M Tris was added to the compositions and the pH was adjusted to 7.7. The IgG fractions were then loaded onto an equilibrated ANX-Sepharose fast flow column equilibrated with buffer (0.025 M Tris, 0.02 M NaCl, pH 7.7). The resulting ANX flow-through was collected and supplemented with 8.5 g/L NaCl, 16.5 g/L glycine, 21.7 g/L glucose anhydride, and 1 g/L albumin (20%). The pH was then adjusted and the E1 and E2 compositions were concentrated to 10% (w/v) protein by ultrafiltration. After concentration, the concentrated solutions are again supplemented with NaCl and glycine (but not the albumin) and the pH is adjusted to 7.1, if necessary, before the sterile filtration.

A chromatograph showing the absorbance (mAU), conductivity, and pH of the chromatography step is provided in FIG. 1. As can be seen, a single step elution with the elution buffer described above results in a two peak elution. Notably, upon addition of the elution buffer, the pH of the eluate drops significantly as the first peak comes off the column, and then rises sharply with the elution of the second peak. As described, the elution peaks were separated by collecting 2.7 column volumes in a first fraction E1 (left of the vertical line shown in FIG. 1) and a second fraction (right of the vertical line shown in FIG. 1).

The eluted fractions (E1 and E2) were the processed separately to produce a final immunoglobulin preparation, as described below. To do so, the pH of Fractions E1 and E2 were adjusted to 5.2 and the samples diafiltered against diafiltration buffer (0.02M NaCl, 0.05% PEG 3350) to concentrate the composition to a final protein concentration of 5%. After diafiltration, 0.025M Tris was added to each protein solution and the pH was adjusted to 7.7. The IgG fractions were then loaded onto an equilibrated ANX-Sepharose fast flow column (equilibration buffer 0.025M Tris, 0.02M NaCl pH 7.7) and the flow-through fraction was collected. The ANX flow-through was then supplemented with 8.5 g/L NaCl, 16.5 g/L glycine, 21.7 g/L glucose anhydride, and 1 g/l albumin (20%). The pH of the solution is then adjusted to 7.00 and the immunoglobulin sample is concentrated to 10% protein by ultrafiltration. After concentration, NaCl, glycine, and glucose anhydride are again added and the pH is adjusted to 7.1, if necessary, prior to sterile filtration.

To characterize the chromatographic step, a mass balance was determined, the results of which are shown in Table 1. Roughly 10% of the total protein was found in the second part of the elution peak. This is the yield loss which occurs when the pooled composition is stopped after 2.7 column volumes of eluate.

TABLE 1

Mass balance of the CM-chromatographic enrichment step.

| | TPUV (%) | Protein (g) | Yield (%) | Yield (g/l plasma) |
|---|---|---|---|---|
| Fraction II diss. | 6.99 | 150.07 | 100.00 | 3.93 |
| CWSS | 6.33 | 149.74 | 99.78 | 3.92 |
| CM E1 | 2.97 | 136.27 | 90.80 | 3.57 |
| CM E2 | 1.04 | 16.40 | 10.93 | 0.43 |
| E1 ANX D/N | 2.56 | 92.96 | 61.94 | 2.43 |
| E1 ANX 2M | 0.87 | 11.25 | 7.50 | 0.29 |
| E1 FC | 4.76 | 76.31 | 50.85 | 2.00 |
| E2 ANX D/N | 2.71 | 12.56 | 8.37 | 0.33 |
| E2 ANX 2M | 0.78 | 1.02 | 0.68 | 0.03 |
| E2 FC | 4.77 | 8.21 | 5.47 | 0.21 |

The final containers prepared from the two CM elution fractions were then analyzed for molecular size distribution, anti-complementary activity, amidolytic activity using both PL-1 and TGA as substrates, FXIa activity, and NAPTT activity. The results are shown in Table 2 and Table 3. The biochemical characterization of the final containers derived from the first and the second part of the eluted IgG fraction revealed that the first part of the elution is essentially free from FXIa and other undesirable proteins causing elevated TGA and shortened NAPTT values. In contrast, FXIa and amidolytic activities are enriched in the second part, where the aggregate and oligo-dimer content is also higher. Interestingly, the ACA value in the first part of the eluate is very low, while the second part of the eluate shows a much higher value.

TABLE 2

Comparison of the molecular size distribution of the two final containers E1 and E2.

| HPLC | Polymers | Oligo/Dimers | Monomers | Fragments |
|---|---|---|---|---|
| E1 FC | 0.20% | 4.66% | 93.13% | 2.01% |
| E2 FC | 2.82% | 9.09% | 85.95% | 2.15% |

TABLE 3

Comparison of the biochemical characterization of the two final containers E1 and E2.

| | PKKA PKKA IU/ml | TGA % normal plasma | FXIa mU/ml FXIa | ACA C'H50 units consumed/% | PL-1 nmol/ml min | NAPTT (FXI Plasma) |
|---|---|---|---|---|---|---|
| E1 FC | <4 | 96.87 | <0.04 | 16.9/16.6% | <10 | >5 mg |
| E2 FC | 5.9 | 256.41 | 2.14 | 48.2/58.7% | <10 | >5 mg |

In conclusion, the split of the elution from the CM Sepharose ff column results in two fractions and enables the manufacturing of a substantially FXIa free IgG compositions.

Example 2

In order to reduce the amount of amidolytic activity present in manufacturing-scale immunoglobulin preparations, the conditions used to elute and fractionate cation exchange chromatography were investigated. The details of these investigations are provided below.

A series of experiments was performed to find suitable solutions for reducing/removing amidolytic activity during downstream process according to the Gammagard SID production method described herein. Briefly, Cohn Fraction paste was dissolved in cold water at 4° C. and pH 5.2±0.2. After clarification by CWSS filtration the samples were either sterile filtrated and stored at 4° C. or diluted with water to a protein concentration of 2% for immediate processing. The solution was then brought to 20-25° C. and incubated for 1 hour with a solvent/detergent mixture (1% Triton X-100, 0.3% Tween 80; 0.3% TNBP) before the protein solution was loaded onto an equilibrated CM-Sepharose fast flow column (equilibration buffer: 25 mM Na-Acetate, pH 5.0±0.2). After loading, the column was washed with acetate-buffer (0.01 M Na-Acetate, pH 5.5±0.2) and adsorbed IgG is eluted with elution buffer (0.25 M NaCl, 0.2 M glycine, 0.1% PEG 3350, 25 mM Tris, pH 7.8). During the CM Sepharose ff runs, the following parameters are monitored to fractionate CM eluate (at a definite point): OD 280; pH; and elution volume in column volumes (CV). The eluates were then either ultra/diafiltrated with diafiltration buffer (0.02 M NaCl, 0.05% PEG 3350), or immediately used for analysis. This concentration step was performed in order to measure amidolytic activity at protein values also corresponding to a 10% final container composition.

Figure 2:
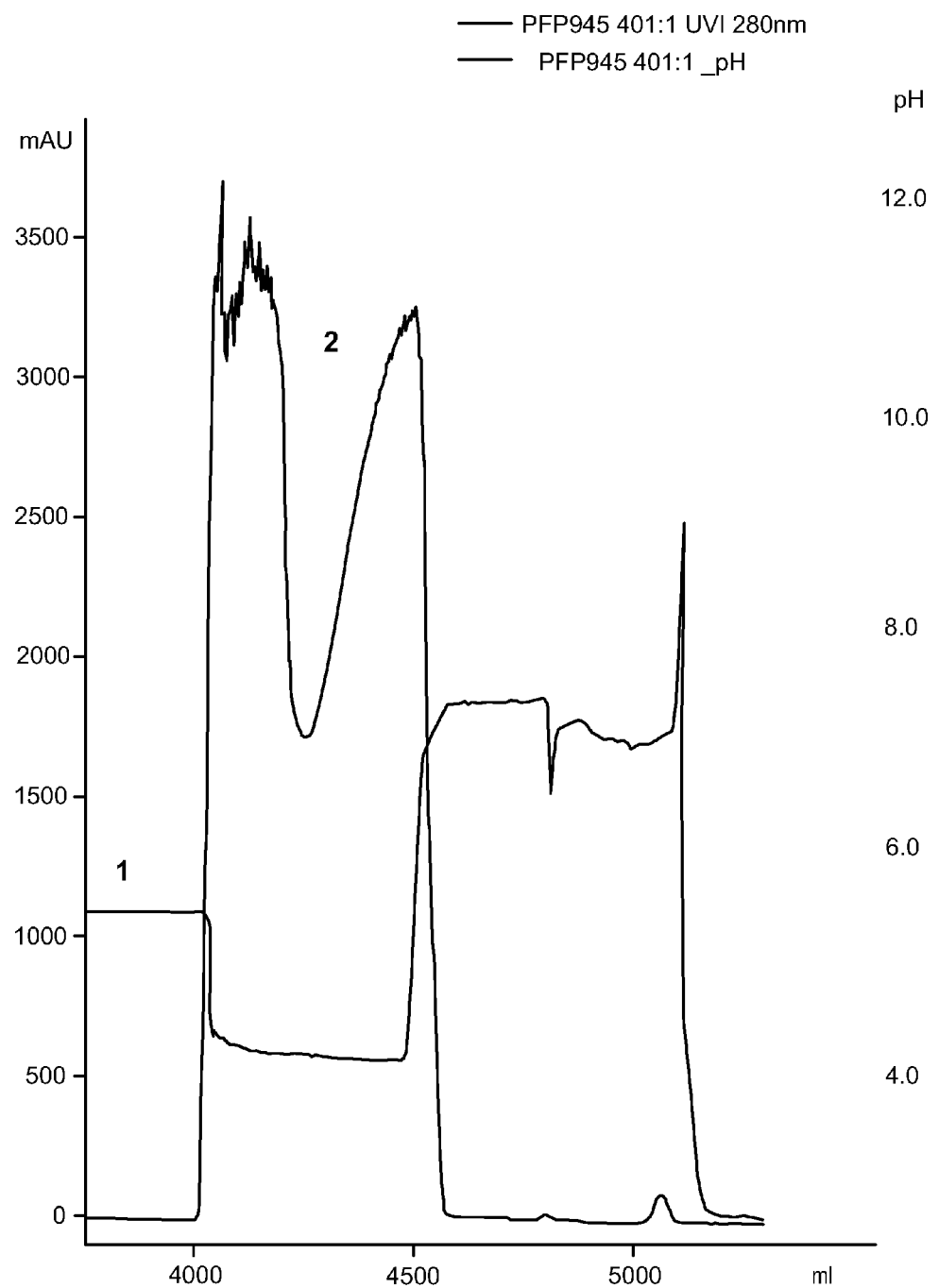
FIG. 2. shows a chromatograph of the CM Sepharose ff run described in Example 2. Illustrates the course of pH and OD 280 during elution of the IgG fraction from CM Sepharose ff (starting material: Cohn fraction II paste pathway II; P247011V; adsorption steps: FIX; FVII; AT III).

During elution, the eluate quickly attained the conductivity value of the CM elution buffer. However, as shown in FIG. 2, the pH of the eluate measured at the column outlet initially dropped from 5.5, as in the wash buffer, to below 5 0 (4 3-4.8) and remained unchanged for the first 4 CV, despite the fact that the elution buffer had a pH of 7.8. An increase in pH to about 7.8 was seen at the end of the eluate collection. Monitoring of the OD 280 at the column outlet shows that this pH shift corresponds to the release of a second peak, where the majority of the amidolytic activity (as measured via PL-1 assay) is detected.

Example 3

To further investigate the bimodal CM-Sepharose elution phenomenon and pH shift observed in Example 1 and Example 2, individual elution fractions were collected during another CM-Sepharose fast flow chromatography experiment. Briefly, CM-Sepharose fast flow chromatography was performed as described above, with fractions collected and analyzed separately before pooling fractions A-N and concentrating by ultrafiltration The starting material for the chromatographic step was Cohn Fraction II paste (P25001ivLE; FIX and AT-III adsorbed). The CM-Sepharose column was equilibrated with buffer having a pH of 5.2 and washing was performed at a pH of 5.7. The flow rate of the chromatographic step was maintained at 0.64 cm/min.

After the pH shift, an increasing amount of amidolytic activity (PL-1) is found in the fractions. Even in the concentrated pool a reduction of the amidolytic activity is observed. The fact, that PL1 activity is detectable after ultra-/diafiltration is either due to dilution in CM eluate or to generation of the same during concentration.

As shown in Table 4, fractions eluting with a pH below 5.5 (fraction A-N) contained much lower concentrations of amidolytic activity as compared to those eluting with higher pH values (fractions O and P). Quantitation of amidolytic activity shows that more activity was eluted in fractions O and P than in all of fractions A-N combined. After the pH shift, an increasing amount of amidolytic activity (PL-1) was found in the fractions. Even in the concentrated pool a reduction of the amidolytic activity is observed. The fact, that PL1 activity was detectable after ultra-/diafiltration is either due to dilution in CM eluate or to generation of the same during concentration.

TABLE 4

Analysis of CM-Sepharose ff elution fractions.

| Sample | Eluate in column volume CV | pH | Volume (corrected) g | Protein conc. % | Protein (corrected) g | Protein step recovery % | Amidolytic activity (PL-1) nmol/ml · min | Amidolytic activity (PL-1) nmol/min per g protein |
|---|---|---|---|---|---|---|---|---|
| Paste resusp. | | | 1349 | 5.4 | 73.00 | 100.0 | 14.5 | 268 |
| CWSS filtrate | | | 1480 | 4.7 | 68.97 | 94.5 | 14.4 | 309 |
| Fraction A | 0.26 | 5.6 | 246 | 0.04 | 0.10 | 0.1 | <10 | |
| Fraction B | 0.26 | 4.8 | 247 | 2.17 | 5.36 | 7.3 | <10 | |
| Fraction C | 0.27 | 4.6 | 255 | 6.69 | 17.09 | 23.4 | <10 | |
| Fraction D | 0.27 | 4.6 | 256 | 5.55 | 14.22 | 19.5 | <10 | |
| Fraction E | 0.27 | 4.6 | 256 | 4.21 | 10.78 | 14.8 | <10 | |
| Fraction F | 0.28 | 4.7 | 270 | 2.99 | 6.06 | 11.1 | <10 | |
| Fraction G | 0.26 | 4.6 | 252 | 2.15 | 5.41 | 7.4 | <10 | |
| Fraction H | 0.26 | 4.7 | 245 | 1.49 | 3.66 | 5.0 | <10 | |
| Fraction I | 0.29 | 4.7 | 278 | 0.99 | 2.76 | 3.8 | <10 | |
| Fraction J | 0.30 | 4.7 | 267 | 0.67 | 1.92 | 2.6 | <10 | |
| Fraction K | 0.27 | 4.7 | 258 | 0.51 | 1.32 | 1.6 | <10 | |
| Fraction L | 0.26 | 4.7 | 251 | 0.43 | 1.08 | 1.5 | <10 | |
| Fraction M | 0.27 | 4.7 | 257 | 0.37 | 0.95 | 1.3 | <10 | |
| Fraction N | 0.28 | 4.9 | 267 | 0.39 | 1.04 | 1.4 | <10 | |
| Fraction O | 0.34 | 5.5 | 324 | 0.52 | 1.69 | 2.3 | 28.2 | 5423 |
| Fraction P | 0.29 | 7.5 | 276 | 0.34 | 0.94 | 1.3 | 29.6 | 8706 |
| Fraction Q | 0.28 | 7.8 | 270 | 0.01 | 0.03 | 0.0 | <10 | |
| CM eluate A-N | | | 3616 | 1.91 | 69.06 | 94.6 | <10 | |
| A-N after UF/DF | | | 996 | 7.00 | 69.70 | 95.5 | 12.7 | 181 |

Example 4

To further define the boundaries of amidolytic activity elution from CM-Sepharose ff resin, another experiment was performed, as described above, except that CM-eluates were collected in fractions defined by a pH boundary. Specifically, CM-eluates were collected up to a pre-defined pH (4.3, 4.8, 6.0, 7.5), as monitored at the column outlet. In this experiment, the starting material for the chromatographic step was Cohn Fraction II paste (P25001ivLE; FIX and AT-III adsorbed), as in Example 3. The CM-Sepharose column was equilibrated at a pH of 4.8 and washed at a pH of 5.3. Eluate fractions were ultra-/diafiltrated and pH adjusted with Tris prior to analysis. In this experiment, the pH of the eluate dropped to 4.1 at the beginning of the elution step. Analysis of the collected eluate fractions is shown in Table 5.

TABLE 5

Analysis of CM-Sepharose ff elution fractions.

| Sample | Eluate in column volume CV | Protein conc. % | Amidolytic activity (PL-1) nmol/ml · min | Amidolytic Activity (PL-1) nmol/min per g protein |
|---|---|---|---|---|
| paste resusp. | | 5.7 | 14.4 | 251 |
| CWSS filtrate | | 4.9 | 14.1 | 267 |
| CM-eluate (pH 4.3) | 4.88(4.38) | 2.29 | <10 | |
| after UF/DF | | 7.42 | 12.0 | 162 |
| CM-eluate (pH 4.8) | 4.49 | 2.66 | <10 | |
| after UF/DF | | 6.57 | 12.7 | 193 |
| CM-eluate (pH 6.0) | 5.21 | 2.11 | <10 | |
| after UF/DF | | 7.20 | 14.1 | 196 |
| CM-eluate (pH 7.5) | 6.43 | 1.71 | <10 | |
| after UF/DF | | 6.71 | 15.8 | 235 |

Example 5

Next, it was determined whether or not a reduction in the amount of protein per unit CM-Sepharose resin would further enhance the peak separation shown in FIG. 2. In order to test this, a series of CM-Sepharose ff chromatographic runs were performed with decreasing protein loads, ranging from 118 mg protein per mL resin down to 57 mg/protein per mL resin. As in Example 2, the starting material for the experiment was Cohn fraction II paste pathway II; P24701IV; which includes removal of FIX, FVII, and ATIII from the cryo-poor plasma by adsorption (Table 6). The resin was equilibrated at pH 5.2 and the wash step was performed at pH 5.7. CM-Sepharose eluates were pooled as in Example 2, into a first part (the first peak) and a second part (the second peak). FIG. 2 provides an exemplary chromatograph, wherein the first pool ends and the second pool begins when the UV absorbance of the eluate bottoms out at approximately $OD_{280}=1.6\pm0.2$ between the two peaks.

TABLE 6

Analysis of the starting material (Cohn fraction II paste pathway II; P24701IV).

| sample | volume (corrected) g | protein (corrected) g | recovery % | amidolytic act. (PL-1) nmol/ml · min | amidolytic act. (PL-1) nmol/min · g protein |
|---|---|---|---|---|---|
| COHN II resusp. | 1001 | 75 | 100 | 24.3 | 325 |
| CWSS filtrate | 1083 | 74 | 98 | 22.5 | 331 |
| Sterile filtrated | 1067 | 72 | 96 | 22.5 | 335 |

As shown in Table 7, reducing the protein load of the resin showed no effect on peak separation, but had an impact on the recovery. Consistent with the results presented in the previous examples, very low levels of amidolytic activity are present in the first eluate pools of each chromatographic run.

TABLE 7

Analysis of CM-Sepharose chromatographic purifications performed with variable protein loads.

| mg protein/ ml media | Sample | Eluate in column volume* | Protein concentration % | Recovery % | Amidolytic activity (PL-1) nmol/ml · min |
|---|---|---|---|---|---|
| 118 | CM-eluate first part | 2.7 | 3.5 | 81.5 | <10 |
| | CM-eluate second part | 4.8 | 0.3 | 13.5 | |
| | after UF/DF | | 8.49 | | <10 |
| 110 | CM-eluate first part | 2.3 | 4.0 | 78.1 | <10 |
| | CM-eluate second part | 5.1 | 0.5 | 19.6 | |
| | after UF/DF | | 7.18 | | <10 |
| 80 | CM-eluate first part | 2.8 | 2.25 | 72.4 | <10 |
| | CM-eluate second part | 3.5 | 0.6 | 24.7 | |
| | after UF/DF | | 7.06 | | <10 |
| 72 | CM-eluate first part | 2.7 | 2.05 | 76,7 | <10 |
| | CM-eluate second part | 4.4 | 0.4 | 23,1 | |
| | after UF/DF | | 5.62 | | <10 |
| 57 | CM-eluate first part | 2.3 | 1.71 | 67.0 | <10 |
| | CM-eluate second part | 4.8 | 0.4 | 27.9 | |
| | after UF/DF | | 3.88 | | <10 |

Example 6

To further validate the experimental findings described above, CM-Sepharose chromatographic purifications were performed with variable flow rates and elution pooling schemes. Briefly, a Cohn Fraction II paste containing high amidolytic activity content (100 nmol/mL·min at 6% protein) was processed as described herein to the fraction preceding ANX chromatography. For all CM-Sepharose runs, the eluate was collected when the UV began to rise and was stopped after either 3 CV or after 4 CV.

Three CM Sepharose chromatographic purifications were performed as follows. The collected eluate fractions were concentrated as described herein and then further concentrated to avoid PL-1 values below the detection limit for the PL-1 assay.

First Run: The CM-Sepharose resin was rinsed and equilibrated at a flow rate of 1 cm/min. The flow rate of the protein loading, washing, and elution steps was held constant at 0.64 cm/min. 3 column volumes (3 CV) of eluate were collected in the main pool.

Second Run: The CM-Sepharose resin was rinsed and equilibrated at a flow rate of 1.2 cm/min. The flow rate of the protein loading step was 0.64 cm/min. The flow rate of the wash step was 0.64 cm/min for the first 1.2 column volumes (CV) and 1.8 cm/min for the following 28.8 CV. The elution step was performed at 0.64 cm/min. 3 column volumes (3 CV) of eluate were collected in the main pool.

Third Run: The CM-Sepharose resin was rinsed and equilibrated at a flow rate of 1.2 cm/min. The flow rate of the protein loading step was 0.64 cm/min. The flow rate of the wash step was 0.64 cm/min for the first 1.2 column volumes (CV) and 1.8 cm/min for the following 28.8 CV. The elution step was performed at 0.64 cm/min. 4 column volumes of eluate were collected in the main pool.

The main pool of each CM-Sepharose chromatographic run was concentrated and analyzed for amidolytic activity (PL-1), total protein concentration, and HPLC profile. As shown in Table 8, increasing the flow rate of the washing step resulted in lower amounts of amidolytic activity in the main pool (compare Run 1 and Run 2). The collection of 4 CV, rather than 3 CV, provided a nominal total protein yield (2.55 g/L plasma vs. 2.5 g/L plasma; compare Run 3 and Run 2), however, it more than doubled the total amount of amidolytic activity present in the final composition (384.7 PL-1 nmol/min·g protein vs. 188.5 PL-1 nmol/min·g protein). Pooling of 4 CV also increased the aggregate content of the final immunoglobulin composition (0.52% vs. 0.12%; compare Run 3 and Run 2). Notably, the final amidolytic and aggregate contents of the composition prepared by Run 2 are consistent with those seen above (See, Table 2, Table 4, and Table 5).

TABLE 8

Analysis of CM-Sepharose chromatographic purifications performed with variable wash flow rates and eluate collection volumes.

|  |  | 1. Run | 2. Run | 3. Run |
| --- | --- | --- | --- | --- |
| Protein yield g/L plasma |  | 2.36 | 2.5 | 2.55 |
| Protein value % |  | 8.12 | 7.48 | 9.28 |
| PL-1 nmol/ml · min |  | 27.5 | 14.1 | 35.7 |
| PL-1 nmol/min · g protein |  | 338.7 | 188.5 | 384.7 |
| HPLC | Aggregates | 0.18 | 0.12 | 0.52 |
|  | Oligo/Dimers | 5.84 | 5.74 | 6.38 |
|  | Monomers | 93.88 | 94.10 | 92.98 |
|  | Fragments | 0.09 | 0.04 | 0.12 |

Example 7

To demonstrate that the results provided above could be scaled-up to industrial manufacturing scale, 360 g of Cohn Fraction II starting material was processed as in the above experiments. 2.9 CV of CM-Sepharose was collected in a first pool and the balance of the eluate was collected in a second pool. The resulting eluate pools were then processed to a final container composition, as described herein, suitable for administration to an individual. This further processing included ANX chromatography, ultra-/diafiltration, and lyophilization from the final formulation. The biochemical characteristics of each final preparation was then analyzed and the results are presented in Table 9.

TABLE 9

Comparison of the biochemical characterization of the two final containers E1 (first part of the elution; 2.9 CV) and E2 (second part of the elution; >2.9 CV).

|  |  | CM eluate after downstream processing | |
| --- | --- | --- | --- |
|  |  | first part of elution | second part of elution |
| Protein value % |  | 4.90 | 3.95 |
| IgG g/L |  | 48.3 | 36.3 |
| IgA g/L |  | 0.006 | 0.0002 |
| IgG subclasses | IgG 1 | 71.9 | 71.4 |
|  | IgG 2 | 21.0 | 16.4 |
|  | IgG 3 | 4.6 | 10.8 |
|  | IgG 4 | 2.5 | 1.4 |
| HPLC | Aggregates | 0.07 | 0.06 |
|  | Oligo-/Dimers | 4.59 | 10.76 |
|  | Monomers | 94.81 | 87.86 |
|  | Fragments | 0.52 | 1.32 |
| CA electrophoresis |  |  |  |
|  | Albumin | 1.2 | 2.3 |
|  | α/β globulin |  | 0.2 |
|  | γ globulin | 98.8 | 97.5 |
| ACA (C'H 50) |  | 25.4 | 25.5 |
| PKA IE/ml |  | <0.6 | 41.2 |
| PL-1 nmol/ml · min |  | 19.7 | 728.6 |
| PL-1 nmol/min · g protein |  | 402.0 | 18446.6 |

As shown in Table 9, the final composition derived from the first part of the CM-Sepharose elution contained 50-fold less amidolytic activity than the final composition derived from the second part of the CM-Sepharose elution (402 nmol PL-1/min·g protein vs. 18,446.6 nmol PL-1/min·g protein). The final composition derived from the first part of the CM-Sepharose elution also contained less albumin (1.2% vs. 2.3%), α/β globulin (undetected vs. 0.2%), PKA activity (<0.6 IE/mL vs. 41.2 IE/mL), and IgG 3 (4.6% vs. 10.8%) as compared to the final composition derived from the second part of the CM-Sepharose elution. Furthermore, the composition derived from the first part of the CM-Sepharose elution contained a much higher IgG monomer content (94.81% vs. 87.86%) than the final composition derived from the second part of the CM-Sepharose elution.

Example 8

To further validate the results provided above, a portion of Fraction II paste (R110×D142; centrifuged precipitate A) was prepared according to the methods provided herein. The paste was then re-suspended and loaded onto a CM-Sepharose cation exchange column as described herein and eluted as described above. The eluate (total volume: 4743 mL) was divided into a first fraction containing 75% of the total eluate (3530 mL) and a second fraction containing 25% of the total eluate (1213 mL). Both the first and second CM-Sepharose eluate fractions were then processed to the final container as described herein and analyzed for FXIa, TGA, NAPTT, and amidolytic (PL-1) activity, IgG aggregate, and ACA content. The results are provided in Table 10. Consistent with the results provided above, separation of the CM-Sepharose eluate into a first and second pool results in the reduction of FXIa and TGA activity in the final immunoglobulin preparation.

TABLE 10

Biochemical characterization of the first and second CM-Sepharose elution fractions.

| Test | Unit | First part of the CM-eluate | Second part of the CM-eluate |
|---|---|---|---|
| TGA | % of normal plasma | 96.87 | 256.41 |
| Specific F-XIa | mU/mL | <0.04 | 2.14 |
| NAPTT | mg | <5 | <5 |
| Amidolytic activity (PL-1) | nmol/mL min | <10 | <10 |
| PKA | IE/mL | <4 | 5.9 |
| MSD | % aggregates | 0.20 | 2.82 |
| ACA | % | 16.6 | 58.7 |

Example 9

To further asses the feasibility of scaling-up the methods provided herein, a CM-Sepharose eluate from a large scale manufacturing process was monitored for protein content, pH, and FXIa activity. Briefly, approximately 19,000 L of cryo-poor plasma was processed, as described herein, to form about 220 kg of Fraction II paste, containing about 70 kg of protein. The Fraction II paste was re-suspended and loaded onto a manufacturing-scale CM-Sepharose column, washed, and eluted, as described above. A sample of the eluate was collected and analyzed after each CV (approximately 350 L) of elution. As shown in Table 11, elevated FXIa values are only found at the end of the CM-Sepharose elution, after the pH of the eluate shifts. The protein concentration of the eluate was monitored at $OD_{280}$ and the first part of the elution was collected and pooled until the $OD_{280}$ fell below 2.0. The second part of the elution was then collected and pooled separately until the $OD_{280}$ fell below 0.2. The first and second eluate pools were then analyzed and compared, as shown in Table 12. Notably, 98% of the IgG yield was found in the first part of the CM eluate and 2% of the IgG yield was found in the second part of the CM eluate. Thus, by terminating the collection of a CM-Sepharose elution pool after the $OD_{280}$ of the eluate falls below 2.0, a significant amount of TGA and FXIa activity can be removed from the preparation, while minimizing the loss of IgG yield.

TABLE 11

Biochemical characterization of samples of the CM-Sepharose eluate taken after the elution of each column volume.

| Sample (CM-Sepharose column 1) | Eluate Volume (L) | OD | pH at the column outlet* | TPUV (g/dL) | FXIa (mU/g) |
|---|---|---|---|---|---|
| LE08L008 1CV | 355 | >2 | 4.37 | 6.57 | 0.61 |
| LE08L008 2CV | 706 | >2 | 4.28 | 1.67 | 2.40 |
| LE08L008 3CV | 1069 | >2 | 4.27 | 0.90 | 4.44 |
| LE08L008 4CV | 1408 | >2 | 7.48 | 0.65 | 86.55 |
| LE08L008 5CV | 1753 | >2 | 8.18 | 0.19 | 101.07 |

TABLE 11-continued

Biochemical characterization of samples of the CM-Sepharose eluate taken after the elution of each column volume.

| Sample (CM-Sepharose column 1) | Eluate Volume (L) | OD | pH at the column outlet* | TPUV (g/dL) | FXIa (mU/g) |
|---|---|---|---|---|---|
| LE08L008 6CV | 2106 | 0.85 | 8.28 | 0.06 | 86.24 |
| LE08L008 7CV | 2451 | 0.26 | 8.34 | 0.00 | n.a. |

TABLE 12

Biochemical characterization of the first and second CM-Sepharose elution pools.

| Test | Unit | First part of the CM-eluate | Second part of the CM-eluate (after OD of 2) |
|---|---|---|---|
| TGA | % of reference plasma at 2.4 mg/mL | 144.64 | 366.65 |
| F-XIa | mU/g IgG | 12.53 | Very high factor XIa like activity; cannot be quantitatively evaluated as product contains also FXa and/or FIXa activities |

Example 10

To further assess the disclosed methods for reducing the amidolytic content of an immunoglobulin composition, a second large-scale experiment was performed, using a Fraction II precipitate as the starting material. Briefly, the Fraction II precipitate was prepared as described in Example 1, except that the separation of precipitate A was performed by filtration, rather than centrifugation.

The Fraction II precipitate was subjected to CM-cation chromatography, as described in Example 1. As in Example 1, the CM eluate was collected in two pools, a leading portion (E1) containing the bulk of the IgG content and a lagging portion (E2) containing the majority of the amidolytic activity. The collection of the first part of the eluate (E1) was started at OD 400 mAU and stopped after exactly 2.7 column volumes. The second fraction (E2) of the elution peak was collected until the OD dropped to 400 mAU again. The eluted fractions were then processed separately for the remainder of the process. The mass balance for the purification process is shown in Table 13.

TABLE 13

Mass balance for second large-scale purification from Fraction II precipitate.

| | TPUV (%) | Protein (g) | Yield (%) | Yield (g/L plasma) |
|---|---|---|---|---|
| Fraction II diss. | 6.14 | 126.72 | 100.00 | 3.02 |
| CWSS | 5.50 | 124.50 | 98.24 | 2.96 |
| CM E1 | 2.96 | 108.73 | 85.80 | 2.59 |
| CM E2 | 0.90 | 16.02 | 12.64 | 0.38 |
| E1 ANX D/N | 2.74 | 94.82 | 74.82 | 2.26 |
| E1 ANX 2M | 0.94 | 10.20 | 8.05 | 0.24 |
| E1 EB | 4.99 | 96.20 | 75.92 | 2.29 |
| E2 ANX D/N | 2.70 | 13.26 | 10.46 | 0.32 |
| E2 ANX 2M | 0.95 | 1.20 | 0.94 | 0.03 |
| E2 EB | 5.42 | 11.81 | 9.32 | 0.28 |

As in Example 1, roughly 10% of the total protein is found in the second part of the elution peak. This is the confirmed yield loss if the elution is stopped after 2.7 column volumes The final containers prepared from the two CM elution fractions (E1 and E2) were analyzed for molecular size distribution, anti-complementary activity, amidolytic activity with the substrate SN13a and with TGA, FXIa, and NAPTT assays. The results are shown in the Table 14 and Table 15.

TABLE 14

Comparison of the molecular size distribution of the two final containers

| HPLC | Polymers | Oligo/Dimers | Monomers | Fragments |
|---|---|---|---|---|
| E1 FC | 0.24% | 5.18% | 93.21% | 1.36% |
| E2 FC | 4.42% | 9.60% | 84.55% | 1.44% |

TABLE 15

Comparison of additional characteristics of the two final containers

| | PKKA PKKA IU/ml | TGA % normal plasma | FXIa mU/ml FXIa | ACA C'H50 units consumed/% | SN13a mU/ml FXIa | NAPTT (FXI Plasma) |
|---|---|---|---|---|---|---|
| E1 FC | <4 | 102.76 | <0.04 | 7.9/9.7% | <0.375 | >5 mg |
| E2 FC | <4 | 119.75 | 0.09 | 52.4/63.7% | 3.23 | >5 mg |

The biochemical characterization of the final containers derived from the first and the second part of the eluted IgG fraction revealed that the first part of the elution is essentially free from FXIa and other undesirable proteins causing elevated TGA and shortened NAPTT values. In contrast, FXIa and amidolytic activities are enriched in the second part, where the aggregate and oligo-/dimer contents are also higher, even if the separation of suspension A is performed by filtration. Interestingly, the ACA value in the first part of the eluate is even lower, while the ACA value in the second part of the eluate is higher.

In this experiment, where filtration is used for separation of suspension A in the upstream process, the residual FXIa in the second part of the elution is much less and the TGA value of the final container of this elution part is in the normal range.

Taken together with Example 1, the split of the elution from the CM Sepharose ff column in two fractions (E1 and E2) enables the manufacturing of an IgG composition that is substantially free of FXIa. This is true for both separation options for fraction A (i.e., centrifugation and filtration), although FXIa is significantly lower if precipitate A separation is performed by filtration.

Example 11

This example demonstrates the suitability of the present methods for the separation of procoagulant activities by cation exchange chromatography in large-scale manufacturing processes designed for the production of immunoglobulin compositions for subcutaneous administration. The starting material for this experiment was a Fraction II precipitate formed from pooled human source plasma collected in Europe, which was cryo-precipitated and used to recover anti-thrombin III (ATIII) via adsorption.

Briefly, after cryo-precipitation and adsorption of ATIII, cold alcohol fractionation starts with the separation of fibrinogen and residual coagulation factors (e.g., Factor XIII) by the precipitation of a fraction I precipitate at 8% alcohol and pH 7.0. The alcohol concentration in the supernatant is adjusted to 25% in order to precipitate fraction II+III and to separate albumin. After the re-suspension of precipitate II+III, alcohol is added to 12% at a pH of −5.2 to form precipitate III. After separation of precipitate III, 0.04 g DEAE Sephadex/g protein are added, the solution is filtered through Cuno 90 depth filters, and the Cohn fraction II containing the purified gamma globulin fraction is precipitated by 25% alcohol at neutral pH.

The fraction II precipitate is dissolved in cold water at 4° C. and pH 5.2±0.2. After clarification by CWSS filtration, the solution is adjusted for the SD treatment to a protein concentration of 2%. The temperature during the SD incubation is held in the range of 20 to 25° C. The protein solution is loaded onto an equilibrated CM-Sepharose fast flow column (equilibration buffer: 0.025 M sodium acetate, pH 5.0±0.2). After the loading, the column is washed with 30 column volumes of acetate buffer (0.01 M sodium acetate. pH 5.5±0.2) to wash out the SD reagents before the adsorbed protein is eluted with elution buffer (0.25 M NaCl, 0.2 M glycine, 0.1% PEG 3350, 25 mM Tris, pH 8.00). The collection of the first part of the eluate (E1) is started at OD 400 mAU and stopped after exactly 2.7 column volumes. The second fraction (E2) of the elution peak is collected until the OD dropped to 400 mAU again. The eluted fractions are separately processed to the final bulk according to the following steps.

The pH of the eluate fraction is adjusted to 5.2 and then the concentration to 5%, the diafiltration against diafiltration buffer (0.02 M NaCl, 0.05% PEG 3350) and the subsequent concentration to 10% protein takes place. 0.055 g glycine/g protein are added to the solution and the pH is adjusted to 7.0 before the sterile filtration.

Figure 3:
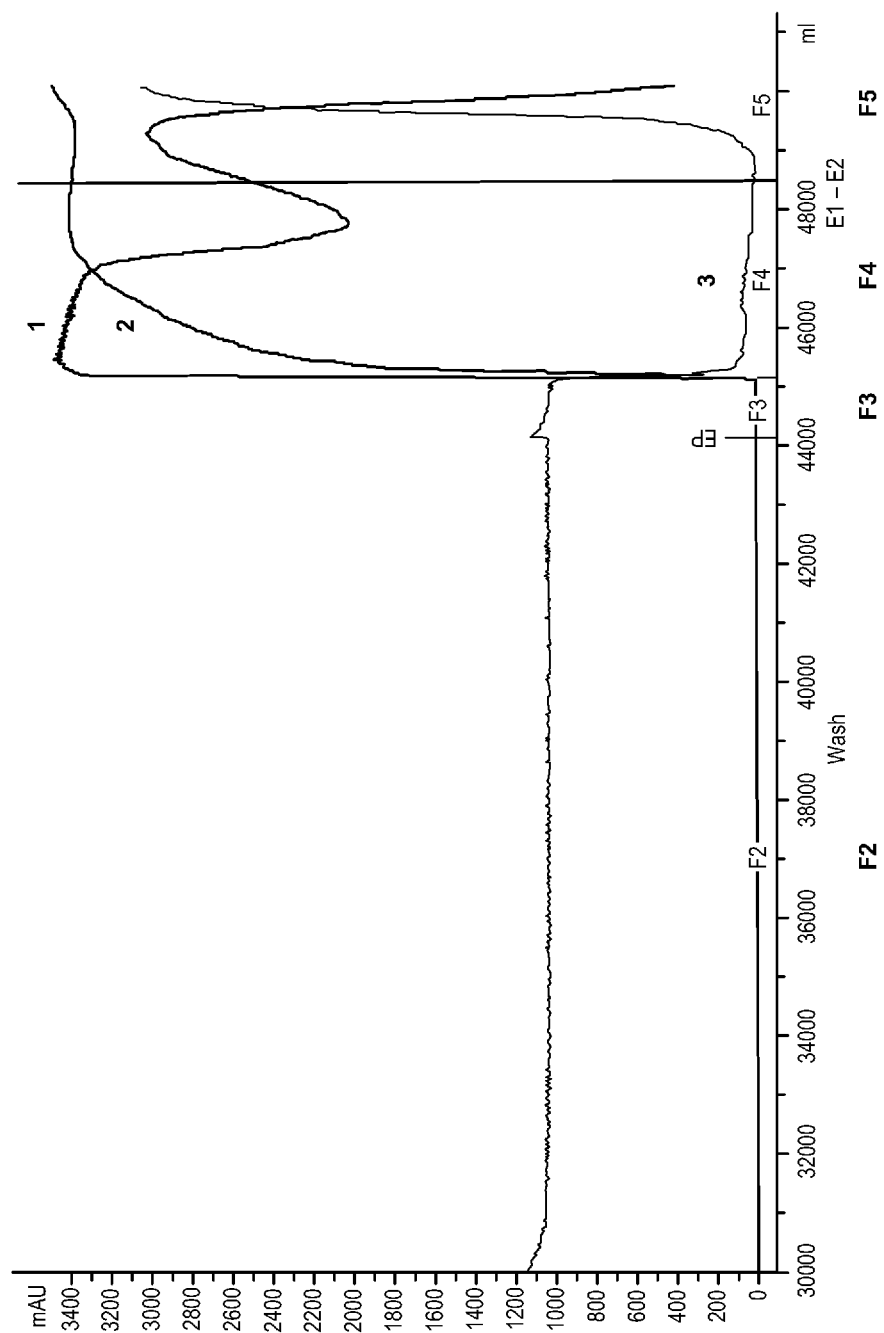
FIG. 3. shows a chromatogram of the CM Sepharose Fast Flow (ff) chromatography step described in Example 11. Line number 1 shows the UV absorbance, line number 3 shows the pH, and line number 2 shows the conductivity of the effluent at the column outlet.

The chromatogram of the cation exchange wash and elution steps is shown in FIG. 3. Line 1 shows the UV absorbance, Line 2 the conductivity, and line 3 the pH at the column outlet. The optical density at 280 nm indicates a partial separation of two fractions during the elution of the protein from the CM Sepharose ff column. The pH at the column outlet starts to rise just after the beginning of the re-rise of the UV absorbance during elution. At this point the two eluate fractions were separated (F4 and F5, referred to herein as E1 and E2). The mass balance for the downstream purification run is shown in Table 16.

TABLE 16

Mass balance for the large-scale purification of IgG from Fraction II precipitate.

| | TPUV (%) | Protein (g) | Yield (%) | Yield (g/l plasma) |
|---|---|---|---|---|
| Fr II diss. | 4.94 | 179.45 | 100.00 | 3.58 |
| CWSS | 2.70 | 169.46 | 94.43 | 3.38 |
| CM E1 | 2.78 | 148.05 | 82.50 | 2.95 |
| CM E2 | 0.85 | 21.04 | 11.72 | 0.42 |
| E1 Bulk | 13.25 | 127.60 | 71.11 | 2.54 |
| E2 Bulk | 13.15 | 20.32 | 11.32 | 0.41 |

Roughly 15% of the total protein is found in the second part of the elution peak (E2). This is the yield loss due to stopping the collection of E1 after 2.7 column volumes. The final containers prepared from the two CM elution fractions (E1 and E2) were analyzed for molecular size distribution, anti-complementary activity, amidolytic activity with the substrate SN13a and with TGA, FXIa, and NAPTT assays. The results are shown in Table 17 and Table 18.

TABLE 17

Comparison of the molecular size distribution of the two final containers.

| HPLC | Polymers | Oligo/Dimers | Monomers | Fragments |
|---|---|---|---|---|
| E1 Bulk | 0.47% | 5.92% | 93.61% | — |
| E2 Bulk | 6.33% | 8.50% | 83.97% | 1.20% |

TABLE 18

Comparison of additional characteristics of the two final containers.

| | PKKA PKKA IU/ml | TGA % normal plasma | FXIa ng/ml FXIa | ACA % | SN13a mU/ml FXIa | NAPTT (FXI Plasma) |
|---|---|---|---|---|---|---|
| E1 Bulk | <4 | 118.34 | 0.095 | 44 | <0.39 | >10 mg |
| E2 Bulk | 16.5 | 109.11 | 0.23 | 57 | 167 | >10 mg |

The first part of the CM-eluate (E1) resulted in a final bulk with lower aggregate, dimer and fragment content, with a low FXIa content, with a TGA result close to normal plasma, with PKA and amidolytic activity as measured with SN-13 below the detection limit and without shortened NAPTT. FXIa, PKKA and FXIa-like activity are enriched in the second part, where the IgG polymer, fragment, and oligo-/dimer content is also higher. Interestingly, the ACA value in the leading portion of the eluate (E1) is lower than in the lagging portion of the eluate (E2).

Example 12

To further assess the disclosed methods for reducing the amidolytic content of an immunoglobulin composition, another large-scale experiment was performed, using a Fraction II precipitate as the starting material. Briefly, the Fraction II precipitate was prepared as described in Example 11, except that the starting material for this experiment was a Fraction II precipitate formed from pooled human source plasma collected in Europe, which was cryo-precipitated and used to recover FEIBA and anti-thrombin III (ATIII) via adsorption. The CM-Sepharose cation exchange chromatography and downstream processing was otherwise performed as described in Example 11.

Figure 4:
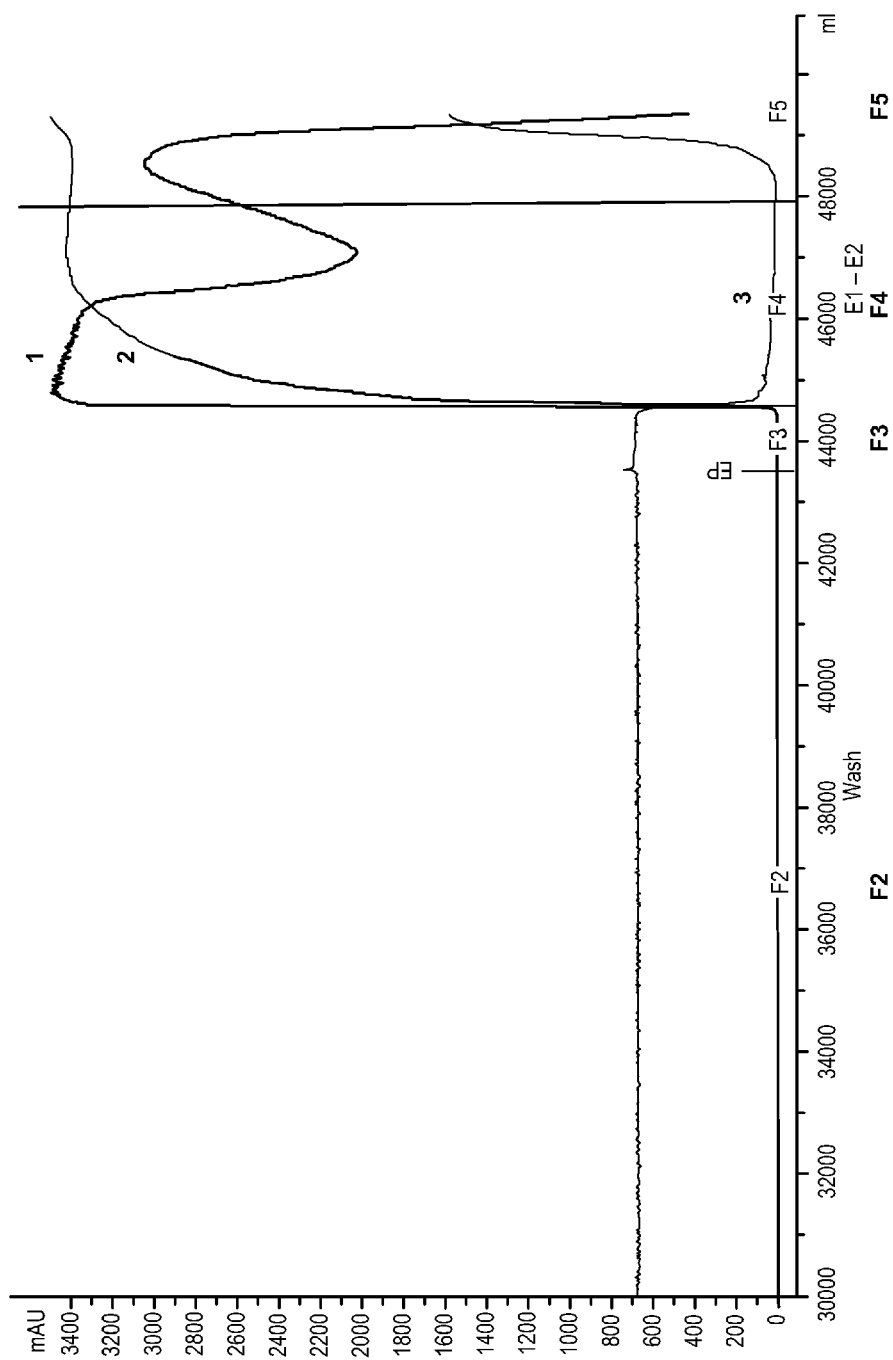
FIG. 4. shows a chromatogram of the CM Sepharose Fast Flow (ff) chromatography step described in Example 12. Line number 1 shows the UV absorbance, line number 3 shows the pH, and line number 2 shows the conductivity of the effluent at the column outlet.

The chromatogram of the cation exchange wash and elution steps is shown in FIG. 4. Line 1 shows the UV absorbance, Line 2 the conductivity, and line 3 the pH at the column outlet. The optical density at 280 nm indicates a partial separation of two fractions during the elution of the protein from the CM Sepharose ff column. The pH at the column outlet starts to rise just after the beginning of the re-rise of the UV absorbance during elution. At this point the two eluate fractions were separated (F4 and F5, referred to herein as E1 and E2). The mass balance for the downstream purification run is shown in Table 19.

TABLE 19

Mass balance for the large-scale purification of IgG from Fraction II precipitate.

| | TPUV (%) | Protein (g) | Yield (%) | Yield (g/l plasma) |
|---|---|---|---|---|
| Fr II diss. | 5.09 | 174.15 | 100.00 | 4.03 |
| CWSS | 2.98 | 168.81 | 96.93 | 3.91 |
| CM E1 | 2.69 | 143.69 | 82.51 | 3.33 |
| CM E2 | 0.94 | 21.28 | 12.22 | 0.49 |
| E1 Bulk | 9.28 | 127.68 | 73.32 | 2.96 |
| E2 Bulk | 9.63 | 19.95 | 11.46 | 0.46 |

As in Example 11, roughly 15% of the total protein is found in the second part of the elution peak. This is the yield loss due to stopping the collection of E1 after 2.7 column volumes. The final containers prepared from the two CM elution fractions (E1 and E2) were analyzed for molecular size distribution, anti-complementary activity, amidolytic activity with the substrate SN13a and with TGA, FXIa, and NAPTT assays. The results are shown in Table 20 and Table 21.

TABLE 20

Comparison of the molecular size distribution of the two final containers.

| HPLC | Polymers | Oligo/Dimers | Monomers | Fragments |
|---|---|---|---|---|
| E1 Bulk | 0.54% | 4.95% | 94.49% | 0.02% |
| E2 Bulk | 6.49% | 6.71% | 85.18% | 1.62% |

TABLE 21

Comparison of additional characteristics of the two final containers.

| | PKKA PKKA IU/ml | TGA % normal plasma | FXIa ng/ml FXIa | ACA % | SN13a mU/ml FXIa | NAPTT (FXI Plasma) |
|---|---|---|---|---|---|---|
| E1 Bulk | <4 | 114.34 | 0.081 | 57 | 1.15 | >10 mg |
| E2 Bulk | 34.2 | 157.18 | 3.208 | 59 | 276 | >10 mg |

The biochemical characterization of the stabilized bulks derived from the first and the second part of the eluted IgG fraction revealed that the first part of the elution is essentially free from FXIa and other undesirable proteins causing elevated TGA and shortened NAPTT values, while PKKA, FXIa and FXIa like activities are enriched in the second part, where the IgG fragment, polymer and oligo-/dimer content is also higher. The ACA values do not differ significantly in the bulks of the first part and the second part of the eluate. The results overall confirm the findings in Example 11.

Example 13

To further assess the disclosed methods for reducing the amidolytic content of an immunoglobulin composition, another large-scale experiment was performed, using a Fraction II precipitate as the starting material. Briefly, the Fraction II precipitate was prepared as described in Example 11, except that the starting material for this experiment was a Fraction II precipitate formed from pooled human source plasma collected in the United States, which was cryo-precipitated and used to recover FEIBA and anti-thrombin III (ATIII) via adsorption. The CM-Sepharose cation exchange chromatography and downstream processing was otherwise performed as described in Example 11.

Figure 5:
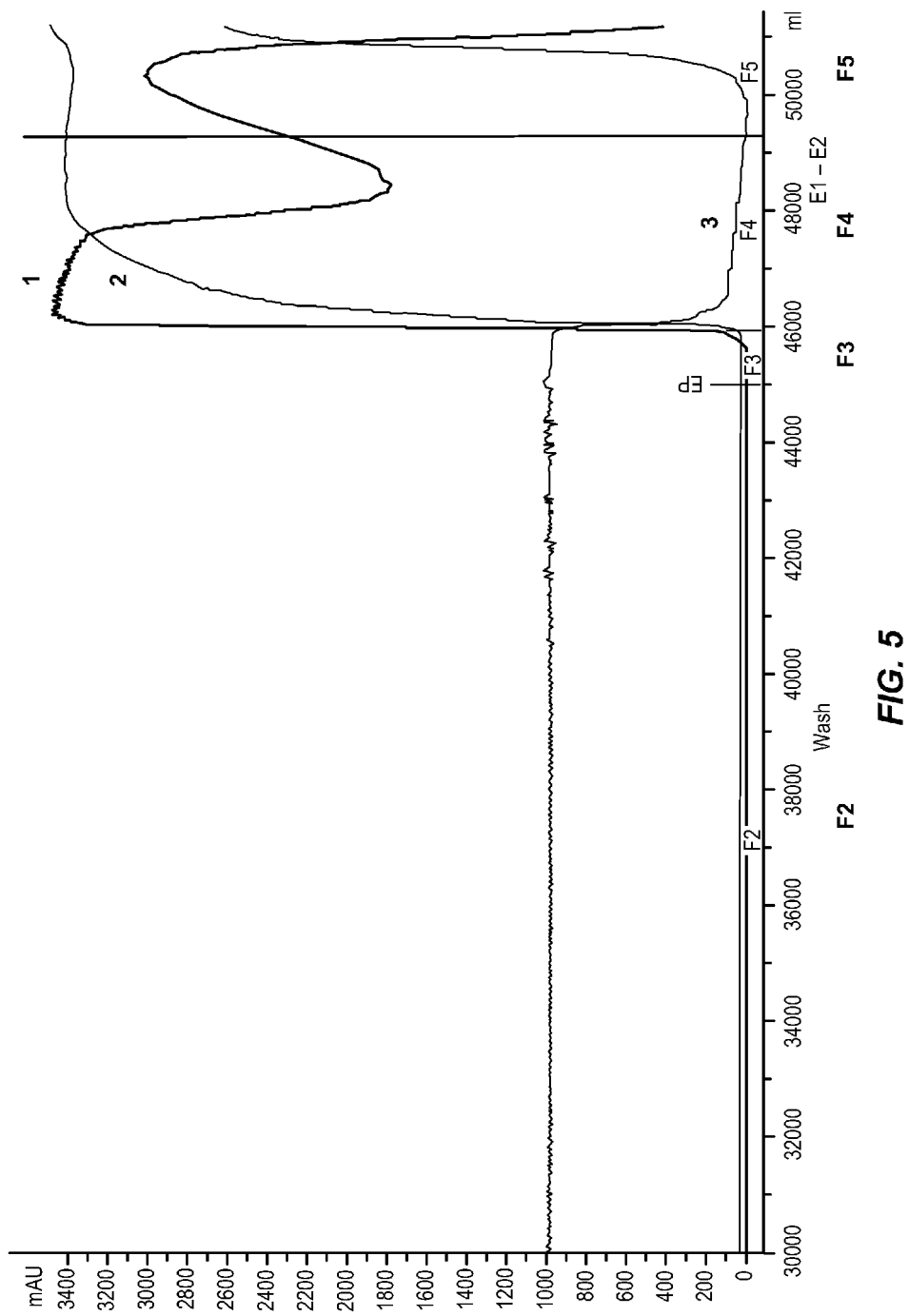
FIG. 5. shows a chromatogram of the CM Sepharose Fast Flow (ff) chromatography step described in Example 13. Line number 1 shows the UV absorbance, line number 3 shows the pH, and line number 2 shows the conductivity of the effluent at the column outlet.

The chromatogram of the cation exchange wash and elution steps is shown in FIG. 5. Line 1 shows the UV absorbance, Line 2 the conductivity, and line 3 the pH at the column outlet. The optical density at 280 nm indicates a partial separation of two fractions during the elution of the protein from the CM Sepharose ff column. The pH at the column outlet starts to rise just after the beginning of the re-rise of the UV absorbance during elution. At this point the two eluate fractions were separated (F4 and F5, referred to herein as E1 and E2). The mass balance for the downstream purification run is shown in Table 22.

TABLE 22

Mass balance for the large-scale purification of IgG from Fraction II precipitate.

|  | TPUV (%) | Protein (g) | Yield (%) | Yield (g/l plasma) |
|---|---|---|---|---|
| Fr II diss. | 4.02 | 125.70 | 100.00 | 3.09 |
| CWSS | 2.31 | 120.19 | 95.62 | 2.95 |
| CM E1 | 2.73 | 104.01 | 82.74 | 2.55 |
| CM E2 | 0.85 | 18.20 | 14.48 | 0.45 |
| E1 Bulk | 9.33 | 91.11 | 72.49 | 2.24 |
| E2 Bulk | 9.01 | 16.35 | 13.00 | 0.40 |

As in Example 11, roughly 15% of the total protein is found in the second part of the elution peak. This is the yield loss due to stopping the collection of E1 after 2.7 column volumes. The final containers prepared from the two CM elution fractions (E1 and E2) were again analyzed for molecular size distribution, anti-complementary activity, PKKA, FXIa like activity with the substrate SN13a and with TGA, FXIa and NAPTT assays. The results are shown in Table 23 and Table 24.

TABLE 23

Comparison of the molecular size distribution of the two final containers.

| HPLC | Polymers | Oligo/Dimers | Monomers | Fragments |
|---|---|---|---|---|
| E1 Bulk | 0.67% | 5.29% | 94.03% | — |
| E2 Bulk | 6.48% | 8.92% | 83.74% | 0.86% |

TABLE 24

Comparison of additional characteristics of the two final containers.

|  | PKKA PKKA IU/ml | TGA % normal plasma | FXIa ng/ml FXIa | ACA % | SN13a mU/ml FXIa | NAPTT (FXI Plasma) |
|---|---|---|---|---|---|---|
| E1 Bulk | <4 | 109.53 | 0.080 | 44 | 1.23 | >10 mg |
| E2 Bulk | 54.6 | 148.17 | 1.652 | 60 | 203 | >10 mg |

The biochemical characterization of the final bulks confirmed the results from Examples 11 and 12. The first part of the elution (E1) is essentially free from FXIa and other undesirable proteins causing elevated TGA and shortened NAPTT values, while FXIa and amidolytic activities are enriched in the second part (E2), where the fragment, polymer and oligo-/dimer content is also higher even if the separation of suspension A is performed by filtration. Interestingly, the ACA value in the stabilized bulk of the first part of the eluate is again lower than in the bulk of the second part of the eluate.

Taken together, the results provided in the Examples above demonstrate that splitting the eluate from a CM Sepharose ff column in two fractions enables the manufacturing of an immunoglobulin composition substantially free of procoagulant activities. This is true for varying plasma sources (EU and US) and upstream processing schemes.

The product losses determined for the immunoglobulin preparations described in Examples 11 to 13 are higher than those seen in Examples 1 to 10. In Examples 11 to 13, division of the eluate peak after 2.7 column volumes results in a loss of about 15% of the total protein. As the pH shift of the eluate occurred later in Examples 11-15, a later elution cut should improve the overall yield, without significantly compromising the separation of procoagulant activities.

The data shown above demonstrate that the division of a cation exchange chromatography eluate is a robust method for the production of immunoglobulin compositions having substantially reduced procoagulant activities.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for reducing Factor XI (FXI) and/or Factor XIa (FXIa) content in a plasma-derived immunoglobulin composition, the method comprising the steps of:
   (a) providing a plasma-derived immunoglobulin composition comprising IgG immunoglobulins and FXI and/or FXIa;
   (b) contacting the plasma-derived immunoglobulin composition with a cation exchange resin disposed in a chromatography column under a first solution condition comprising a pH of no more than 6.0 and a conductivity of no more than 11 mS/cm to bind the IgG immunoglobulins and at least a fraction of the FXI and/or FXIa to the cation exchange resin;
   (c) eluting the IgG immunoglobulins from the cation exchange resin in a single-step elution by contacting the cation exchange resin with an elution buffer comprising a pH of at least 7.5 and a conductivity of at least 15 mS/cm to form an eluate comprising a leading portion and lagging portion; and
   (d) collecting the leading portion of the eluate separately from the lagging portion of the eluate,
   wherein the leading portion of the eluate consists of the portion of the eluate having a pH of no more than 6.0, and wherein less than 50% of the FXI and/or FXIa bound to the cation exchange resin in step (b) is present in the leading portion of the eluate collected in step (d).

2. The method of claim 1, wherein the elution buffer comprises a conductivity of at least 20 mS/cm.

3. The method of claim 1, wherein the elution buffer comprises a conductivity of at least 25 mS/cm.

4. The method of claim 1, further comprising a step of washing the cation exchange resin having the immunoglobulins and FXI and/or FXIa bound thereto with a wash buffer comprising a pH of no more than 6.0 and a conductivity of less than 11 mS/cm prior to eluting the immunoglobulins from the cation exchange resin in step (c).

5. The method of claim 1, wherein the cation exchange resin is a weak cation exchange resin.

6. The method of claim 5, wherein the weak cation exchange resin is carboxymethyl cation exchange resin.

7. The method of claim 1, wherein the elution buffer comprises a pH of between 7.5 and 8.5.

8. The method of claim 7, wherein the elution buffer comprises a pH of 8.0±0.2.

9. The method of claim 1, wherein the elution buffer comprises between 200 and 300 mM sodium chloride.

10. The method of claim 9, wherein the elution buffer comprises between 240 and 260 mM sodium chloride.

11. The method of claim 1, wherein the elution buffer comprises between 100 mM and 300 mM glycine.

12. The method of claim 11, wherein the elution buffer comprises between 175 mM and 225 mM glycine.

13. The method of claim 1, wherein the step of collecting the leading portion of the eluate separately from the lagging portion of the eluate comprises collecting eluate having a pH of no more than 6.0 separately from eluate having a pH of more than 6.0.

14. The method of claim 1, wherein the step of collecting the leading portion of the eluate separately from the lagging portion of the eluate comprises collecting eluate having a pH of no more than 5.5 separately from eluate having a pH of more than 5.5.

15. The method of claim 1, wherein the step of collecting the leading portion of the eluate separately from the lagging portion of the eluate comprises collecting eluate having a pH of no more than 5.0 separately from eluate having a pH of more than 5.0.

16. The method of claim 1, wherein the step of collecting the leading portion of the eluate separately from the lagging portion of the eluate comprises monitoring the pH of the eluate.

17. The method of claim 1, wherein the step of collecting the leading portion of the eluate comprises the sub-steps of:
 (i) monitoring the optical density of the eluate at 280 nm ($OD_{280}$);
 (ii) beginning collection when the $OD_{280}$ of the eluate rises above a first threshold $OD_{280}$ of at least 50 mAU; and
 (iii) ending collection when the $OD_{280}$ of the eluate falls below a second threshold $OD_{280}$ of no less than 500 mAU.

18. The method according to claim 17, wherein the second threshold $OD_{280}$ is no less than 1 AU.

19. The method according to claim 17, wherein the second threshold $OD_{280}$ is no less than 2 AU.

20. The method of claim 4, wherein the wash buffer comprises a pH of between 5.0 and 6.0.

21. The method of claim 20, wherein the wash buffer comprises a pH of 5.5±0.2.

22. The method of claim 1, wherein less than 25% of the FXI and/or FXIa bound to the cation exchange resin in step (b) is present in the leading portion of the eluate collected in step (d).

23. The method of claim 1, wherein less than 10% of the FXI and/or FXIa bound to the cation exchange resin in step (b) is present in the leading portion of the eluate collected in step (d).

24. The method of claim 1, wherein the amount of FXI and/or FXIa is determined by performing an amidolytic activity assay using a FXIa-specific substrate.

25. The method of claim 1, wherein the plasma-derived immunoglobulin composition provided in step (a) is a suspended plasma fraction precipitate selected from the group consisting of a Fraction I precipitate, a Fraction I+II+III precipitate, a Fraction II+III precipitate, Fraction IV-1, a Kistler-Nitschmann Precipitate A, a Kistler-Nitschmann Precipitate B, and a modified precipitate thereof.

26. The method of claim 25, wherein the plasma-derived immunoglobulin composition provided in step (a) is a suspended Fraction II precipitate.

27. The method of claim 1, wherein the leading portion of the eluate consists of the portion of the eluate having a pH of from 4.0 to 5.0.

28. The method of claim 1, wherein the leading portion of the eluate consists of the portion of the eluate having a pH of from 4.0 to 5.5.

* * * * *